United States Patent
Deaton et al.

(10) Patent No.: US 7,288,541 B2
(45) Date of Patent: Oct. 30, 2007

(54) PROPYLCARBAMATE DERIVATIVES AS INHIBITORS OF SERINE AND CYSTEINE PROTEASES

(75) Inventors: David Norman Deaton, Durham, NC (US); John George Catalano, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 569 days.

(21) Appl. No.: 10/492,059

(22) PCT Filed: Oct. 2, 2002

(86) PCT No.: PCT/US02/31480

§ 371 (c)(1),
(2), (4) Date: Apr. 8, 2004

(87) PCT Pub. No.: WO03/031437

PCT Pub. Date: Apr. 17, 2003

(65) Prior Publication Data

US 2005/0043368 A1    Feb. 24, 2005

Related U.S. Application Data

(60) Provisional application No. 60/327,938, filed on Oct. 9, 2001.

(51) Int. Cl.
*A61K 31/535* (2006.01)
*A61K 31/415* (2006.01)
*A61K 31/44* (2006.01)
*C07D 417/00* (2006.01)
*C07D 401/00* (2006.01)

(52) U.S. Cl. .................. 514/237.2; 514/341; 514/385; 514/394; 514/338; 514/333; 514/489; 514/367; 514/343; 546/272.7; 546/273.4; 546/278.4; 546/275.4; 546/275.1; 546/261; 544/132; 562/32

(58) Field of Classification Search ................ 514/338, 514/341, 385, 394, 237.2, 333, 489; 546/272.7, 546/273.4, 275.1, 275.4, 261, 270.1; 562/32; 544/132

See application file for complete search history.

(56) References Cited

U.S. PATENT DOCUMENTS

4,552,866 A    11/1985    Gordon et al.
5,047,400 A    9/1991    Vincent et al.

FOREIGN PATENT DOCUMENTS

WO    98/16505    4/1998

OTHER PUBLICATIONS

Groarke, et. al. "Synthesis of ketomethylene amino pseudopeptide analogues via reductive amination of glyoxals derived from alpha-amino acids", Bioorganic & Medicinal Chemistry Letters, vol. 10, No. 2, Junary 2000.*
"Design and Synthesis of Novel [60]Fullerene Derivatives as Poetential HIV Aspartic Protease Inhibitors", Marcorin et. al., Organic Letters, 200, vol. 2, No. 25, 3955-3958.*
Groakre, M. et al., "Synthesis fo ketomethylene amino pseudopeptide analogues via reductive amination of glyoxals derived from alpha-amino acids," *Bioorganic & Medicinal Chemistry Letters*, vol. 10, No. 2, Jan. 2000, pp. 153-155.

* cited by examiner

*Primary Examiner*—Bernard Dentz
*Assistant Examiner*—Binta Robinson
(74) *Attorney, Agent, or Firm*—Kathryn L. Coulter; John L. Lemanowicz

(57) ABSTRACT

The present invention includes ketone derivatives (I) and (II), which are useful as cathepsin K inhibitors. The described invention also includes methods of making such ketone derivatives as well as methods of using the same in the treatment of disorders, including osteoporosis

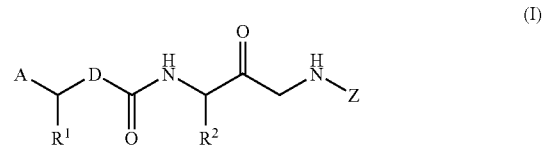
(I)

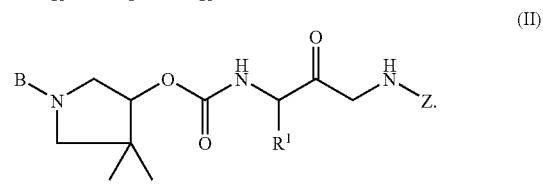

(II)

33 Claims, No Drawings

PROPYLCARBAMATE DERIVATIVES AS INHIBITORS OF SERINE AND CYSTEINE PROTEASES

This application is filed pursuant to 35 U.S.C. § 371 as a United States National Phase Application of International Application No. PCT/US02/31480 filed Oct. 2, 2002, which claims priority from U.S. Pat. No. 60/327,938 filed Oct. 9, 2001.

FIELD OF THE INVENTION

The present invention relates to ketone derivatives, compositions and medicaments containing the same, as well as processes for the preparation and use of such compounds, compositions and medicaments. Such ketone derivatives are inhibitors of serine and cysteine proteases. Particularly, such ketone derivatives are inhibitors of cysteine proteases of the papain superfamily. More particularly, the ketones of the present invention are inhibitors of cathepsin family cysteine proteases such as cathepsin K. Such ketone derivatives are useful in the treatment of diseases associated with serine and cysteine protease activity, more particularly, in the treatment of diseases associated with cathepsin family cysteine proteases, for instance in the treatment of diseases associated with cathepsin K activity.

BACKGROUND OF THE INVENTION

Osteoclasts are multinuclear cells of hematopoietic lineage, which function in the process of bone resorption. Typically, bone resorption proceeds through osteoclast adherence to a bone surface and formation of a tight sealing zone. This activity is followed by extensive membrane ruffling on the surface of the osteoclasts. Such action creates an enclosed extracellular compartment on the bone surface that is acidified by proton pumps in the ruffled membrane and into which the osteoclast secretes proteolytic enzymes. The low pH of the compartment dissolves hydroxyapatite crystals at the bone surface, while the proteolytic enzymes digest the protein matrix. In this way a resorption pit is formed. At the completion of this cycle osteoblasts remodel the bone; that is, they deposit a new protein matrix that is subsequently mineralized at this zone.

Normally, a balance exists between the processes of bone resorption and new bone formation during remodeling. This normal balance of bone resorption and bone formation, however, may be disrupted resulting in a net loss of bone in each cycle of remodeling. Osteoporosis is a reduction in the quantity of bone or atrophy of skeletal tissue. Osteoporosis is characterized by reduced bone mass and disruptions in the microarchitecture of the bone. These characteristics may lead to fractures, which can result from a minimal amount of trauma. Typical sites of fractures include vertebral bodies, distal radius, and the proximal femur. However, because those suffering from osteoporosis have general skeletal weakness, fractures may occur at other sites.

Since osteoporosis is characterized by an increase in bone resorption with respect to bone remodeling, therapeutic agents that suppress bone resorption should provide a suitable treatment for osteoporosis. Administration of estrogens or calcitonin has been the bone resorption suppression treatment typically employed. However, these treatments do not always achieve the desired effect. Consequently, there is a continuing need for therapeutic agents which can attenuate bone resorption in a subject in need of such attenuation.

Cathepsin K, which has also been called cathepsin O, cathepsin O2, and cathepsin X, is a member of the cysteine cathepsin family of enzymes, which are part of the papain superfamily of cysteine proteases. Other distinct cysteine protease cathepsins, designated cathepsin B, cathepsin C, cathepsin F, cathepsin H, cathepsin L, cathepsin S, cathepsin V (also called L2), cathepsin W, & cathepsin Z (also called cathepsin X), have also been described in the literature. Cathepsin K polypeptide and the cDNA encoding such polypeptide are discussed in U.S. Pat. No. 5,501,969. A crystal structure for cathepsin K is disclosed in PCT Patent Application WO 97/16177, published May 9, 1997. Cathepsin K is abundantly expressed in osteoclasts under normal conditions and may be the major cysteine protease present in these cells. See, Tezuka, et al., *J. Biol. Chem.,* 1994, 269, 1106; Inaoka, et al, *Biochem. Biophys. Res. Commun.,* 1995, 206, 89; and Shi, et al., *FEBS Lett.,* 1995, 357,129. This abundant selective expression of cathepsin K in osteoclasts suggests that this enzyme is essential for bone resorption. Thus, selective inhibition of cathepsin K may provide an effective treatment for diseases of excessive bone loss, such as osteoporosis.

The selective inhibition of cathepsin K may also be useful in treating other diseases and conditions. Such disorders include autoimmune diseases such as rheumatoid arthritis, osteoarthritis, neoplastic diseases, parasitic diseases, and atherosclerosis. For instance, cathepsin K is expressed in the synovium and synovial bone destruction sites of patients with rheumatoid arthritis. See Votta, B. J. et al.; *J. Bone Miner. Res.* 1997, 12, 1396; Hummel, K. M. et al., *J. Rheumatol.* 1998, 25, 1887; Nakagawa, T. Y. et al., *Immunity* 1999, 10, 207; Otsuka, T. et al., *J. Antibiot.* 1999, 52, 542; Li, Z. et al, *Biochemistry* 2000, 39, 529; Diaz, A. et al., *Mol. Med.* 2000, 6, 648; Moran, M. T. et al., *Blood* 2000, 96, 1969.

Cathepsin K levels are elevated in chondroclasts of osteoarthritic synovium See Dodds, R. A. et al., *Arthritis Rheum.* 1999, 42, 1588; Lang, A. et al., *J. Rheumatol* 2000, 27, 1970).

Neoplastic cells also have been shown to express cathepsin K. See, Littlewood-Evans, A. J. et al., *Cancer Res.* 1997, 57, 5386; Komarova, E. A., et al., *Oncogene* 1998, 17, 1089; Santamaria, I., et al., *Cancer Res.* 1998, 58, 1624; Blagosklonny, M. V. et al., *Oncogene* 1999, 18, 6460; Kirschke, H. et al., *Eur. J. Cancer* 2000, 36, 787; Zhu, D.-M. et al., *Clin. Cancer Res.* 2000, 6, 2064.

Cysteine protease inhibitors have been suggested as chemotherapy for parasitic diseases. See, McKerrow, J. H. *Int. J. Parasitol* 1999, 29, 833; Selzer, P. M. et al., *Proc. Natl. Acad. Sci* 1999, 96, 11015; Caffrey, C. R. et al., *Curr. Drug Targets* 2000, 1, 155; Du, X. et al., *Chem. Biol.* 2000, 7, 733; Hanspal, M. *Biochim. Biophys. Acta* 2000, 1493, 242; Werbovetz, K. A. *Curr. Med. Chem* 2000, 7, 835.

Elastolytic cathepsins S and K are shown to be expressed in human atheroma. See, Sukhova, G. K. et al., *J. Clin. Invest* 1998, 102, 576–583; Parks, W. C. *J. Clin. Invest* 1999, 104, 1167; Shi, G.-P. et al., *J. Clin. Invest* 1999, 104, 1191; Cao, H. et al., *J. Hum. Genet* 2000, 45, 94.

The present inventors have now discovered novel ketone derivative compounds, which are inhibitors of serine and cysteine protease activities, more particularly, cathepsin family cysteine protease activities, and most particularly, cathepsin K activity. Such ketone derivatives are useful in the treatment of disorders associated with serine and cysteine protease activity, including osteoporosis, Paget's disease, hypercalcemia of malignancy, metabolic bone disease, osteoarthritis, rheumatoid arthritis, periodontitis, gingivitis, atherosclerosis, and neoplastic diseases associated with cathepsin K activity.

BRIEF SUMMARY OF THE INVENTION

In a first aspect, the present invention includes compounds of Formula (I):

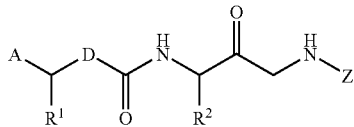

(I)

or a salt, solvate, or pharmaceutically functional derivative thereof, wherein
A is the group defined by $(Q^3)_p\text{-}(Q^2)_n\text{-}(Q^1)\text{-}(Q)_m\text{-}$, wherein
  Q is $CH_2$ and m is 0, 1, or 2, or
  Q is $OCH_2$ and m is 0 or 1, or
  Q is $N(R^3)CH_2$ and m is 0 or 1, where $R^3$ is hydrogen or $C_1$–$C_6$ alkyl;
  $Q^1$ is aryl, heteroaryl, or heterocyclyl;
  $Q^2$ is $CH_2$ and n is 0 or 1, or
  $Q^2$ is O and n is 0 or 1, or
  $Q^2$ is $N(R^3)$ and n is 0 or 1, where $R^3$ is hydrogen or $C_{1-C6}$ alkyl;
  $Q^3$ is aryl or heteroaryl and p is 0 or 1;
$R^1$ is alkyl or cycloalkyl, said cycloalkyl may be optionally substituted with alkyl;
D is O or S;
$R^2$ is hydrogen or alkyl; and
Z is $-(X^1)_q-(X^2)$;
  wherein $X^1$ is $S(O)_2$, $C(O)$, or $-CH_2-$, and q is 0, 1, or 2; and
  $X^2$ is aryl, heteroaryl, or heterocyclyl.

In a second aspect, the present invention includes compounds of Formula (II):

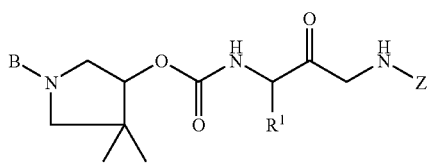

(II)

or a salt, solvate, or pharmaceutically functional derivative thereof, wherein
B is $-(Q^1)_a-(Q^2)_b-(Q^3)$,
wherein,
  $Q^1$ is $C(O)$, $S(O)_2$, or $CR^2R^3$, where $R^2$ and $R^3$ each are independently selected from hydrogen or $C_{1-C6}$ alkyl, and a is 0, 1, 2, or 3;
  $Q^2$ is O, S, $NR^2$, or $CR^2R^3$, where $R^2$ and $R^3$ each are independently selected from hydrogen or $C_1$–$C_6$ alkyl, and b is 0, 1, 2, or 3; and
  $Q^3$ is aryl, heteroaryl, heterocyclyl, aralkyl, or alkylene-heterocyclyl;
$R^1$ is hydrogen or alkyl;
Z is $-(X^1)_q-(X^2)$;
  wherein $X^1$ is $S(O)_2$, $C(O)$, or alkyl, and q is 0 or 1; and
  $X^2$ is aryl, heteroaryl, or heterocyclyl.

In a third aspect of the present invention, there is provided a pharmaceutical composition comprising: a therapeutically effective amount of a compound of formula (I) or (II), or a salt, solvate, or a physiologically functional derivative thereof and one or more of pharmaceutically acceptable carriers, diluents, and excipients.

In a fourth aspect of the present invention, there is provided a method of treating a disorder in a mammal, said disorder being characterized by bone loss, comprising: administering to said mammal a therapeutically effective amount of a compound of formula (I) or (II) or a salt, solvate or a physiologically functional derivative thereof.

In a fifth aspect of the present invention, there is provided a compound of formula (I) or (II), or a salt, solvate, or a physiologically functional derivative thereof for use in therapy.

In a sixth aspect of the present invention, there is provided the use of a compound of formula (I) or (II), or a salt, solvate, or a physiologically functional derivative thereof in the preparation of a medicament for use in the treatment of a disorder characterized by bone loss.

In a seventh aspect of the present invention, there is provided a method of treating osteoporosis including administering to said mammal a therapeutically effective amount of a compound of formula (I) or (II), or a salt, solvate or physiologically functional derivative thereof.

In an eighth aspect of the present invention, there is provided a method of treating osteoporosis including administering to said mammal therapeutically effective amounts of (i) a compound of formula (I) or (II), or a salt, solvate or physiologically functional derivative thereof and (ii) at least one bone building agent. The bone building agent may be, for example, parathyroid hormone (PTH).

DETAILED DESCRIPTION OF THE INVENTION

As used herein, the term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "lower" refers to a group having between one and six carbons.

As used herein, the term "alkyl" refers to a straight or branched chain hydrocarbon, preferably having from one to twelve carbon atoms, optionally substituted with substituents selected from the group consisting of lower alkyl, lower alkoxy, lower alkylsulfanyl, lower alkylsulfenyl, lower alkylsulfonyl, oxo, mercapto, amino optionally substituted by alkyl, carboxy, carbamoyl optionally substituted by alkyl, aminosulfonyl optionally substituted by alkyl, nitro, or lower perfluoroalkyl, multiple degrees of substitution being allowed. Examples of "alkyl" as used herein include, but are not limited to, methyl, ethyl, propyl, isopropyl, isobutyl, n-butyl, tert-butyl, isopentyl, n-pentyl, and the like.

As used herein, the term "$C_n$-$C_m$ alkyl" refers to an alkyl group, as defined above, which contains the specified number of carbon atoms.

As used herein, the term "alkylene" refers to a straight or branched chain divalent hydrocarbon radical, preferably having from one to ten carbon atoms. Alkylene groups may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, and lower perfluoroalkyl. Multiple degrees of substitution are allowed. Examples of "alkylene" as used herein include, but are not limited to, methylene, ethylene, n-propylene, n-butylene, and the like.

As used herein, the term "$C_n$–$C_m$ alkylene" refers to an alkylene group, as defined above, which contains the specified number of carbon atoms.

As used herein, the term "halogen" refers to fluorine, chlorine, bromine, or iodine.

As used herein, the term "haloalkyl" refers to an alkyl group, as defined herein, that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo and iodo. The term "haloalkyl" should be interpreted to include such substituents as perfluoroalkyl and the like.

As used herein, the term "cycloalkyl" refers to a non-aromatic cyclic hydrocarbon ring, which optionally includes an alkylene linker through which the cycloalkyl may be attached. Exemplary "cycloalkyl" groups include, but are not limited to, cyclopropyl, cyclobutyl, cyclopentyl, cyclohexyl, and cycloheptyl.

As used herein, the term "heterocyclic" or the term "heterocyclyl" refers to a heterocyclic ring, preferably three to twelve-membered; being either saturated or having one or more degrees of unsaturation. These heterocyclic rings contain one or more nitrogen, sulfur, and/or oxygen atoms, where N-oxides, sulfur oxides, and dioxides are permissible heteroatom substitutions. Optionally, as used herein, the heterocyclics may be substituted with substituents selected from the group consisting of lower alkyl, lower haloalkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include lower alkyl, cycloalkyl, lower haloalkyl, lower alkoxy, aryloxy, aralkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower haloalkyl, heteroaryl, or aryl. Multiple degrees of substitution should be considered as included within the present invention. Examples of "aryl" groups include, but are not limited to, phenyl, 2-naphthyl, 1-naphthyl, and biphenyl, as well as substituted derivatives thereof.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen atoms, where N-oxides and sulfur oxides and dioxides are permissible heteroatom substitutions and may be optionally substituted with up to three members selected from a group consisting of lower alkyl, lower haloalkyl, cycloalkyl, lower alkoxy, aryloxy, aralkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower haloalkyl, heteroaryl, or aryl. Multiple degrees of substitution should be considered within the scope of the present invention. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "aralkyl" refers to an aryl or heteroaryl group, as defined herein, attached through an alkylene linker. Examples of "aralkyl" include, but are not limited to benzyl, phenylpropyl, 2-pyridylmethyl, 3-isoxazolylmethyl, 5-methyl-3-isoxazolylmethyl, and 2-imidazoyly ethyl.

As used herein, the term "arylamino" refers to an aryl or heteroaryl group, as defined herein, attached through an amino group —NR'—, wherein R' is as defined herein.

As used herein, the term "alkoxy" refers to the group $R_aO$—, where $R_a$ is alkyl as defined above and the term "$C_n$–$C_m$ alkoxy" refers to the group $R_aO$—, where $R_a$ is $C_n$–$C_m$ alkyl.

As used herein, the term "aryloxy" refers to the group $R_bO$—, where $R_b$ is aryl or heteroaryl as defined above.

As used herein the term "aralkoxy" refers to the group $R_bR_aO$—, where $R_a$ is alkylene and $R_b$ is aryl or heteroaryl, each as defined above.

As used herein, the term "haloalkoxy" refers to the group $R_aO$—, where $R_a$ is haloalkyl as defined above and the term "$C_n$–$C_m$ haloalkoxy" refers to the group $R_aO$—, where $R_a$ is $C_n$–$C_m$ haloalkyl as defined above.

As used herein, the term "oxo" refers to the group =O

As used herein, the term "mercapto" refers to the group —SH.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$—.

As used herein, the term "alkylsulfanyl" refers to the group $R_aS$—, where $R_a$ is alkyl as defined above.

As used herein, the term "alkylsulfenyl" refers to the group $R_aS(O)$—, where $R_a$ is alkyl as defined above.

As used herein, the term "alkylsulfonyl" refers to the group $R_aS(O)_2$—, where $R_a$ is alkyl as defined above.

As used herein, the term "aminosulfonyl" refers to the group —S(O)$_2$NH$_2$.

As used herein, the term "cyano" refers to the group —CN.

As used herein the term "cyanoalkyl" refers to the group —R$_a$CN wherein R$_a$ is an alkylene as defined above. Exemplary "cyanoalkyl" groups useful in the present invention include, but are not limited to cyanomethyl, cyanoethyl, and cyanopropyl.

As used herein, the term "carboxy" refers to the group —COOH.

As used herein, the term "carbamoyl" refers to the group —C(O)NH$_2$.

As used herein, the term "acyl" refers to the group R$_a$C(O)—, where R$_a$ is alkyl, cycloalkyl, or heterocycyll as defined herein.

As used herein, the term "aroyl" refers to the group R$_b$C(O)—, where R$_b$ is aryl as defined herein.

As used herein, the term "heteroaroyl" refers to the group R$_b$C(O)—, where R$_b$ is heteroaryl as defined herein.

As used herein, the term "alkoxycarbonyl" refers to the group R$_a$OC(O)—, where R$_a$ is alkyl as defined herein.

As used herein, the term "acyloxy" refers to the group R$_a$C(O)O—, where R$_a$ is alkyl, cycloalkyl, or heterocyclyl as defined herein.

As used herein, the term "aroyloxy" refers to the group R$_b$C(O)O—, where R$_b$ is aryl as defined herein.

As used herein, the term "heteroaroyloxy" refers to the group R$_b$C(O)O—, where R$_b$ is heteroaryl as defined herein.

As used herein, the term "optionally" means that the subsequently described event(s) may or may not occur, and includes both event(s) that occur, and events that do not occur.

The compounds of formulas (I) and (II) have the ability to crystallize in more than one form, a characteristic known as polymorphism, and it is understood that such polymorphic forms ("polymorphs") are within the scope of formulas (I) and (II). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically or diastereomerically enriched mixtures. Also included within the scope of the invention are the individual isomers of the compounds represented by formula (I) and (II), as well as any wholly or partially equilibrated mixtures thereof. The present invention also covers the individual isomers of the compounds represented by the formulas above as mixtures with isomers thereof in which one or more chiral centers are inverted.

The following embodiments refer to compounds within the scope of both formula (I) and formula (II) as defined above unless specifically limited by the definition of each formula or specifically limited otherwise. It is also understood that the embodiments of the present invention described herein, including uses and compositions, are applicable to both formula (I) and formula (II).

One embodiment of the present invention includes compounds of formula (I):

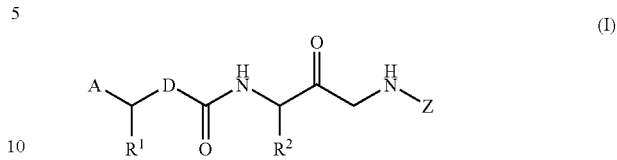

or a salt, solvate, or physiological functional derivatives thereof, wherein A is the group defined by (Q$^3$)$_p$-(Q$^2$)$_n$-(Q$^1$)-(Q)$_m$-, wherein Q is CH$_2$ and m is 0, 1, or 2, or Q is OCH$_2$ and m is 0 or 1, or Q is N(R$^3$)CH$_2$ and m is 0 or 1, where R$^3$ is hydrogen or C$_1$–C$_6$ alkyl; further wherein Q$^1$ is aryl, heteroaryl, or heterocyclyl; further wherein Q$^2$ is CH$_2$ and n is 0 or 1, or Q$^2$ is O and n is 0 or 1, or Q$^2$ is N(R$^3$) and n is 0 or 1, where R$^3$ is hydrogen or C$_1$–C$_6$ alkyl; further wherein Q$^3$ is aryl or heteroaryl and p is 0 or 1; further wherein R$^1$ is alkyl or cycloalkyl, said cycloalkyl may be optionally substituted with alkyl; further wherein D is O or S; further wherein R$^2$ is hydrogen or alkyl; and further wherein Z is —(X$^1$)$_q$—(X$^2$); wherein X$^1$ is S(O)$_2$, C(O), or —CH$_2$—, and q is 0, 1, or 2; and X$^2$ is aryl, heteroaryl, or heterocyclyl.

Preferably, Q is CH$_2$ and m is 1. Preferably, Q$^1$ is aryl, heteroaryl, or heterocyclyl. More preferably, Q$^1$ is

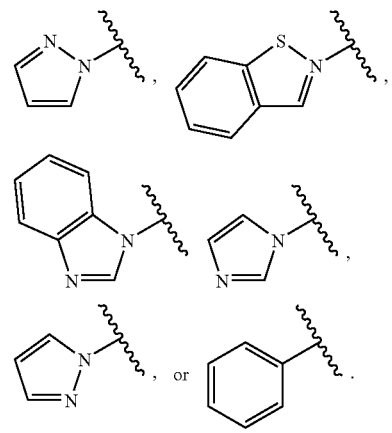

Preferably, n is 0. Preferably, Q$^3$ is aryl or heteroaryl, and p is 1. Preferably, Q$^3$ is

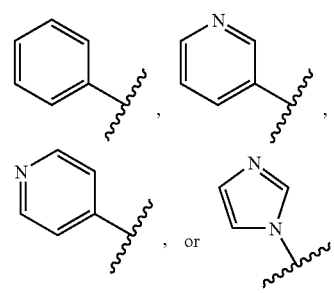

More preferably, the aryl is substituted with haloalkyl.
Preferably, A is

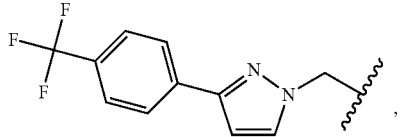,

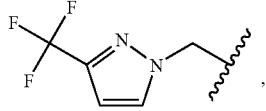,

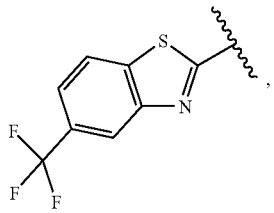,

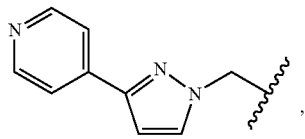,

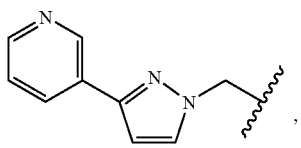,

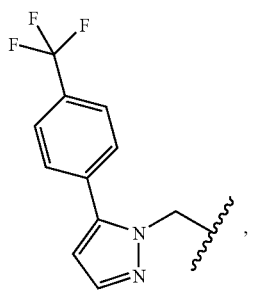,

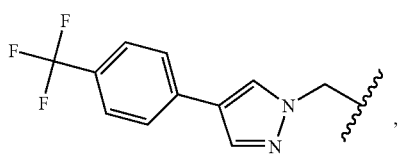,

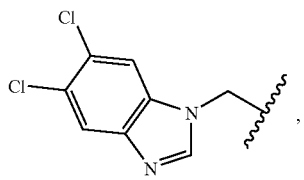,

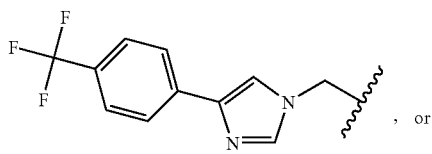, or

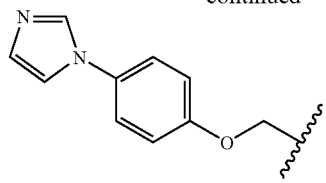

Preferably $R^1$ is lower alkyl. More preferably, $R^1$ is t-butyl. More preferably, $R^1$ is

.

Preferably $R^2$ is hydrogen, methyl, or n-butyl. More preferably, $R^2$ is methyl or n-butyl. More preferably $R^2$ is n-butyl, more preferably $R^2$ is

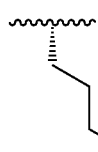.

Preferably, Z is —$(X^1)_q$—$(X^2)$ wherein $X^1$ is $S(O)_2$; q is 1; and $X^2$ is heteroaryl or heterocyclyl. More preferably, Z is

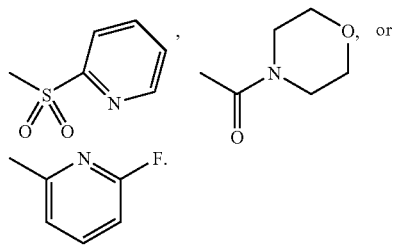

The scope of the present invention includes the following compounds:
(1S)-2,2-dimethyl-1-({3-[4-(trifluoromethyl)phenyl]-1H-pyrazol-1-yl}methyl)propyl 2-oxo-3-[(2-pyridinylsulfonyl)amino]propylcarbamate;
(1S)-2,2-dimethyl-1-({3-[4-(trifluoromethyl)phenyl]-1H-pyrazol-1-yl}methyl)propyl (1S)-1-methyl-2-oxo-3-[(2-pyridinylsulfonyl)amino]propylcarbamate;
(1S)-2,2-dimethyl-1-({3-[4-(trifluoromethyl)phenyl]-1H-pyrazol-1-yl}methyl)propyl (1S)-1-{[(2-pyridinylsulfonyl)amino]acetyl}pentylcarbamate;
(1S)-2,2-dimethyl-1-({3-[4-(trifluoromethyl)phenyl]-1H-pyrazol-1-yl}methyl)propyl (1S)-1-{[(4-morpholinylcarbonyl)amino]acetyl}pentylcarbamate;
(1S)-2,2-dimethyl-1-({3-[4-(trifluoromethyl)phenyl]-1H-pyrazol-1-yl}methyl)propyl (1S)-1-{[(6-fluoro-2-pyridinyl)amino]acetyl}pentylcarbamate;
(3S)-1-(1,3-benzothiazol-2-yl)-4,4-dimethylpyrrolidinyl (1S)-1-{[(2-pyridinylsulfonyl)amino]acetyl}pentylcarbamate;

(1S)-2,2-dimethyl-1-{[3-(trifluoromethyl)-1H-pyrazol-1-yl]methyl}propyl (1S)-1-{[(2-pyridinylsulfonyl)amino]acetyl}pentylcarbamate;

(1S)-2,2-dimethyl-1-{[3-(trifluoromethyl)-1H-pyrazol-1-yl]methyl}propyl (1S)-1-methyl-2-oxo-3-[(2-pyridinylsulfonyl)amino]propylcarbamate;

(1S)-2,2-dimethyl-1-[5-(trifluoromethyl)-1,3-benzothiazol-2-yl]propyl (1S)-1-{[(2-pyridinylsulfonyl)amino]acetyl}pentylcarbamate;

(1S)-2,2-dimethyl-1-[5-(trifluoromethyl)-1,3-benzothiazol-2-yl]propyl (1S)-1-methyl-2-oxo-3-[(2-pyridinylsulfonyl)amino]propylcarbamate;

(1S)-2,2-dimethyl-1-({4-[4-(trifluoromethyl)phenyl]-1H-pyrazol-1-yl}methyl)propyl (1S)-1-{[(2-pyridinylsulfonyl)amino]acetyl}pentylcarbamate;

(1S)-2,2-dimethyl-1-({5-[4-(trifluoromethyl)phenyl]-1H-pyrazol-1-yl}methyl)propyl (1S)-1-{[(2-pyridinylsulfonyl)amino]acetyl}pentylcarbamate;

(1S)-2,2-dimethyl-1-{[3-(3-pyridinyl)-1H-pyrazol-1-yl]methyl}propyl (1S)-1-{[(2-pyridinylsulfonyl)amino]acetyl}pentylcarbamate;

(1S)-2,2-dimethyl-1-{[3-(4-pyridinyl)-1H-pyrazol-1-yl]methyl}propyl (1S)-1-{[(2-pyridinylsulfonyl)amino]acetyl}pentylcarbamate;

(1S)-1-[(5,6-dichloro-1H-benzimidazol-1-yl)methyl]-2,2-dimethylpropyl (1S)-1-{[(2-pyridinylsulfonyl)amino]acetyl}pentylcarbamate;

(1S)-1-[(5,6-dichloro-1H-benzimidazol-1-yl)methyl]-2,2-dimethylpropyl (1S)-1-methyl-2-oxo-3-[(2-pyridinylsulfonyl)amino]propylcarbamate;

(1S)-1-[(5,6-dichloro-1H-benzimidazol-1-yl)methyl]-2,2-dimethylpropyl 2-oxo-3-[(2-pyridinylsulfonyl)amino]propylcarbamate;

(1S)-2,2-dimethyl-1-({4-[4-(trifluoromethyl)phenyl]-1H-imidazol-1-yl}methyl)propyl (1S)-1-{[(2-pyridinylsulfonyl)amino]acetyl}pentylcarbamate; and (1S)-1-{[4-(1H-imidazol-1-yl)phenoxy]methyl}-2,2-dimethylpropyl (1S)-1-{[(2-pyridinylsulfonyl)amino]acetyl}pentylcarbamate.

Another embodiment of the present invention includes compounds of Formula (II):

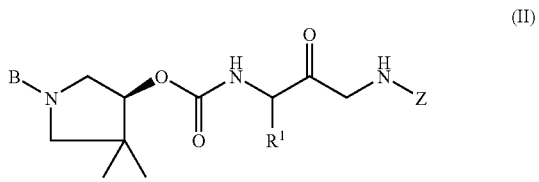

or a salt, solvate, or pharmaceutically functional derivative thereof, wherein B is $-(Q^1)_a-(Q^2)_b-(Q^3)$; further wherein $Q^1$ is C(O), S(O)$_2$, or CR$^2$R$^3$, where R$^2$ and R$^3$ each are independently selected from hydrogen or C$_1$–C$_6$ alkyl, and a is 0, 1, 2, or 3; Q$^2$ is O, S, NR$^2$, or CR$^2$R$^3$, where R$^2$ and R$^3$ each are independently selected from hydrogen or C$_1$–C$_6$ alkyl, and b is 0, 1, 2, or 3; and Q$^3$ is aryl, heteroaryl, heterocyclyl, aralkyl, or alkylene-heterocyclyl; R$^1$ is hydrogen or alkyl; Z is $-(X^1)_q-(X^2)$, wherein X$^1$ is S(O)$_2$, C(O), or alkyl, and q is 0 or 1; and X$^2$ is aryl, heteroaryl, or heterocyclyl.

Stereochemically, compounds of Formula (II) preferably are:

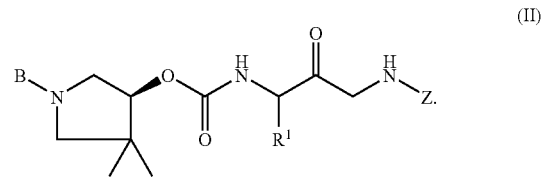

Further, preferably, a is 0; b is 0; and Q$^3$ is a heterocyclyl. More preferably, B is

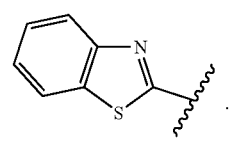

Preferably R$^1$ is hydrogen, methyl, or n-butyl. More preferably, R$^1$ is methyl or n-butyl. More preferably R$^1$ is n-butyl, more preferably R$^1$ is

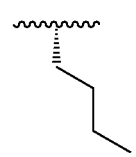

Preferably, Z is $-(X^1)_q-(X^2)$, where X$^1$ is S(O)$_2$; q is 1; and X$^2$ is heteroaryl. More preferably Z is

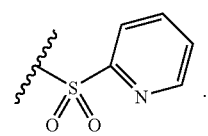

Another aspect of the present invention includes a pharmaceutical composition including a therapeutically effective amount of a compound of the present invention and one or more of a pharmaceutically acceptable carrier, diluent, or excipient.

Another aspect of the present invention includes a method for treating a disorder characterized by inappropriate capthesin K activity by administering to a mammal in need thereof a therapeutically effective amount of a compound of the present invention. Such method involves the treatment or prophylaxis of a disorder that is characterized by enhanced bone turnover that can ultimately lead to fracture through administration of an effective amount of a compound of the present invention.

Another aspect of the present invention includes a method for the preparation of a medicament for the treatment of a disorder, the disorder characterized by bone loss. Preferably, such method includes combining a compound of the present invention with one or more of a pharmaceutically acceptable carrier, diluent, or excipient.

Another aspect of the present invention includes a method for treating osteoporosis by administering to a mammal in need thereof a compound of the present invention. The method of treating osteoporosis can include administration of at least one bone building agent as well.

As used herein, the term "physiologically functional derivative" refers to any pharmaceutically acceptable derivative of a compound of the present invention; for example, an ester or an amide, which upon administration to a mammal is capable of providing (directly or indirectly) a compound of the present invention or an active metabolite thereof. Such derivatives will be clear to those skilled in the art, without undue experimentation, and with reference to the teaching of Burger's Medicinal Chemistry And Drug Discovery, $5^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula I or II), or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I) or formula (II). Representative salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexykesorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium, and valerate salts. Other salts, which are not pharmaceutically acceptable, may be useful in the preparation of compounds of this invention and these form a further aspect of the invention.

While it is possible that, for use in therapy, therapeutically effective amounts of a compound of formula (I) or formula (II), as well as salts, solvates and physiological functional derivatives thereof, may be administered as the raw chemical, it is possible to present the active ingredient as a pharmaceutical composition. Accordingly, the invention further provides pharmaceutical compositions that include therapeutically effective amounts of compounds of the formula (I) or (II) and salts, solvates and physiological functional derivatives thereof, and one or more pharmaceutically acceptable carriers, diluents, or excipients. The compounds of formula (I) or (II) and salts, solvates and physiologically functional derivatives thereof, are as described above. The carrier(s), diluent(s) or excipient(s) must be acceptable, in the sense of being compatible with the other ingredients of the formulation and not deleterious to the recipient of the pharmaceutical composition. In accordance with another aspect of the invention there is also provided a process for the preparation of a pharmaceutical formulation including admixing a compound of the formula (I) or (II), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, as a non-limiting example, 0.5 mg to 1 g of a compound of the formula (I) or (II), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate or solid polyethylene glycol can be added to the mixture before the encapsulation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials, and forcing through a screen. As an alternative to granulating, the powder mixture can be run through the tablet machine and the resulting imperfectly formed slugs can be broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers; preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) or (II) and salts, solvates and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) or (II) and salts, solvates and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for rectal administration may be presented as suppositories or as enemas.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors. For example, the age and weight of the animal, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) or (II) for the treatment of osteoporosis, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt or solvate, or physiologically functional derivative thereof, may be determined as a proportion of the effective amount of the compound of formula (I) or (II) per se. Similar dosages should be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in osteoporosis therapy, combination with other osteoporosis therapeutic agents is envisaged. Combination therapies according to the present invention thus comprise the administration of at least one compound of formula (I) or (II) or a pharmaceutically acceptable salt or solvate thereof, or a physiologically functional derivative thereof, and the use of at least one other osteoporosis treatment method. Preferably, combination therapies according to the present invention comprise the administration of at least one compound of formula (I) or (II) or a pharmaceutically acceptable salt or solvate thereof, or a physiologically functional derivative thereof, and at least one other osteoporosis treatment agent, preferably a bone building agent. The compound(s) of formula (I) or (II) and the other pharmaceutically active agent(s) may be administered together or separately and, when administered separately, this may occur simultaneously or sequentially in any order. The amounts of the compound(s) of formula (I) or (II) and the other pharmaceutically active agent(s) and the relative timings of administration will be selected in order to achieve the desired combined therapeutic effect. The administration in combination of a compound of formula (I) or (II) or salts, solvates, or physiologically functional derivatives thereof with other osteoporosis treatment agents may be in combination by administration concomitantly in (1) a unitary pharmaceutical composition including both compounds or (2) separate pharmaceutical compositions each including one of the compounds. Alternatively, the combination may be administered separately in a sequential manner wherein one osteoporosis treatment agent is administered first and the other second or vice versa. Such sequential administration may be close in time or remote in time.

A preferred additional osteoporosis treatment agent is a bone building (anabolic) agent. Bone building agents can lead to increases in parameters such as bone mineral density greater than those than can be achieved with anti-resorptive agents. In some cases, such anabolic agents can increase trabecular connectivity leading to greater structural integrity of the bone. A combination therapy composed of a bone forming agent with an anti-resorptive drug such as a cathepsin K inhibitor could provide even greater efficacy than treatment with either agent alone.

The present invention is directed to methods of regulating, modulating, or inhibiting cathepsin K for the prevention and/or treatment of disorders related enhanced bone turnover, which can ultimately lead to fracture. In particular, the compounds of the present invention can also be used in the treatment of osteoporosis. Furthermore, the compounds of the present invention can be used to provide additive or synergistic effects with existing osteoporosis therapies.

The present invention thus also provides compounds of formula (I) or (II) and pharmaceutically acceptable salts or solvates thereof, or physiologically functional derivatives thereof, for use in medical therapy, and particularly in the treatment of disorders mediated by enhanced bone turnover which can ultimately lead to fracture.

The present invention also provides compounds of formula (I) or (II) and pharmaceutically acceptable salts or solvates thereof, or physiologically functional derivatives thereof, for use in medical therapy, and particularly in the treatment of disorders characterized by bone loss or characterized by excessive cartilage or matrix degradation.

The compounds of the present invention are also useful in the treatment of one or more diseases afflicting mammals that are characterized by potential involvement of cathepsin K in autoimmune diseases such as rheumatoid arthritis, osteoathritis, neoplastic diseases, parasitic diseases, and atherosclerosisis.

A further aspect of the invention provides a method of treatment of a mammal suffering from a disorder mediated by enhanced bone turnover that can ultimately lead to fracture, which includes administering to said subject an effective amount of a compound of formula (I) or (II) or a pharmaceutically acceptable salt, solvate, or a physiologically functional derivative thereof.

A further aspect of the invention provides a method of treatment of a mammal suffering from a disorder characterized by bone loss, which includes administering to said subject an effective amount of a compound of formula (I) or (II) or a pharmaceutically acceptable salt, solvate, or a physiologically functional derivative thereof. In a preferred embodiment, the disorder is osteoporosis.

A further aspect of the invention provides a method of treatment of a mammal suffering from osteoporosis, which includes administering to said subject an effective amount of a compound of formula (I) or (II) or a pharmaceutically acceptable salt or solvate thereof, or a physiologically functional derivative thereof.

A further aspect of the present invention provides the use of a compound of formula (I) or (II), or a pharmaceutically acceptable salt or solvate thereof, or a physiologically functional derivative thereof, in the preparation of a medicament for the treatment of a disorder characterized by enhanced bone turnover that can ultimately lead to fracture. In a preferred embodiment, the disorder is osteoporosis.

A further aspect of the present invention provides the use of a compound of formula (I) or (II), or a pharmaceutically acceptable salt or solvate thereof, or a physiologically functional derivative thereof, in the preparation of a medicament for the treatment of a disorder characterized by bone loss. In a preferred embodiment, the disorder is osteoporosis. A further aspect of the present invention provides the use of a compound of formula (I) or (II), or a pharmaceutically acceptable salt or solvate thereof, or a physiologically functional derivative thereof, in the preparation of a medicament for the treatment of osteoporosis. In another embodiment, therapeutically effective amounts of the compounds of formula (I) or (II) or salts, solvates or physiologically derived derivatives thereof and at least one bone building agent may be administered in combination to a mammal for treatment of osteoporosis.

The mammal requiring treatment with a compound of the present invention is typically a human being.

The compounds of this invention may be made by a variety of methods, including standard synthetic methods. Any previously defined variable will continue to have the previously defined meaning unless otherwise indicated. Illustrative general synthetic methods are set out below and then specific compounds of the invention are prepared in the working Examples.

Compounds of general formula (I) or formula (II) may be prepared by methods known in the art of organic synthesis as set forth in part by the following synthetic schemes. Generally, the following schemes are illustrated using compounds of formula (I), but it is recognized that such schemes are easily adaptable by the skilled artisan to prepare other compounds of formula (II). It is also recognized that in all of the schemes described below, it is well understood that protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I) or (II). Those skilled in the art will recognize if a stereocenter exists in compounds of formula (I) or (II). Accordingly, the present invention includes all possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of formula (I) and (II), can be prepared according to the synthetic sequences shown in Schemes I and II, which are further detailed in the Examples section following.

Scheme I

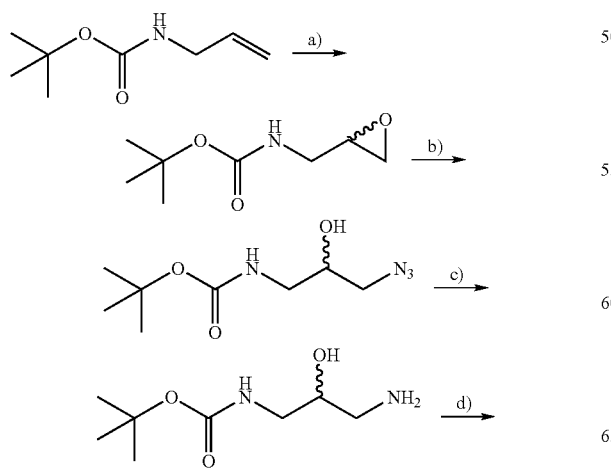

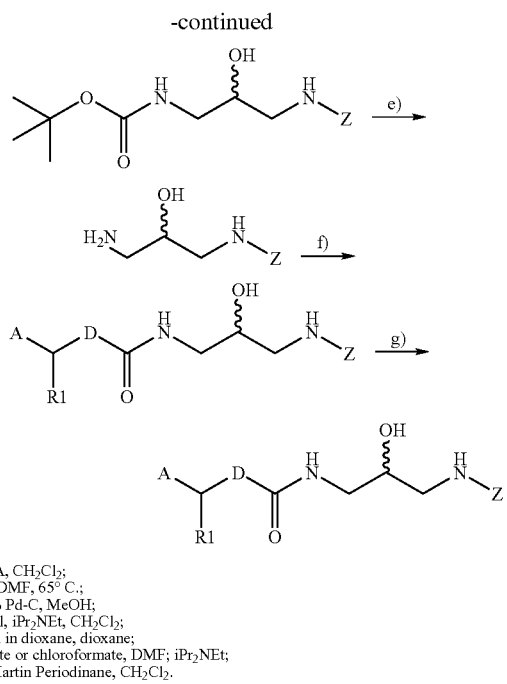

a) mCPBA, CH$_2$Cl$_2$;
b) NaN$_3$, DMF, 65° C.;
c) H$_2$/10% Pd-C, MeOH;
d) RSO$_2$Cl, iPr$_2$NEt, CH$_2$Cl$_2$;
e) 4N HCl in dioxane, dioxane;
f) carbonate or chloroformate, DMF; iPr$_2$NEt;
g) Dess-Martin Periodinane, CH$_2$Cl$_2$.

Scheme II

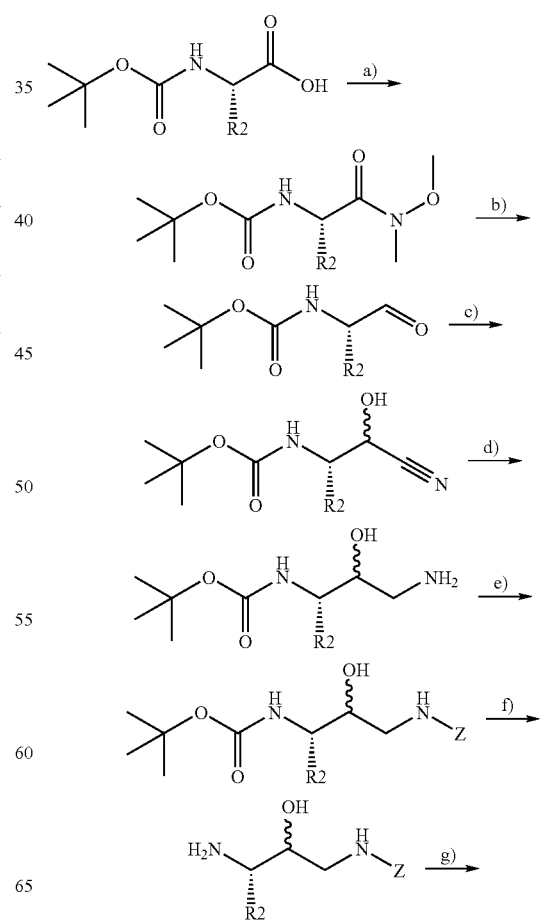

-continued

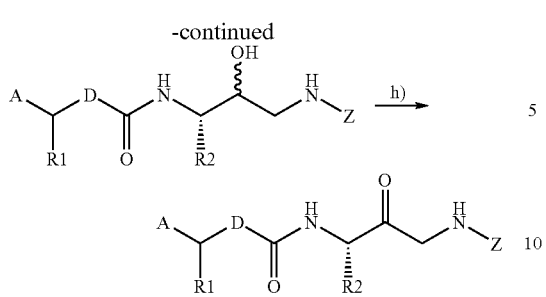

a) carbonyl diimidazole, NEt₃, MeNHOMe·HCl, CH₂Cl₂, 0° C. to rt;
b) 1 M LAH in THF, THF, 0° C. to rt;
c) KCN, HOAc, MeOH;
d) H₂/PtO₂-C, HOAc;
e) sulfonyl chloride or carbamoyl chloride, NaHCO₃, CH₂Cl₂, H₂O;
f) 4N HCl in dioxane, dioxane;
g) carbonate or chloroformate, DMF; iPr₂NEt;
h) Dess-Martin Periodinane, CH₂Cl₂.

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used throughout the present specification:

g (grams);
L (liters);
μL (microliters);
M (molar);
h (hour(s));
MHz (megahertz);
mmol (millimoles);
min (minutes);
mp (melting point);
T$_r$ (retention time);
MeOH (methanol);
TEA (triethylamine);
TFAA (trifluoroacetic anhydride);
DMSO (dimethylsulfoxide);
DME (1,2-dimethoxyethane);
DCE (dichloroethane);
mg (milligrams);
mL (milliliters);
psi (pounds per square inch);
mM (millimolar);
Hz (Hertz);
mol (moles);
RT (room temperature);
TLC (thin layer chromatography);
RP (reverse phase);
i-PrOH (isopropanol);
TFA (trifluoroacetic acid);
THF (tetrahydrofuran);
EtOAc (ethyl acetate);
DCM (dichloromethane);
DMF (NN-dimethylformamide);
DMPU (N,N'-dimethylpropyleneurea);
IBCF (isobutyl chloroformate);
HOSu (N-hydroxysuccinimide);
mCPBA (meta-chloroperbenzoic acid);
EDC (ethylcarbodiimide hydrochloride);
BOC (tert-butyloxycarbonyl);
DCC (dicyclohexylcarbodiimide);
Ac (acetyl);
TMSE (2-(trimethylsilyl)ethyl);
TIPS (triisopropylsilyl);
DMAP (4-dimethylaminopyridine);
HPLC (high pressure liquid chromatography);
BOP (bis(2-oxo-3-oxazolidinyl)phosphinic chloride);
TBAF (tetra-n-butylammonium fluoride);
Et (ethyl);
CDI (1,1-carbonyldiimidazole);
HOAc (acetic acid);
HOBT (1-hydroxybenzotriazole);
FMOC (9-fluorenylmethoxycarbonyl);
CBZ (benzyloxycarbonyl);
atm (atmosphere);
TMS (trimethylsilyl);
TBS (t-butyldimethylsilyl);
Me (methyl);
tBu (tert-butyl).

All references to ether are to diethyl ether; brine refers to a saturated aqueous solution of NaCl. Unless otherwise indicated, all temperatures are expressed in degrees Centigrade (°C.). All reactions were conducted under an inert atmosphere at room temperature unless otherwise noted.

¹H-NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated by: s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510

FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid, iodine, iodoplatinate(potassium), permanganate(potassium), or p-anisaldehyde solution. Flash column chromatography was performed on silica gel (230–400 mesh, Merck). Optical rotations were obtained using a Perkin Elmer Model 241 Polarimeter. Melting points were determined using a Mel-Temp II apparatus and are uncorrected.

The following examples describe the syntheses of compounds of Formula (I) and (II) as well as intermediates particularly useful in the synthesis of compounds of Formula (I) and (II):

Example 1

Preparation of (1S)-2,2-dimethyl-1-({3-[4-(trifluoromethyl)phenyl]-1H-pyrazol-1-yl}methyl)propyl 2-oxo-3-[(2-pyridinylsulfonyl)amino]propylcarbamate

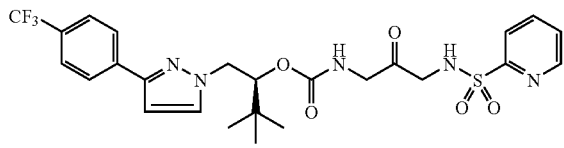

Example 1a

Preparation of (S)-2-hydroxy-3,3-dimethylbutanoic Acid

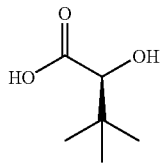

To a solution of 30.0 g (0.229 mol) of L-tert-leucine in 345 mL of 1 N sulfuric acid, cooled to 0° C., was added over 2 h a solution of 23.7 g (0.343 mol) of sodium nitrite in 83 mL of water. The temperature was maintained below 5° C. during the addition, and the mixture was then refrigerated for 24 h. The solution was then extracted with 150 mL of ether (3×) and the extract was washed with 100 mL of saturated aqueous sodium chloride. The extract was dried over anhydrous magnesium sulfate, filtered, and concentrated to afford 19.5 g (65%) of a pale yellow oil. The crude product was taken to the next step. $^1$H-NMR (300 MHz, CDCl$_3$): δ 3.91 (s, 1H), 1.01 (s, 9H).

Example 1b

Preparation of (2S)-3,3-dimethyl-1,2-butanediol

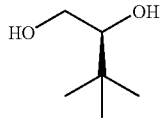

To a solution of 18.0 g (0.136 mol) of (S)-2-hydroxy-3,3-dimethylbutanoic acid in 150 mL of ether, cooled to 0° C., was added 272 mL (272 mmol) of a 1.0 M solution of lithium aluminum hydride in tetrahydrofuran over a period of 30 min. The reaction mixture was then warmed to room temperature and stirred for 16 h. To the reaction mixture was added 100 mL of 50% concentrated hydrochloric acid. The layers were separated, the aqueous layer was extracted with 200 mL of ether (3×), and the extract was dried over anhydrous magnesium sulfate. After filtration and concentration, the crude product was purified by column chromatography on silica gel with hexane:ethyl acetate (1:9) as the eluent to afford 10.2 g (63%) of (2S)-3,3-dimethyl-1,2-butanediol as a colorless solid. $^1$H-NMR (300 MHz, CDCl$_3$): δ 3.74 (dd, J=10 Hz, J=3 Hz, 1H), 3.48 (t, J=10 Hz, 1H), 3.36 (dd, J=10 Hz, J=3 Hz, 1H), 2.70 (br s, 2H), 0.91 (s, 9H).

Example 1c

Preparation of (2S)-2-hydroxy-3,3-dimethylbutyl 4-methylbenzenesulfonate

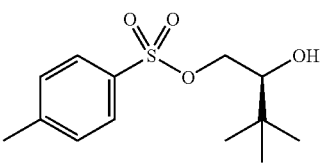

To 6.65 g (56 mmol) of (2S)-3,3-dimethyl-1,2-butanediol in 13 mL of pyridine at 0° C. was added dropwise a solution of 10.68 g (56 mmol) of p-toluenesulfonyl chloride in 20 mL of pyridine. The solution was maintained at 0° C. for 5 h and then let warm to ambient temperature. After being stirred overnight, the mixture was concentrated, and the residue was taken up in 200 mL of diethyl ether. The ether solution was washed with 50 mL of 1N hydrochloric acid, 50 mL of saturated aqueous sodium bicarbonate, and 50 mL of water, dried over anhydrous magnesium sulfate, and concentrated. The residue was purified by silica gel chromatography eluting with ethyl acetate:hexanes (3.5:6.5) to give 13 g (85%) of (2S)-2-hydroxy-3,3-dimethylbutyl 4-methylbenzenesulfonate. $^1$H-NMR (300 MHz, DMSO-d$_6$): δ 7.79 (d, J=8 Hz, 2H), 7.47 (d, J=8 Hz, 2H), 5.11 (br s, 1H), 4.08 (dd, J=10 Hz, J=3 Hz, 1H), 3.76 (dd, J=10 Hz, J=8 Hz, 1H), 3.23 (d, J=8 Hz, 1H), 2.41 (s, 3H), 0.76 (s, 9H). ES-LCMS m/z 273 (M+H), 295 (M+Na).

Example 1d

Preparation of (S)-3,3-dimethyl-1,2-epoxybutane

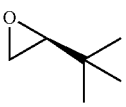

To 20.05 g (73.7 mmol) of (2S)-2-hydroxy-3,3-dimethylbutyl 4-methylbenzenesulfonate in 300 mL of methanol at 0° C. was added dropwise 75.2 mL (75.2 mmol) of 1M sodium hydroxide, and the mixture was stirred for 30 min. It was then diluted with 10 mL of saturated potassium dihydrogen phosphate, and poured into 1400 mL of water. The mixture was extracted three times with 50 mL of pentane. The extracts were combined and dried over anhydrous magnesium sulfate, and the pentane was distilled off to afford 7.94 g (83%) of (S)-3,3-dimethyl-1,2-epoxybutane with 0.4 mole equivalents of residual pentane. $^1$H-NMR (300 MHz, DMSO-d$_6$): δ 2.69 (dd, J=4 Hz, J=3 Hz, 1H), 2.52–2.57 (m, 2H), 0.85 (s, 9H).

Example 1e

Preparation of
3-[4-(Trifluoromethyl)phenyl]-1H-pyrazole

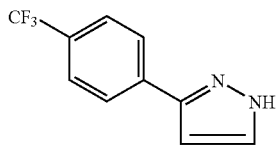

First, 3.18 g (79.4 mmol) of a 60% sodium hydride suspension in mineral oil was added in portions to a solution of 9.96 g (52.9 mmol) of 4-trifluoromethylacetophenone and 12.6 mL (158.76 mmol) of ethyl formate in 75 mL of anhydrous tetrahydrofuran at 0° C. The mixture was allowed to reach ambient temperature, at which an exothermic reaction occurred, which subsided in 5 min. After 1 h, the mixture was concentrated and the residue was triturated with diethyl ether to provide a tan solid in two crops. The solid was suspended in 1N hydrochloric acid and the resulting bright yellow solid was filtered and washed with water. The solid was dissolved in 150 mL of methanol and stirred at room temperature with 4.7 mL (96.9 mmol) of hydrazine hydrate for 3 h. Solvent was evaporated and the resulting solid was suspended in water, stirring for 18 h. The solid was filtered, washed with water, and dried under vacuum to provide 8.9 g (80%) of 3-[4-(trifluoromethyl)phenyl]-1H-pyrazole as a yellow solid. $^1$H-NMR (DMSO-$d_6$): δ 13.05 (br s, 1H), 7.99 (d, J=8 Hz, 2H), 7.8 (br s, 1H), 7.71 (d, J=8 Hz, 2H), 6.81 (s, 1H); ES-LCMS m/z 213 (M+H).

Example 1f

Preparation of (2S)-3,3-Dimethyl-1-{3-[4-(trifluoromethyl)phenyl]-1H-pyrazol-1-yl}-2-butanol

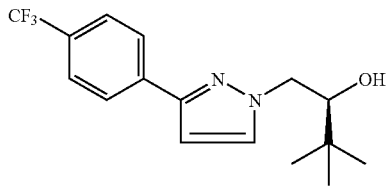

A mixture of 4.11 g (19.4 mmol) of 3-[4-(trifluoromethyl) phenyl]-1H-pyrazole, 2.0 g (19.9 mmol) of (S)-3,3-dimethyl-1,2-epoxybutane, 3.1 mL (22.3 mmol) of triethylamine, and 10 mL of isopropyl alcohol was placed in a sealed tube and heated at 85° C. for 48 h. Solvent was evaporated and the residue was purified by silica gel chromatography eluting with ethyl acetate:hexanes (1:7) to give 2.92 g (49%) of (2S)-3,3-dimethyl-1-{3-[4-(trifluoromethyl) phenyl]-1H-pyrazol-1-yl}-2-butanol as a pale yellow solid and 0.4 g (7%) of its isomer (2S)-3,3-dimethyl-1-{5-[4-(trifluoromethyl)phenyl]-1H-pyrazol-1-yl}-2-butanol. Data for (2S)-3,3-dimethyl-1-{3-[4-(tifluoromethyl)phenyl]-1H-pyrazol-1-yl}-2-butanol: $^1$H-NMR (DMSO-$d_6$): δ 7.96 (d, J 8 Hz, 2H), 7.75 (s, 1H), 7.69 (d, J=8 Hz, 2H), 6.76 (d, J=2 Hz, 1H), 4.86 (d, J=6 Hz, 1H), 4.26 (dd, J=14 Hz, J=2 Hz, 1H), 3.88 (dd, J=14 Hz, J=10 Hz, 1H), 3.45–3.50 (m, 1H), 0.88 (s, 9H); ES-LCMS m/z 313 (M+H). Data for (2S)-3,3-dimethyl-1-{5-[4-(trifluoromethyl)phenyl]-1H-pyrazol-1-yl}-2-butanol: $^1$H-NMR (DMSO-$d_6$): δ 7.87 (d, J=8 Hz, 2H), 7.80 (d, J=8 Hz, 2H), 7.52 (d, J=2 Hz, 1H), 6.42 (d, J=2 Hz, 1H), 5.01 (d, J=6 Hz, 1H), 4.10 (dd, J=14 Hz, J=2 Hz, 1H), 3.92 (dd, J=14 Hz, J=10 Hz, 1H), 3.62–3.67 (m, 1H), 0.82 (s, 9H); ES-LCMS m/z 313 (M+H).

Example 1g

Preparation of (1 S)-2,2-Dimethyl-1-({3-[4-(trifluoromethyl)phenyl-]1H-pyrazol-1-yl}methyl)propyl 4-nitrophenyl Carbonate

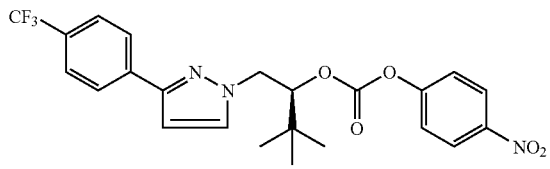

To a solution of 2.56 g (8.19 mmol) of (2S)-3,3-dimethyl-1-{3-[4-(trifluoromethyl)phenyl]-1H-pyrazol-1-yl}-2-butanol and 1.54 g (19.6 mmol) of pyridine in 29 mL of anhydrous dichloromethane was added 1.98 g (9.83 mmol) of p-nitrophenyl chloroformate. The mixture was stirred at ambient temperature for 18 h. It was washed with 5% citric acid and then stirred with ammonium hydroxide:water (1:4) for 15 min. The organic phase was washed with sodium bicarbonate:water, dried with sodium sulfate, and concentrated to provide 3.7 g (94%) of (1S)-2,2-Dimethyl-1-({3-[4-(trifluoromethyl)phenyl]-1H-pyrazol-1-yl}methyl)propyl-4-nitrophenylcarbonate as a pale yellow solid. $^1$H-NMR (DMSO-$d_6$): δ 8.10 (d, J=9 Hz, 2H), 7.97 (d, J=8 Hz, 2H), 7.91, (d, J=2 Hz, 1H), 7.70 (d, J=8 Hz, 2H), 7.21 (d, J=9 Hz, 2H), 6.85 (d, J=2 Hz, 1H), 4.87 (dd, J=10 Hz, J=2 Hz, 1H), 4.61 (dd, J=14 Hz, J=2 Hz, 1H), 4.33 (dd, J=14 Hz, J=10 Hz, 1H), 1.02 (s, 9H); ES-LCMS m/z 478 (M+H).

Example 1h

Preparation of tert-butyl 2-oxiranylmethylcarbamate

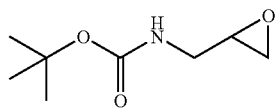

To a solution of 28.9 g (184 mmol) of tert-butyl allylcarbamate in 400 mL of dichloromethane was added 103 g (460 mmol) of 77% 3-chloroperoxybenzoic acid at room temperature. The reaction mixture was stirred at room temperature overnight. The solid was filtered and the filtrate was concentrated. The residue was taken up in diethyl ether and washed with 5% sodium hydrosulfite (3×), saturated sodium bicarbonate (3×), brine (3×), and dried over anhydrous magnesium sulfate. Removal of solvent gave 21 g (66%) of tert-butyl 2-oxiranylmethylcarbamate as a liquid. $^1$H-NMR (400 MHz, CDCl$_3$): δ 4.73 (br s, 1H), 3.53 (br s, 1H), 3.21 (m, 1H), 3.08 (br s, 1H), 2.77 (t, J=4 Hz, 1H), 2.58 (m, 1H), 1.43 (s, 9H).

Example 1i

Preparation of tert-butyl 2-hydroxy-3-[(2 pyridinylsulfonyl)amino]propylcarbamate

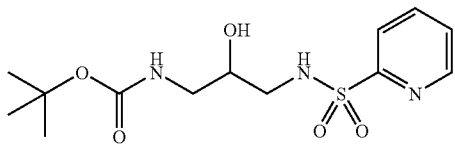

First, 21 g (121 mmol) of tert-butyl 2-oxiranylmethylcarbamate was dissolved in 90 mL of dimethylformamide and 11.8 g (182 mmol) of sodium azide was added. The reaction mixture was stirred at 65° C. overnight. The dimethylformamide was removed and ether was added. The ether layer was washed with brine (3×), dried over anhydrous magnesium sulfate, and concentrated. The residue was dissolved in 50 mL of methanol and hydrogenated with 2 g of 10% palladium on carbon under 45 psi of hydrogen gas at room temperature overnight. The catalyst was removed by filtration and the filtrate was concentrated. The residue was dissolved in 30 mL of dichloromethane, and 17.7 mL (17.7 mmol) of 1M 2-pyridinylsulfonyl chloride in dichloromethane and 3.8 mL (21.8 mmol) of N,N-diisopropylethylamine were added. The reaction mixture was stirred at room temperature overnight. After removal of solvent, purification by column chromatography with hexane:ethyl acetate (1:2) as eluant gave 350 mg (0.9%) of tert-butyl 2-hydroxy-3-[(2-pyridinylsulfonyl)amino]propylcarbamate. $^1$H-NMR (300 MHz CDCl$_3$): δ 8.72 (d, J=6 Hz, 1H), 8.05 (d, J=8 Hz, 1H), 7.97 (t, J=8 Hz, 1H), 7.55 (m, 1H), 6.10 (br s, 1H), 5.11 (br s, 1H), 4.33 (d, J=5 Hz, 1H), 3.81 (m, 1H), 3.36–3.20 (m, 4H), 1.44 (s, 9H). ES-LCMS: 332 (M+H).

Example 1j

Preparation of (1S)-2,2-dimethyl-1-({3-[4-(trifluoromethyl)phenyl]-1H-pyrazol-1-yl}methyl)propyl 2-oxo-3-[(2-pyridinylsulfonyl)amino]propyl carbamate To 78.7 mg (237.7 μmol) of tert-butyl 2-hydroxy-3-[(2-pyridinylsulfonyl)amino]propylcarbamate in 2.4 mL of dioxane at room temperature was added 3.0 mL (11.88 mmol) of a 4 M solution of hydrogen chloride in dioxane. The mixture was stirred for 2 h, concentrated, and dried under vacuum. The residue was then dissolved in 2.0 mL of dimethylformamide. This solution was added to 108.1 mg (226.4 μmol) of 4-nitrophenyl (1S)-2,2-dimethyl-1-{[3-(trifluoromethyl)-1H-pyrazol-1-yl]methyl}propyl carbonate in 2.5 mL of dimethylformamide. This was followed by the addition of 157.8 μL (905.7 μmol) of N,N-diisopropylethylamine, and the reaction mixture was stirred for 16 h at room temperature. The solution was concentrated, saturated sodium bicarbonate was added, and the resulting mixture was extracted with ethyl acetate. The organic layer was washed with saturated sodium chloride, dried over anhydrous magnesium sulfate, filtered, and concentrated. The residue was purified by silica gel column chromatography eluting with an ethyl acetate:hexanes solution (7:3) to give 90.8 mg (63%) of a mixture of alcohols. The alcohols were dissolved in 3.7 mL of dichloromethane at room temperature and 97.4 mg (229.8 μmol) of Dess-Martin periodinane was added. The reaction mixture was stirred for 120 min, and then poured into saturated sodium metabisulfite. Following subsequent neutralization with saturated sodium bicarbonate, the mixture was extracted with ethyl acetate. The organic layer was dried over anhydrous magnesium sulfate, filtered, and concentrated. The residue was purified by silica gel column chromatography eluting with an ethyl acetate:hexanes solution (4:1). The sample was further purified by HPLC using a Waters Symmetry C18 19 mm×150 mm column with 7 μm packing eluted with a five minute gradient of 30%-70% acetonitrile in water. The mobile phase contained a 0.1% trifluoroacetic acid modifier. This purification gave 29.0 mg (28%) of (1S)-2,2-dimethyl-1-({3-[4-(trifluoromethyl)phenyl]-1H-pyrazol-1-yl}methyl)propyl-2-oxo-3-[(2-pyridinylsulfonyl)amino]propylcarbamate. R$_f$=0.35 (4:1 ethyl acetate:hexanes); $^1$H-NMR (300 MHz, DMSO-d$_6$): δ 8.65 (d, J=5 Hz, 1H), 8.20 (s, 1H), 8.03 (t, J=8 Hz, 1H), 7.96 (d, J=8 Hz, 2H), 7.88 (d, J=8 Hz, 1H), 7.76 (s, 1H), 7.69 (d, J=8 Hz, 2H), 7.60 (dd, J=8 Hz, J=5 Hz, 1H), 6.91 (br s, 1H), 6.70 (d, J=2 Hz, 1H), 4.85 (d, J=6 Hz, 1H), 4.45 (d, J=11 Hz, 1H), 4.20(dd, J=14 Hz, J=8 Hz, 1H), 3.94(d, J=6 Hz, 2H), 3.85 (d, J=5 Hz, 2H), 0.97 (s, 9H); HRMS C$_{25}$H$_{29}$F$_3$N$_5$O$_5$S m/z 568.1842 (M+H)$_{cal}$; 568.1873 (M+H)$_{Obs}$.

Example 2

Preparation of (1S)-2,2-dimethyl-1-({3-[4-(trifluoromethyl)phenyl-]1H-pyrazol-1-yl}methyl)propyl (1S)-1-methyl-2-oxo-3-[(2-pyridinylsulfonyl)amino] propylcarbamate

Example 2a

Preparation of tert-butyl (1S)-1-methyl-2-oxoethylcarbamate

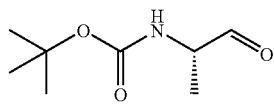

To a solution of 10.7 g (57.0 mmol) of (2S)-2-[(tert-butoxycarbonyl)amino]propanoic acid in 200 mL of dichloromethane at 0° C. was added 12.0 g (74.1 mmol) of carbonyldiimidazole, 10.39 mL (74.1 mmol) of triethylamine, and 7.08 g (74.1 mmol) of N,O-dimethylhydroxylamine hydrochloride. The reaction mixture was warmed to room temperature and left stirring for 16 h. Diethyl ether was then added, followed by the addition of 10% hydrochloric acid. The layers were separated, and the organic layer was then washed with saturated sodium bicarbonate solution, dried over anhydrous magnesium sulfate and concentrated under vacuum to afford 7.05 g of the crude product. Then, 7.05 g (30.4 mmol) of the crude tert-butyl (1S)-2-[methoxy(methyl)amino]-1-methyl-2-oxoethylcarbamate was dissolved in 109 mL of tetrahydrofuran and cooled to 0° C. A 1.0 M solution of 45.6 mL (45.6 mmol) of lithium aluminum hydride in tetrahydrofuran was then added gradually over 20 min. After stirring for 30 min, 10% citric acid solution was added. and the reaction mixture was stirred for another 5 min. The reaction mixture was diluted with diethyl ether and the layers were separated. The organic layer was dried over anhydrous magnesium sulfate and concentrated under vacuum to afford 5.25 g (>99%) of tert-butyl (1S)-1-methyl-2-oxoethylcarbamate, which was carried into the next step directly. $^1$H-NMR (300 MHz, CDCl$_3$) δ 9.58 (s, 1H), 5.15 (m, 1H), 4.25 (m, 1H), 1.35 (s, 9H), 1.27 (d, J=7 Hz, 3H).

Example 2b

Preparation of tert-butyl (1S,2S)-3-amino-2-hydroxy-1-methylpropylcarbamate & tert-butyl (1S,2R)-3-amino-2-hydroxy-1-methylpropylcarbamate

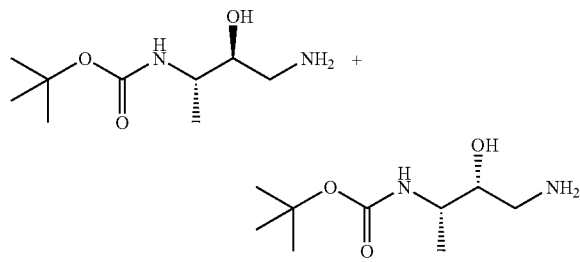

To a solution of 5.25 g (30.4 mmol) of tert-butyl (1S)-1-methyl-2-oxoethylcarbamate in 30 mL of methanol at 0° C. was added 2.18 g (33.4 mmol) of potassium cyanide, followed by 1.74 mL (33.4 mmol) of acetic acid. The reaction mixture was warmed to room temperature, left stirring for 16 h, and then filtered and concentrated under vacuum. The residue was dissolved in 80 mL of acetic acid, and 0.8 g of platinum oxide on carbon was added. The reaction mixture was then stirred under 40 psi of hydrogen for 4 h. The catalyst was filtered off over celite, and the filtrate was washed with methanol and concentrated to afford 3.06 g (49%) of tert-butyl (1S,2S)-3-amino-2-hydroxy-1-methylpropylcarbamate & tert-butyl (1S,2R)-3-amino-2-hydroxy-1-methylpropylcarbamate. $^1$H-NMR (300 MHz, DMSO-d$_6$): δ 6.74, 6.59 (d, J=8 Hz, 1H), 3.61–3.38 (m, 3H), 2.80 (m, 1H), 2.51 (m, 2H), 1.45 (br s, 1H), 1.38 (s, 9H), 0.97 (m, 3H). GC-MS m/z 205 (M+H).

Example 2c

Preparation of tert-butyl (1S,2S)-2-hydroxy-1-methyl-3-[(2-pyridinylsulfonyl)amino]propylcarbamate & tert-butyl (1S,2R)-2-hydroxy-1-methyl-3-[(2-pyridinylsulfonyl)amino]propylcarbamate

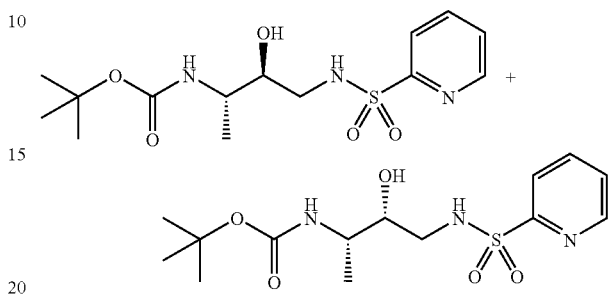

To a solution of 3.06 g (15.0 mmol) of tert-butyl (1S,2S)-3-amino-2-hydroxy-1-methylpropylcarbamate & tert-butyl (1S,2R)-3-amino-2-hydroxy-1-methylpropylcarbamate in 100 mL of dichloromethane was added 3.78 g (45.0 mmol) of sodium bicarbonate and 50 mL of water. The reaction mixture was cooled to 0° C. and 16.5 mL (16.5 mmol) of a 1.0 M solution of 2-pyridinesulfonyl chloride in dichloromethane was added gradually over 20 min. The reaction mixture was stirred at room temperature for 16 h. The layers were then separated and the organic layer was dried over anhydrous magnesium sulfate, and concentrated under vacuum to afford the crude product. This product was purified via silica gel chromatography eluting with ethyl acetate:hexane (8:2) to afford 2.0 g (34%) of tert-butyl (1S,2S)-2-hydroxy-1-methyl-3-[(2-pyridinylsulfonyl)amino]propylcarbamate & tert-butyl (1S,2R)-2-hydroxy-1-methyl-3-[(2-pyridinylsulfonyl)amino]propylcarbamate as a pale yellow oil. $^1$H-NMR (300 MHz, CDCl$_3$): δ 8.72 (m, 1H), 8.07–7.92 (m, 2H), 7.51 (m, 1H), 6.25, 6.08 (2br s, 1H), 4.83-4.64 (m, 2H), 3.74–3.47 (m, 3H), 3.27–3.19 (m, 1H), 1.23, 1.22 (2s, 9H), 1.12 (m, 3H).

Example 2d

Preparation of (1S)-2,2-dimethyl-1-({3-[4-(trifluoromethyl)phenyl]-1H-pyrazol-1-yl}methyl)propyl (1S,2S)-2-hydroxy-1-methyl-3-[(2-pyridinylsulfonyl)amino]propylcarbamate & (1S)-2,2-dimethyl-1-({3-[4-(trifluoromethyl)phenyl]-1H-pyrazol-1-yl}methyl)propyl (1S,2R)-2-hydroxy-1-methyl-3-[(2-pyridinylsulfonyl)amino]propylcarbamate

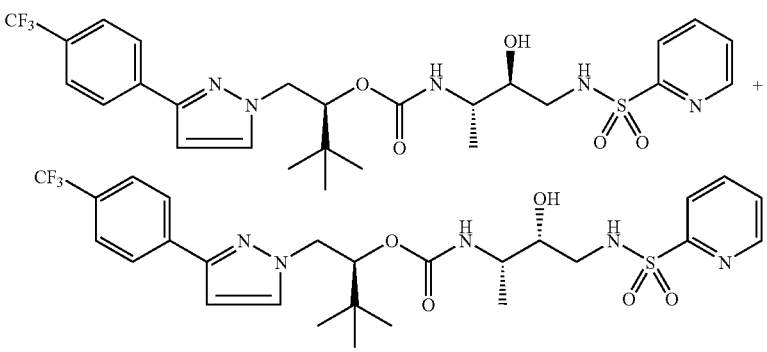

To a solution of 0.101 g (0.29 mmol) of tert-butyl (1S,2S)-2-hydroxy-1-methyl-3-[(2-pyridinylsulfonyl)amino]propylcarbamate & tert-butyl (1S,2R)-2-hydroxy-1-methyl-3-[(2-pyridinylsulfonyl)amino]propylcarbamate in 2 mL of dioxane was added 2.0 mL of a 4.0 M solution of hydrochloric acid in dioxane. The reaction mixture was stirred for 30 min, and then concentrated. This residue was dissolved in 3.0 mL of dimethylformamide and this solution was added to 0.14 g (0.29 mmol) of (1S)-2,2-dimethyl-1-({3-[4-(trifluoromethyl)phenyl]-1H-pyrazol-1-yl}methyl)propyl 4-(nitro)phenyl carbonate and 1.5 mL (0.87 mmol) of diisopropylethylamine. The reaction mixture was stirred at room temperature for 16 h. A saturated solution of sodium bicarbonate was then added, followed by diethyl ether. The layers were separated, and the organic layer was dried over anhydrous magnesium sulfate, and concentrated under vacuum to afford the crude product. This crude product was purified via silica gel chromatography eluting with ethyl acetate:hexane (1:1) to afford 0.138 g (81%) of (1S)-2,2-dimethyl-1-({3-[4-(trifluoromethyl)phenyl]-1H-pyrazol-1-yl}methyl)propyl (1S,2S)-2-hydroxy-1-methyl-3-[(2-pyridinylsulfonyl)amino]propylcarbamate & (1S)-2,2-dimethyl-1-({3-[4-(trifluoromethyl)phenyl]-1H-pyrazol-1-yl}methyl)propyl (1S,2R)-2-hydroxy-1-methyl-3-[(2-pyridinylsulfonyl)amino]propylcarbamate as a colorless oil. $^1$H-NMR (300 MHz, CDCl$_3$): δ 8.64 (m, 1H), 7.98–7.88 (m, 5H), 7.64–7.47 (m, 4H), 6.60 (s, 1H), 5.01–4.81 (m, 3H), 4.46, 4.42 (2s br, 1H), 4.25–4.17 (m, 2H), 3.59–3.44 (m, 2H), 3.14 (m, 1H), 1.00 (m, 12H); LC-MS 584 (M+H).

Example 2e

Preparation of (1S)-2,2-dimethyl-1-({3-[4-(trifluoromethyl)phenyl]-1H-pyrazol-1-yl}methyl)propyl (1S)-1-methyl-2-oxo-3-[(2-pyridinylsulfonyl)amino]propylcarbamate To a solution of 0.130 g (0.22 mmol) of (1S)-2,2-dimethyl-1-({3-[4-(trifluoromethyl)phenyl]-1H-pyrazol-1-yl}methyl)propyl (1S,2S)-2-hydroxy-1-methyl-3-[(2-pyridinylsulfonyl)amino]propylcarbamate & (1S)-2,2-dimethyl-1-({3-[4-(trifluoromethyl)phenyl]-1H-pyrazol-1-yl}methyl)propyl (1S,2R)-2-hydroxy-1-methyl-3-[(2-pyridinylsulfonyl)amino]propylcarbamate in 2.0 mL of dichloromethane was added 0.020 g (0.24 mmol) of sodium bicarbonate and 0.11 g (0.26 mmol) of Dess-Martin periodinane. The reaction mixture was stirred for 15 min and then purified via silica gel chromatography eluting with ethyl acetate:hexane (7:3) to afford 0.078 g (59%) of (1S)-2,2-dimethyl-1-({3-[4-(trifluoromethyl)phenyl]-1H-pyrazol-1-yl}methyl)propyl(1S)-1-methyl-2-oxo-3-[(2-pyridinylsulfonyl)amino]propylcarbamate as a colorless oil. $^1$H-NMR (300 MHz, CDCl$_3$) δ 8.58 (m, 1H), 7.98–7.89 (m, 4H), 7.63 (m, 2H), 7.46 (m, 2H), 6.65 (s, 1H), 5.56 (m, 1H), 1.05 (s, 9H), 5.24 (d, J=7 Hz, 1H), 4.98 (m, 1H), 4.44 (m, 1H), 4.34–4.12 (m, 4H), 1.12 (d, J=7 Hz, 3H); LC-MS m/z 582 (M+H).

Example 3

Preparation of (1S)-2-dimethyl-1-({3-[4-(trifluoromethyl)phenyl]-1H-pyrazol-1-yl}methyl)propyl (1S)-1-{[(2-pyridinylsulfonyl)amino]acetyl}pentylcarbamate

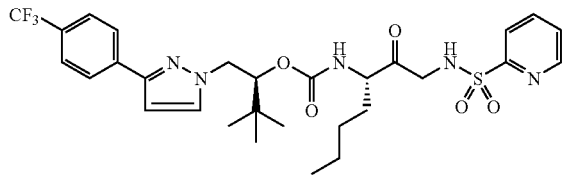

Example 3a

Preparation of tert-butyl (1S)-1-{[methoxy(methyl)amino]carbonyl}pentylcarbamate

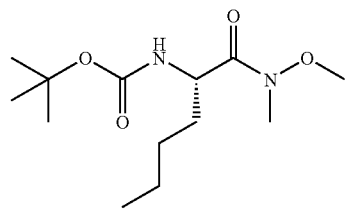

To a stirred solution of 27.8 g (120.0 mmol) of N-Boc-L-Norleucine in 150 mL of dichloromethane at −40° C. was added a solution of 18.4 mL (151.5 mmol) of 1-methylpiperidine in 40 mL of dichloromethane over 20 min. Then, 13.9 mL (145.4 mmol) of ethyl chloroformate in 40 mL of dichloromethane was added over 30 min and the reaction mixture was stirred at −40° C. for 2.5 h. A solution of 14.2 g (145.4 mmol) of N,O-dimethylhydroxylamine hydrochloride and 18.4 mL (151.5 mmol) of 1-methylpiperidine in 90 mL of dichloromethane was added over 45 min, then the reaction mixture was allowed to slowly warm to room temperature and was stirred for 18 h. It was then washed with 100 mL of water, 100 mL of 1% hydrochloric acid (2×), 100 mL of saturated aqueous sodium bicarbonate, and dried over anhydrous magnesium sulfate. Concentration in vacuo afforded 35.0 g (quantitative yield) of crude tert-butyl (1S)-1-{[methoxy(methyl)amino]carbonyl}pentylcarbamate as a thick oil. $^1$H-NMR (400 MHz, DMSO-d$_6$): δ 6.94 (d, J=8 Hz, 1H), 4.35–4.25 (m, 1H), 3.68 (s, 3H), 3.05 (s, 3H), 1.52–1.36 (m, 2H), 1.32 (s, 9H), 1.30–1.14 (m, 4H), 0.80 (t, J=6 Hz, 3H).

Example 3b

Preparation of tert-butyl (1S)-1-formylpentylcarbamate

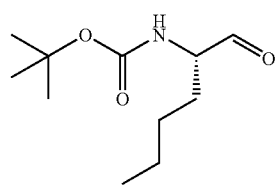

To a stirred solution of 54.0 mL (180.0 mmol) of 65 wt % bis (2-methoxyethoxy) aluminum hydride in toluene in 100 mL of toluene at −20° C. was added a solution of 35.0 g (120.0 mmol) of tert-butyl (1S)-1-{[methoxy(methyl)amino]carbonyl}pentylcarbamate in 100 mL of toluene over 30 min. After stirring at −20° C. for 2 h, 300 mL of 3M aqueous sodium chloride was added dropwise, and the layers were separated. The toluene portion was washed with 100 mL of 1 N hydrochloric acid (2×), 50 mL of 0.1 N sodium hydroxide (2×), 50 mL of brine, dried over anhydrous magnesium sulfate, and then concentrated to 200 mL. The aldehyde solution was used immediately. An aliquot was removed and concentrated, and the aldehyde was analyzed immediately. $^1$H-NMR (400 MHz, DMSO-$d_6$): δ 9.39 (s, 1H), 7.23 (d, J=7 Hz, 1H), 3.75 (m, 1H), 1.70–1.08 (m, 6H), 1.36 (s, 9H), 0.81 (t, J=6 Hz, 3H).

Example 3c

Preparation of tert-butyl (1S)-1-[(1S)-2-amino-1-hydroxyethyl]pentylcarbamate & tert-butyl (1S)-1-[(1R)-2-amino-1-hydroxyethyl]pentylcarbamate

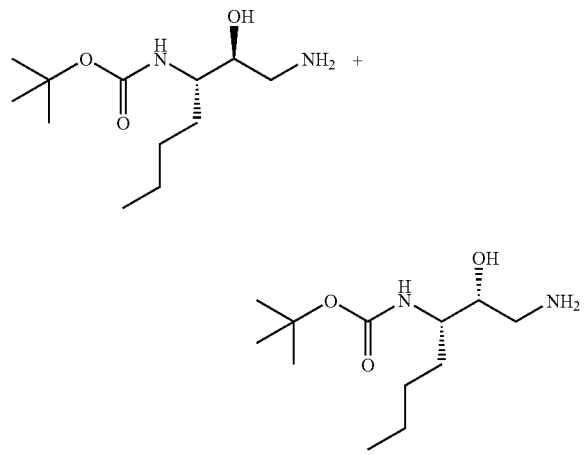

To a solution of 12.4 g (58 mmol) of tert-butyl (1S)-1-formylpentylcarbamate in 135 mL of methanol was added 3.77 g (58 mmol) of potassium cyanide followed by 3.32 mL (58 mmol) of acetic acid. The reaction mixture was stirred for 16 h and concentrated under reduced pressure to afford 14.2 g of an oil. The oil was dissolved in 140 mL of acetic acid, and 1.4 g of platinum oxide on carbon was added. The reaction mixture was hydrogenated under 50 psi hydrogen gas for 4 h, and filtered through a celite plug. The filtrate was concentrated, and the residue dissolved in ethyl acetate. The ethyl acetate solution was washed with 1M sodium hydroxide and brine, dried over anhydrous magnesium sulfate, and concentrated under reduced pressure. The residue was purified by silica gel chromatography eluting with 2M ammonia in methanol:ethyl acetate (2.5:7.5) to afford 6.61 g (46%) of tert-butyl (1S)-1-[(1S)-2-amino-1-hydroxyethyl]pentylcarbamate & tert-butyl (1S)-1-[(1R)-2-amino-1-hydroxyethyl]pentylcarbamate. $^1$H-NMR (300 MHz, diastereomers, DMSO-$d_6$): δ 6.55 and 6.21 ((d, J=9 Hz), (d, J=9 Hz), 1H), 3.55–3.09 (m, 4H), 1.39–1.05 (m, 15H), 0.87 (m, 3H); ES-LCMS m/z 247 (M+H).

Example 3d

Preparation of tert-butyl (1S)-1-{(1SR)-1-hydroxy-2-[(2-pyridinylsulfonyl)amino]ethyl}pentylcarbamate & tert-butyl (1S)-1-{(1R)-1-hydroxy-2-[(2-pyridinylsulfonyl)amino]ethyl}pentylcarbamate

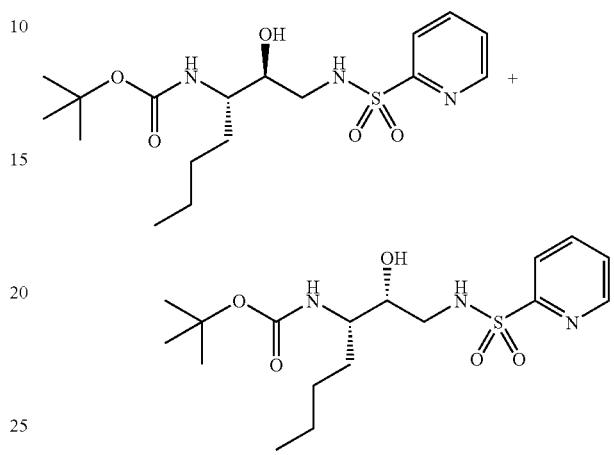

To a biphasic mixture of 4.93 g (20 mmol) of tert-butyl (1S)-1-[(1S)-2-amino-1-hydroxyethyl]pentylcarbamate & tert-butyl (1S)-1-[(1R)-2-amino-1-hydroxyethyl]pentylcarbamate in 32 mL dichloromethane and 15 mL saturated sodium bicarbonate was added 24 mL (24 mmol) of 1 M 2-pyridinesulfonyl chloride in dichloromethane. The reaction mixture was stirred overnight and then extracted with dichloromethane. The extract was washed with brine, dried over anhydrous magnesium sulfate, and concentrated under reduced pressure. The residue was purified by silica gel chromatography eluting with ethyl acetate:hexanes (6:4) to afford 5.00 g (65%) of tert-butyl (1S)-1-{(1SR)-1-hydroxy-2-[(2-pyridinylsulfonyl)amino]ethyl}pentylcarbamate & tert-butyl (1S)-1-{(1R)-1-hydroxy-2-[(2-pyridinylsulfonyl)amino]ethyl}pentylcarbamate. $^1$H-NMR (300 MHz, DMSO-$d_6$): δ 8.73 (d, J=4 Hz, 1H), 8.09 (t, J=8 Hz, 1H), 7.93 (dd, J=8 Hz, J=4 Hz, 1H), 7.68 (m, 1H), 7.60 and 7.54 ((t, J=6 Hz), (t, J=6 Hz), 1H), 6.55 and 6.36 ((d, J=9 Hz), (d, J=9 Hz), 1H), 4.78 (m, 1H), 3.50–2.70 (m, 4H), 1.61 (m, 1H), 1.37-1.05 (m, 14H), 0.86 (t, J=7 Hz, 3H); ES-LCMS m/z 410 (M+Na).

Example 3e

Preparation of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide Hydrochloride

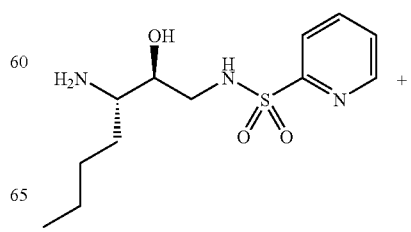

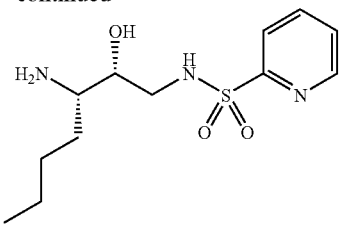

To a solution of 5.0 g (13 mmol) of tert-butyl (1S)-1-{(1SR)-1-hydroxy-2-[(2-pyridinylsulfonyl)amino]ethyl}pentylcarbamate & tert-butyl (1S)-1-{(1R)-1-hydroxy-2-[(2-pyridinylsulfonyl)amino]ethyl}pentylcarbamate in 15 mL of dioxane was added 20 mL of 4M hydrochloric acid in dioxane. The reaction mixture was stirred for 2 h and concentrated under reduced pressure to leave 4.2 g (>99) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride. $^1$H-NMR (400 MHz, DMSO-d$_6$): δ 8.71 (s, 1H), 8.10–7.92 (m, 5H), 7.79–7.65 (m, 2H), 3.86 (s, 1H), 3.16-2.91 (m 3H), 1.58–1.33 (m, 2H), 1.20 (m, 4H), 0.84 (m, 3H); ES-LCMS m/z 288 (M+H).

Example 3f

Preparation of (1S)-2,2-dimethyl-1-({3-[4-(trifluoromethyl)phenyl]-1H-pyrazol-1-yl}methyl)propyl (1S)-1-{(1S)-1-hydroxy-2-[(2-pyridinylsulfonyl)amino]ethyl}pentylcarbamate & (1S)-2,2-dimethyl-1-({3-[4-(trifluoromethyl)phenyl]1H-pyrazol-1-yl}methyl)propyl (1S)-1-{(1R)-1-hydroxy-2-[(2-pyridinylsulfonyl)amino]ethyl}pentylcarbamate

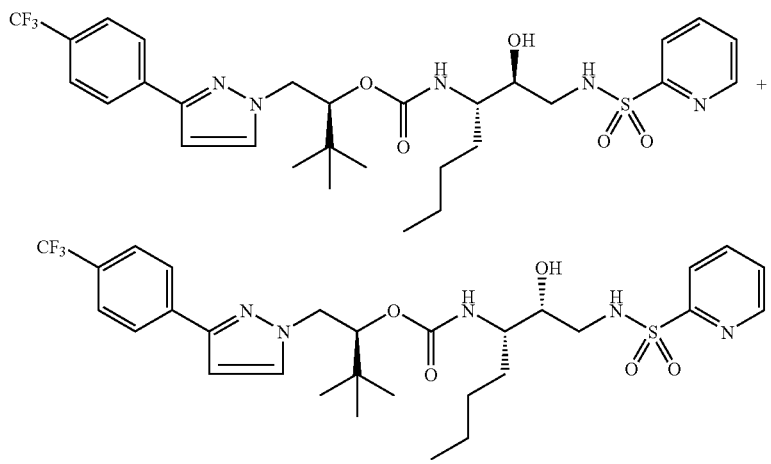

To a solution of 90 mg (0.21 mmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride and 83 mg (0.63 mmol) of N,N-diisopropylethylamine in 2 mL N,N-dimethylformamide was added 102 mg (0.21 mmol) of (1S)-2,2-dimethyl-1-({3-[4-(trifluoromethyl)phenyl]-1H-pyrazol-1-yl}methyl) propyl 4-nitrophenyl carbonate. The reaction mixture was stirred at room temperature for 48 h. It was diluted with ethyl acetate, washed with one portion of 1M sodium hydroxide and with 1 portion of brine, dried over anhydrous magnesium sulfate, and concentrated under reduced pressure. The residue was purified by silica gel chromatography eluting with ethyl acetate:hexanes (3:1) to afford 90 mg (68%) of (1S)-2,2-dimethyl-1-({3-[4-(trifluoromethyl)phenyl]-1H-pyrazol-1-yl}methyl)propyl (1S)-1-{(1S)-1-hydroxy-2-[(2-pyridinylsulfonyl)amino]ethyl}pentylcarbamate & (1S)-2,2-dimethyl-1-({3-[4-(trifluoromethyl)phenyl]-1H-pyrazol-1-yl}methyl)propyl (1S)-1-{(1R)-1-hydroxy-2-[(2-pyridinylsulfonyl)amino]ethyl}pentylcarbamate. $^1$H-NMR (300 MHz, DMSO-d$_6$): δ 8.70 (d, J=4 Hz, 1H), 8.11–7.45 (m, 10H), 6.76 (s, 1H), 6.54 (d, J=9 Hz, 1H), 4.90–4.76 (m, 2H), 4.46 (d, J=13 Hz, 1H), 4.16 (m, 1H), 3.05 (m, 1H), 1.27 (m, 1H), 1.05–0.86 (m, 14H), 0.68 (m, 3H); ES-LCMS m/z 648 (M+Na).

Example 3g

Preparation of (1S)-2,2-dimethyl-1-({3-[4-(trifluoromethyl)phenyl]-1H-pyrazol-1-yl}methyl)propyl (1S)-1-{[(2-pyridinylsulfonyl)amino]acetyl}pentylcarbamate

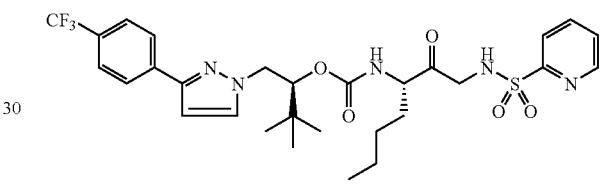

To a solution of 90 mg (0.14 mmol) of (1S)-2,2-dimethyl-1-({3-[4-(trifluoromethyl)phenyl]-1H-pyrazol-1-yl}methyl) propyl (1S)-1-{(1S)-1-hydroxy-2-[(2-pyridinylsulfonyl)amino]ethyl}pentylcarbamate & (1S)-2,2-dimethyl-1-({3-[4-(trifluoromethyl)phenyl]-1H-pyrazol-1-yl}methyl)propyl (1S)-1-{(1R)-1-hydroxy-2-[(2-pyridinylsulfonyl)amino]ethyl}pentylcarbamate in 2 mL of dichloromethane was added 76 mg (0.18 mmol) of Dess-Martin periodinane. The reaction mixture was stirred for 15 min, and then filtered through a celite plug with dichloromethane. The filtrate was concentrated, and the residue was purified by silica gel chromatography eluting with ethyl acetate:hexanes (6.5:3.5) to afford 56 mg (62%) of (1S)-2,2-dimethyl-1-({3-[4-(trifluoromethyl)phenyl]-1H-pyrazol-1-yl}methyl)propyl (1S)-1-{[(2-pyridinylsulfonyl)amino]acetyl}pentylcarbamate. $^1$H-NMR (300 MHz, T=100° C., DMSO$_6$): δ 8.66 (d, J=4 Hz, 1H), 8.08–7.60 (m, 9H), 7.17 (m, 1H), 6.72 (d, J=2 Hz, 1H), 4.90 (d, J=9 Hz, 1H), 4.49 (d, J=14 Hz, 1H), 4.26–3.85 (m, 4H), 1.56 (m, 1H), 1.40 (m, 1H), 1.29–1.01 (m, 13H) 0.78 (m, 3H); ES-LCMS m/z 646 (M+Na); HRMS C$_{29}$H$_{36}$F$_3$N$_5$O$_5$S$_1$ m/z 646.2287 (M+Na)$^+$Cal; 646.2283 (M+Na)$^+$.

Example 4

Preparation of (1S)-2,2-dimethyl-1-({3-[4-(trifluoromethyl)phenyl]-1H-pyrazol-1-yl}methyl)propyl (1S)-1-{[(4-morpholinylcarbonyl)amino]acetyl}pentylcarbamate

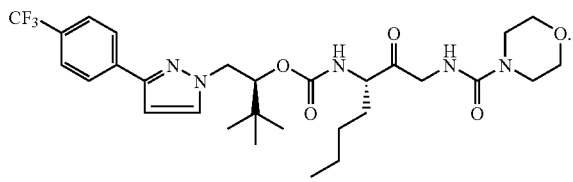

Example 4a

Preparation of tert-butyl (1S)-1-{(1S)-1-hydroxy-2-[(4-morpholinylcarbonyl)amino]ethyl}pentylcarbamate & tert-butyl (1S)-1-{(1R)-1-hydroxy-2-[(4-morpholinylcarbonyl)amino]ethyl}pentylcarbamate

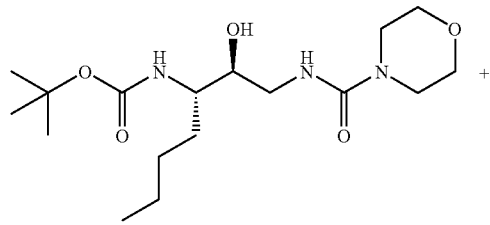

+

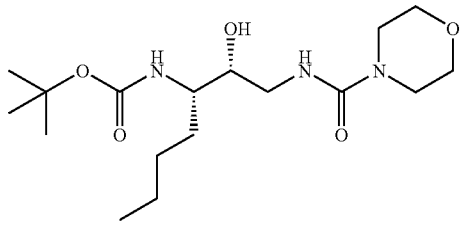

To a solution of 100 mg (0.41 mmol) of tert-butyl (1S)-1-[(1S)-2-amino-1-hydroxyethyl]pentylcarbamate & tert-butyl (1S)-1-[(1R)-2-amino-1-hydroxyethyl]pentylcarbamate and 0.070 mL (0.41 mmol) of N,N-diisopropylethylamine in 2 mL dichloromethane was added 0.050 mL (0.41 mmol) 4-morpholinecarbonyl chloride. The reaction mixture was stirred at room temperature for 18 h, diluted with dichloromethane, and washed with 1N hydrochloric acid and brine. After drying over anhydrous magnesium sulfate, the solution was concentrated under reduced pressure, and the residue was purified by silica gel chromatography eluting with ethyl acetate to afford 130 mg (89%) of tert-butyl (1S)-1-{(1S)-1-hydroxy-2-[(4-morpholinylcarbonyl)amino]ethyl}pentylcarbamate & tert-butyl (1S)-1-{(1R)-1-hydroxy-2-[(4-morpholinylcarbonyl)amino]ethyl}pentylcarbamate. $^1$H-NMR (300 MHz, DMSO-d$_6$): δ 6.55–6.36 (m, 2H), 5.00–4.65 (m, 1H), 3.60-3.23 (m, 9H), 3.10–2.80 (m, 2H), 1.40–1.05 (m, 15 H), 0.87 (m, 1H); ES-LCMS m/z 382 (M+Na).

Example 4b

Preparation of (1S)-2,2-dimethyl-1-({3-[4-(trifluoromethyl)phenyl]-1H-pyrazol-1-yl}methyl)propyl (1S)-1-{(1S)-1-hydroxy-2-[(4-morpholinylcarbonyl)amino]ethyl}pentylcarbamate & (1S)-2,2-dimethyl-1-({3-[4-(trifluoromethyl)phenyl]-1H-pyrazol-1-yl}methyl)propyl (1S)-1-{(1R)-1-hydroxy-2-[(4-morpholinylcarbonyl)amino]ethyl}pentylcarbamate

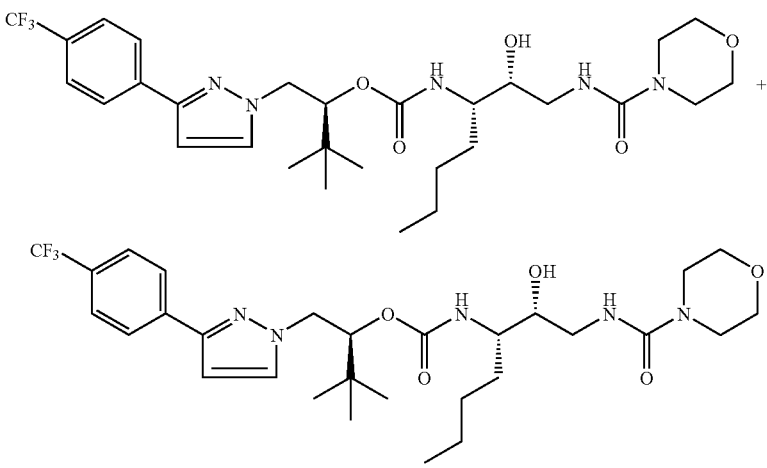

To a solution of 130 mg (0.36 mmol) of tert-butyl (1S)-1-{(1S)-1-hydroxy-2-[(4-morpholinylcarbonyl)amino]ethyl}pentylcarbamate & tert-butyl (1S)-1-{(1R)-1-hydroxy-2-[(4-morpholinylcarbonyl)amino]ethyl}pentylcarbamate in 1 mL of dioxane was added 5 mL of 4M hydrochloric acid in dioxane. The reaction mixture was stirred for 2 h and concentrated under reduced pressure. Half of the product was carried forward. This material was slurried in N,N-dimethylformamide before 0.094 mL (0.54 mmol) of N,N-diisopropylethylamine was added, followed by 86 mg (0.18 mmol) of (1S)-2,2-dimethyl-1-({3-[4-(trifluoromethyl)phenyl]-1H-pyrazol-1-yl}methyl)propyl 4-nitrophenyl carbonate. The reaction mixture was stirred at room temperature for 18 h, and then diluted with ethyl acetate before being washed with 1M sodium hydroxide and brine, dried over anhydrous magnesium sulfate, and concentrated under reduced pressure. The residue was purified by silica gel chromatography eluting with ethyl acetate to afford 60 mg (55%) of (1S)-2,2-dimethyl-1-({3-[4-(trifluoromethyl)phenyl]-1H-pyrazol-1-yl}methyl)propyl (1S)-1-{(1S)-1-hydroxy-2-[(4-morpholinylcarbonyl)amino]ethyl}pentylcarbamate & (1S)-2,2-dimethyl-1-({3-[4-(trifluoromethyl)phenyl]-1H-pyrazol-1-yl}methyl)propyl (1S)-1-{(1R)-1-hydroxy-2-[(4-morpholinylcarbonyl)amino]ethyl}pentylcarbamate. $^1$H-NMR (300 MHz, DMSO-$d_6$): δ 7.99 (m, 2H), 7.74 (d, J=8 Hz, 2H), 6.77 (s, 1H), 6.58 (d, J=9 Hz, 1H), 6.33 (m, 1H), 4.95–4.75 (m, 2H), 4.48 (d, J=13 Hz, 1H), 4.19 (t, J=12 Hz, 1H), 3.45–3.10 (m, 13H), 1.25 (m, 1H), 0.99 (m, 14H), 0.67 (m, 3H); ES-LCMS m/z 620 (M+Na).

Example 4c

Preparation of (1S)-2,2-dimethyl-1-({3-[4-(trifluoromethyl)phenyl]-1H-pyrazol-1-yl}methyl)propyl (1S)-1-{[(4-morpholinylcarbonyl)amino]acetyl}pentylcarbamate

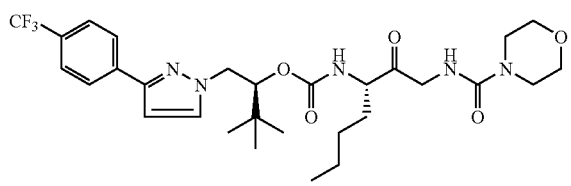

(1S)-2,2-Dimethyl-1-({3-[4-(trifluoromethyl)phenyl]-1H-pyrazol-1-yl}methyl)propyl (1S)-1-{[(4-morpholinylcarbonyl)amino]acetyl}pentylcarbamate was prepared (50% yield) as in example 3g except that (1S)-2,2-dimethyl-1-({3-[4-(trifluoromethyl)phenyl]-1H-pyrazol-1-yl}methyl)propyl (1S)-1-{(1S)-1-hydroxy-2-[(4-morpholinylcarbonyl)amino]ethyl}pentylcarbamate & (1S)-2,2-dimethyl-1-({3-[4-(trifluoromethyl)phenyl]-1H-pyrazol-1-yl}methyl)propyl (1S)-1-{(1R)-1-hydroxy-2-[(4-morpholinylcarbonyl)amino]ethyl}pentylcarbamate were substituted for (1S)-2,2-dimethyl-1-({3-[4-(trifluoromethyl)phenyl]-1H-pyrazol-1-yl}methyl)propyl (1S)-1-{(1S)-1-hydroxy-2-[(2-pyridinylsulfonyl)amino]ethyl}pentylcarbamate & (1S)-2,2-dimethyl-1-({3-[4-(trifluoromethyl)phenyl]-1H-pyrazol-1-yl}methyl)propyl (1S)-1-{(1R)-1-hydroxy-2-[(2-pyridinylsulfonyl)amino]ethyl}pentylcarbamate. $^1$H-NMR (300 MHz, DMSO-$d_6$): δ 8.00 (d, J=8 Hz, 2H), 7.74 (m, 3H), 7.47 (d, J=8 Hz, 1H), 6.81–6.72 (m, 2H), 4.87 (d, J=9 Hz, 1H), 4.48 (m, 1H), 4.22 (m, 1H), 3.88-3.75 (m, 2H), 3.53 (t, J=4 Hz, 4H), 3.38 under water peak (m, 1H), 3.24 (t, J=4 Hz, 4H), 1.55 (m, 1H), 1.33 (m, 1H), 1.15–0.85 (m, 13H), 0.72 (t, J=6 Hz, 3H); ES-LCMS m/z 596 (M+H); HRMS $C_{29}H_{40}N_5O_5F_3$ m/Z 596.3060 (M+H)$^+$Cal; 596.3047 (M+H)$^+$.

Example 5

Preparation of (1S)-2,2-dimethyl-1-({3-[4-(trifluoromethyl)phenyl]-1H-pyrazol-1-yl}methyl)propyl (1S)-1-{[(6-fluoro-2-pyridinyl)amino]acetyl}pentylcarbamate

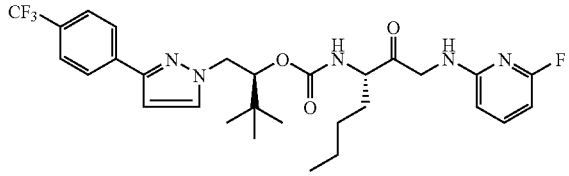

Example 5a

Preparation of tert-butyl (1S)-1-{(1S)-2-[(6-fluoro-2-pyridinyl)amino]-1-hydroxyethyl}pentylcarbamate & tert-butyl (1S)-1-{(1R)-2-[(6-fluoro-2-pyridinyl)amino]-1-hydroxyethyl}pentylcarbamate

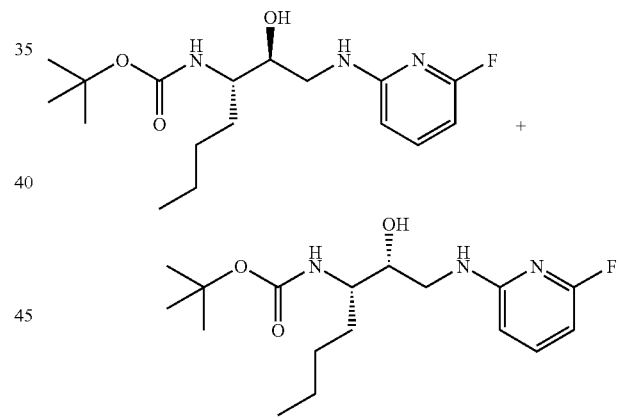

To a solution of 100 mg (0.41 mmol) of tert-butyl (1S)-1-[(1S)-2-amino-1-hydroxyethyl]pentylcarbamate & tert-butyl (1S)-1-[(1R)-2-amino-1-hydroxyethyl]pentylcarbamate and 0.07 mL (0.46 mmol) of N,N-diisopropylethylamine in 0.5 mL dioxane was added 0.042 mL (0.46 mmol) of 2,6-difluoropyridine. The reaction mixture was stirred at 45° C. for 16 h, then at 50° C. for 20 h. The reaction mixture was then allowed to cool before being diluted with ethyl acetate, washed with brine, dried over anhydrous magnesium sulfate, and concentrated under reduced pressure. The residue was purified by silica gel chromatography eluting with ethyl acetate:hexanes (3:7) to afford 40 mg (29%) of tert-butyl (1S)-1-{(1S)-2-[(6-fluoro-2-pyridinyl)amino]-1-hydroxyethyl}pentylcarbamate & tert-butyl (1S)-1-{(1R)-2-[(6-fluoro-2-pyridinyl)amino]-1-hydroxyethyl}pentylcarbamate. ES-LCMS m/z 364 (M+Na).

Example 5b

Preparation of (1S)-2,2-dimethyl-1-({3-[4-(trifluoromethyl)phenyl]-1H-pyrazol-1-yl}methyl)propyl (1S)-1-{(1S)-2-[(6-fluoro-2-pyridinyl)amino]-1-hydroxyethyl}pentylcarbamate & (1S)-2,2-dimethyl-1-({3-[4-(trifluoromethyl)phenyl]-1H-pyrazol-1-yl}methyl)propyl (1S)-1-{(1R)-2-[(6-fluoro-2-pyridinyl)amino]-1-hydroxyethyl}pentylcarbamate

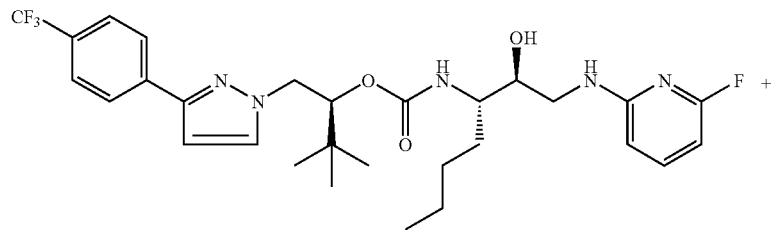

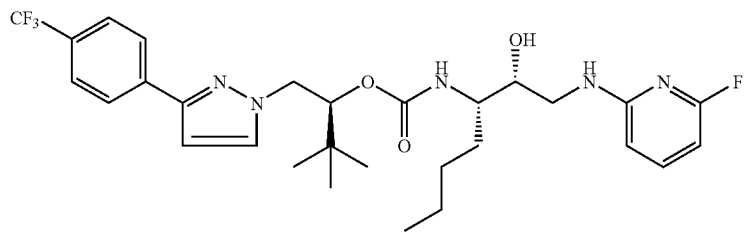

To a solution of 40 mg (0.12 mmol) of tert-butyl (1S)-1-{(1S)-2-[(6-fluoro-2-pyridinyl)amino]-1-hydroxyethyl}pentylcarbamate & tert-butyl (1S)-1-{(1R)-2-[(6-fluoro-2-pyridinyl)amino]-1-hydroxyethyl}pentylcarbamate in 1 mL dioxane was added 5 mL of 4M hydrochloric acid in dioxane. The reaction mixture was stirred for 2 h before being concentrated under reduced pressure. The residue was dissolved in 1 mL of N,N-dimethylformamide before 0.081 mL (0.47 mmol) of N,N-diisopropylethylamine and 56 mg (0.12 mmol) of (1S)-2,2-dimethyl-1-({3-[4-(trifluoromethyl)phenyl]-1H-pyrazol-1-yl}methyl)propyl 4-nitrophenyl carbonate were added. The reaction mixture was stirred at room temperature for 18 h, diluted with ethyl acetate, washed with 1M sodium hydroxide and brine, dried over anhydrous magnesium sulfate, and concentrated under reduced pressure. The residue was purified by silica gel chromatography eluting with ethyl acetate:hexanes (2:3) to afford 40 mg (59%) of (1S)-2,2-dimethyl-1-({3-[4(trifluoromethyl)phenyl]-1H-pyrazol-1-yl}methyl)propyl (1S)-1-{(1S)-2-[(6-fluoro-2-pyridinyl)amino]-1-hydroxyethyl}pentylcarbamate & (1S)-2,2-dimethyl-1-({3-[4-(trifluoromethyl)phenyl]-1H-pyrazol-1-yl}methyl)propyl (1S)-1-{(1R)-2-[(6-fluoro-2-pyridinyl)amino]-1-hydroxyethyl}pentylcarbamate. ES-LCMS m/z 602 (M+Na).

Example 5c

Preparation of (1S)-2,2-dimethyl-1-({3-[4-(trifluoromethyl)phenyl]-1H-pyrazol-1-yl}methyl)propyl (1S)-1-{[(6-fluoro-2-pyridinyl)amino]acetyl}pentylcarbamate

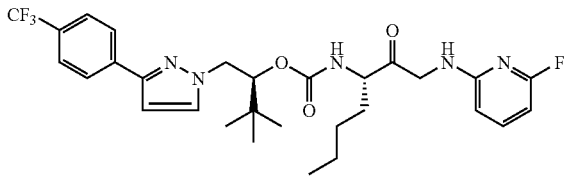

(1S)-2,2-dimethyl-1-({3-[4-(trifluoromethyl)phenyl]-1H-pyrazol-1-yl}methyl)propyl (1S)-1-{[(6-fluoro-2-pyridinyl)amino]acetyl}pentylcarbamate was prepared as in example 3g (15% yield) except that (1S)-2,2-dimethyl-1-({3-[4-(trifluoromethyl)phenyl]-1H-pyrazol-1-yl}methyl)propyl (1S)-1-{(1S)-2-[(6-fluoro-2-pyridinyl)amino]-1-hydroxyethyl}pentylcarbamate & (1S)-2,2-dimethyl-1-({3-[4-(trifluoromethyl)phenyl]-1H-pyrazol-1-yl}methyl)propyl (1S)-1-{(1R)-2-[(6-fluoro-2-pyridinyl)amino]-1-hydroxyethyl}pentylcarbamate were substituted for (1S)-2,2-dimethyl-1-({3-[4-(trifluoromethyl)phenyl]-1H-pyrazol-1-yl}methyl)propyl (1S)-1-{(1S)-1-hydroxy-2-[(2-pyridinylsulfonyl)amino]ethyl}pentylcarbamate & (1S)-2,2-dimethyl-1-({3-[4-(trifluoromethyl)phenyl]-1H-pyrazol-1-yl}methyl)propyl (1S)-1-{(1R)-1-hydroxy-2-[(2-pyridinylsulfonyl)amino]ethyl}pentylcarbamate. ES-LCMS m/z 600 (M+Na); HRMS $C_{29}H_{35}N_5O_3F_4$ m/z 578.2754 (M+H)+Cal; 578.2745 (M+H)+.

Example 6

Preparation of (3S)-1-(1,3-benzothiazol-2-yl)-4,4-dimethylpyrrolidinyl (1S)-1-{[(2-pyridinylsulfonyl)amino]acetyl}pentylcarbamate

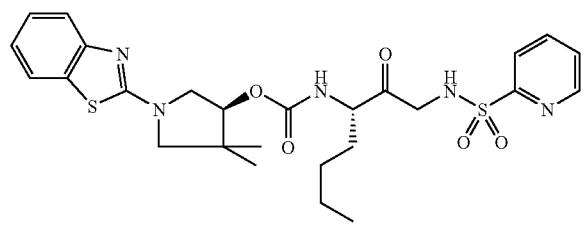

Example 6a

Preparation of (2S)-3,3-dimethyl-1,2,4-butanetriol

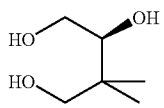

To a 0° C. solution of 5.01 g (38.5 mmol) of (S)-(+)-pantolactone in 150 mL of methanol was added 3.72 g (98.5 mmol) of sodium borohydride carefully. After gas evolution had subsided, the ice-bath was removed and the reaction mixture was closely monitored, cooling again to 0° C. with an ice-water bath as needed when gas evolution became vigorous. The ice-water bath was removed and the reaction mixture was stirred at room temperature for 4 h. Dowex 50Wx4-400 (H+) resin was added to the solution until the reaction mixture was neutral. The resin was filtered off and the filtrate was concentrated under reduced pressure. The oil was diluted and concentrated with portions of methanol and then toluene. The remaining clear oil was dried under high vacuum to afford 5.16 g (>99%) of (2S)-3,3-dimethyl-1,2,4-butanetriol. $^1$H-NMR (300 MHz, CDCl$_3$): δ 3.82–3.49 (m, 5H), 3.11 (d, J=4 Hz, 1H), 2.62 (m, 1H), 2.42 (m, 1H), 0.98 (d, J=6 Hz, 6H).

Example 6b

Preparation of (2S)-2-hydroxy-3,3-dimethyl-4-[(methylsulfonyl)oxy]butyl Methanesulfonate

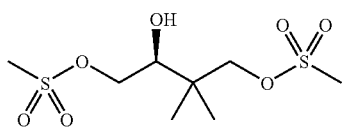

To a 0° C. solution of 25.3 g (189 mmol) of (2S)-3,3-dimethyl-1,2,4-butanetriol in 170 mL of pyridine was added dropwise 29.1 mL (378 mmol) of methanesulfonyl chloride. The reaction mixture was allowed to warm slowly to room temperature, and was stirred for 18 h. It was then diluted with dichloromethane. To the resulting solution was added 200 mL of 1 N hydrochloric acid, followed by enough concentrated hydrochloric acid to acidify the aqueous phase (pH=2). The mixture was extracted with dichloromethane, and the combined extracts were washed with brine and concentrated under reduced pressure. The residue was purified by silica gel chromatography eluting with acetone:dichloromethane (1:9) to afford 21.75 g (52%) of (2S)-2-hydroxy-3,3-dimethyl-4-[(methylsulfonyl)oxy]butyl methanesulfonate. $^1$H-NMR (300 MHz, DMSO-d$_6$): δ 5.48 (d, J=6 Hz, 1H), 4.30 (dd, J=3 Hz, J=10 Hz, 1H), 4.05–3.91 (m, 3H), 3.16 (d, J=4 Hz, 6H), 0.90 (d, J=13 Hz, 6H).

Example 6c

Preparation of (3S)-1-benzyl-4,4-dimethyl-3-pyrrolidinol

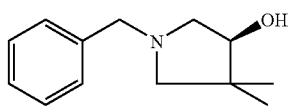

A solution of 21.7 g (75 mmol) of (2S)-2-hydroxy-3,3-dimethyl-4-[(methylsulfonyl)oxy]butyl methanesulfonate and 24.4 mL (228 mmol) of benzylamine in 200 mL of ethanol was heated to 120° C. for 18 h in a sealed pressure reactor. The reaction mixture was allowed to cool to room temperature before the reactor was vented and the reaction mixture was concentrated under reduced pressure to afford 100 mL of solution. The solution was diluted with 50 mL water and acidified with concentrated hydrochloric acid. The aqueous phase was washed with ether, basicified with 5M sodium hydroxide, and extracted with ether. The ether extract was concentrated under reduced pressure and the residue was purified by silica gel chromatography eluting with 2M ammonia in methanol:ethyl acetate (0.25:9.75) to afford 13.8 g (90%) of (3S)-1-benzyl-4,4-dimethyl-3-pyrrolidinol. $^1$H-NMR (300 MHz, CDCl$_3$): δ 7.36–7.30 (m, 5H), 3.77 (br s, 1H), 3.65 (s, 2H), 2.99–2.93 (m, 1H), 2.64–2.55 (m, 2H), 2.31 (d, J=9 Hz, 1H), 1.76 (d, J=7 Hz, 1H), 1.09 (d, J=1 Hz, 6H).

Example 6d

Preparation of (3S)-4,4-dimethyl-3-pyrrolidinol Hydrochloride

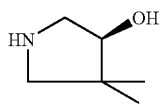

To a solution of 6.34 g (41.7 mmol) of (3S)-1-benzyl-4,4-dimethyl-3-pyrrolidinol in 250 mL of ethanol and 50 mL of 1N hydrochloric acid was added 300 mg of 10% palladium on carbon. The reaction mixture was stirred under 40 psi of hydrogen gas for 18 h. To the reaction mixture was added 300 mg of 10% palladium on carbon and 2 mL of concentrated hydrochloric acid. The reaction mixture was stirred under 40 psi of hydrogen gas for 72 h. The catalyst was filtered off over celite, and the filtrate was concentrated. Several portions of toluene were distilled from the residue, which was then dried under high vacuum to afford 4.74 g (>99%) of (3S)-4,4-dimethyl-3-pyrrolidinol hydrochloride. $^1$H-NMR (300 MHz, DMSO-$d_6$): δ 9.46 (d, J=40 Hz, 2H), 5.43 (br s, 1H), 3.75 (m, 1H), 3.36 (m, 1H), 2.88 (m, 3H), 0.96 (d, J=10 Hz, 6H).

Example 6e

Preparation of (3S)-1-(1,3-benzothiazol-2-yl)-4,4-dimethyl-3-pyrrolidinol

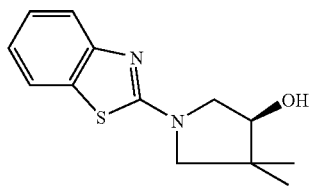

To a slurry of 600 mg (4 mmol) of (3S)-4,4-dimethyl-3-pyrrolidinol hydrochloride and 670 mg (4 mmol) of 2-chlorobenzthiazole was added a solution of 1.0 g (12 mmol) of sodium bicarbonate in water. The reaction mixture was heated to 80° C. and stirred overnight. It was then diluted with water, the resulting mixture was extracted with ethyl acetate. The extracts were combined, dried over anhydrous magnesium sulfate, and concentrated under reduced pressure to afford 950 mg (96%) of (3S)-1-(1,3-benzothiazol-2-yl)-4,4-dimethyl-3-pyrrolidinol. $^1$H-NMR (300 MHz, DMSO-$d_6$): δ 7.76 (d, J=8 Hz, 1H), 7.46 (d, J=8 Hz, 1H), 7.27 (t, J=8 Hz, 1H), 7.04 (t, J=8 Hz, 1H), 5.27 (d, J=5 Hz, 1H), 3.84–3.77 (m, 2H), 3.39–3.25 under DMSO peak (m, 3H), 1.05 (d, J=8 Hz, 6H); ES-LCMS m/z 249 (M+H).

Example 6f

Preparation of (3S)-1-(1,3-benzothiazol-2-yl)-4,4-dimethylpyrrolidinyl 4-nitrophenyl Carbonate

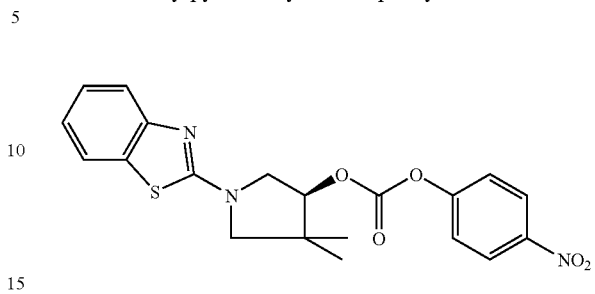

To a solution of 950 mg (3.83 mmol) of (3S)-1-(1,3-benzothiazol-2-yl)-4,4-dimethyl-3-pyrrolidinol in 10 mL of dichloromethane was added 920 mg (4.6 mmol) of 4-nitrophenyl chloroformate followed by the dropwise addition of 0.37 mL (4.6 mmol) of pyridine. The reaction mixture was stirred at room temperature for 18 h. It was then diluted with ethyl acetate, washed with saturated sodium bicarbonate and brine, dried over anhydrous magnesium sulfate, and concentrated under reduced pressure. The residue was purified by silica gel chromatography eluting with ethyl acetate: hexanes (3.5:6.5) to afford 1.17 g (74%) of (3S)-1-(1,3-benzothiazol-2-yl)-4,4-dimethylpyrrolidinyl 4-nitrophenyl carbonate. $^1$H-NMR (300 MHz, DMSO-$d_6$): δ 8.35 (d, J=9 Hz, 2H), 7.81 (d, J=8 Hz, 1H), 7.64 (d, J=9 Hz, 2H), 7.50 (d, J=8 Hz, 1H), 7.31 (t, J=8 Hz, 1H), 7.09 (t, J=8 Hz, 1H), 5.06 (d, J=4 Hz, 1H), 4.13 (dd, J=13 Hz, J=5 Hz, 1H), 3.86 (d, J=4 Hz, 1H), 3.53–3.41 under DMSO peak (m, 2H), 1.24 (s, 3H), 1.18 (s, 3H); ES-LCMS m/z 414 (M+H).

Example 6g

Preparation of (3S)-1-(1,3-benzothiazol-2-yl)-4,4-dimethylpyrrolidinyl (1S)-1-{(1S)-1-hydroxy-2-[(2-pyridinylsulfonyl)amino]ethyl}pentylcarbamate & (3S)-1-(1,3-benzothiazol-2-yl)-4,4-dimethylpyrrolidinyl (1S)-1-{(1R)-1-hydroxy-2-[(2-pyridinylsulfonyl)amino]ethyl}pentylcarbamate

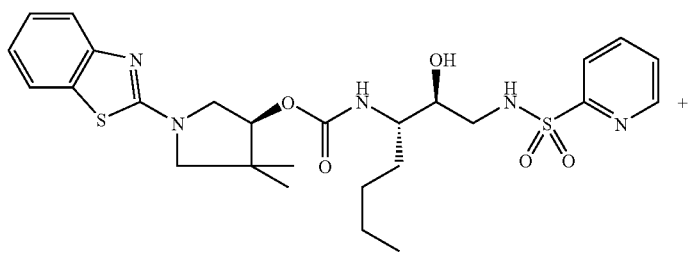

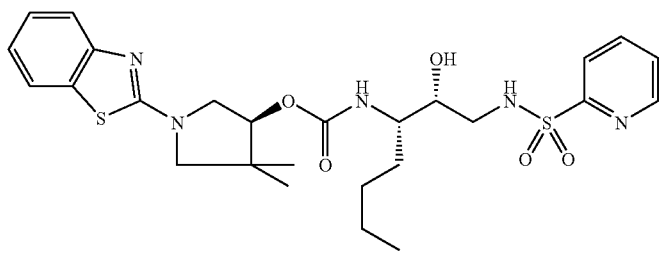

(3S)-1-(1,3-benzothiazol-2-yl)-4,4-dimethylpyrrolidinyl (1S)-1-{(1S)-1-hydroxy-2-[(2-pyridinylsulfonyl)amino]ethyl}pentylcarbamate & (3S)-1-(1,3-benzothiazol-2-yl)-4,4-dimethylpyrrolidinyl (1S)-1-{(1R)-1-hydroxy-2-[(2-pyridinylsulfonyl)amino]ethyl}pentylcarbamate were prepared as in example 3f except that (3S)-1-(1,3-benzothiazol-2-yl)-4,4-dimethylpyrrolidinyl 4-nitrophenyl carbonate was substituted for (1S)-2,2-dimethyl-1-({3-[4-(trifluoromethyl)phenyl]-1H-pyrazol-1-yl}methyl)propyl 4-nitrophenyl carbonate. 83% yield. ES-LCMS m/z 562 (M+H).

Example 6h

Preparation of (1S)-2,2-dimethyl-1-({3-[4-(trifluoromethyl)phenyl]-1H-pyrazol-1-yl}methyl)propyl (1S)-1-{[(2-pyridinylsulfonyl)amino]acetyl}pentylcarbamate (1S)-2,2-Dimethyl-1-({3-[4-(trifluoromethyl)phenyl]-1H-pyrazol-1-yl}methyl)propyl (1S)-1-{[(2-pyridinylsulfonyl)amino]acetyl}pentylcarbamate was prepared as in example 3g (27% yield) except that (3S)-1-(1,3-benzothiazol-2-yl)-4,4-dimethylpyrrolidinyl (1S)-1-{(1S)-1-hydroxy-2-[(2-pyridinylsulfonyl)amino]ethyl}pentylcarbamate & (3S)-1-(1,3-benzothiazol-2-yl)-4,4-dimethylpyrrolidinyl (1S)-1-{(1R)-1-hydroxy-2-[(2-pyridinylsulfonyl)amino]ethyl}pentylcarbamate were substituted for (1S)-2,2-dimethyl-1-({3-[4-(trifluoromethyl)phenyl]-1H-pyrazol-1-yl}methyl)propyl (1S)-1-{(1S)-1-hydroxy-2-[(2-pyridinylsulfonyl)amino]ethyl}pentylcarbamate & (1S)-2,2-dimethyl-1-({3-[4-(trifluoromethyl)phenyl]-1H-pyrazol-1-yl}methyl)propyl (1S)-1-{(1R)-1-hydroxy-2-[(2-pyridinylsulfonyl)amino]ethyl}pentylcarbamate. $^1$H-NMR (300 MHz, DMSO-$d_6$): δ 8.67 (d, J=6 Hz, 1H), 8.13–8.03 (m, 2H), 7.88 (d, J=8 Hz, 1H), 7.77 (d, J=8 Hz, 2H), 7.65 (dd, J=7 Hz, J=5 Hz, 1H), 7.45 (d, J=8 Hz, 1H), 7.27 (t, J=8 Hz, 1H), 7.04 (t, J=8 Hz, 1H), 4.89 (d, J=4 Hz, 1H), 4.15-3.95 (m, 5H), 3.53–3.40 under DMSO peak (m, 2H), 1.60 (m, 1H), 1.42 (m, 1H), 1.23 (m, 4H), 1.09 (s, 3H), 1.06 (s, 3H), 0.82 (m, 3H); ES-LCMS m/z 560 (M+H); HRMS $C_{26}H_{33}N_5O_5S_2$ m/z 560.2001 (M+Na)$^+$Cal; 560.2010 (M+Na)$^+$.

Example 7

Preparation of (1S)-2,2-dimethyl-1-{[3-(trifluoromethyl)-1H-pyrazol-1-yl]methyl}propyl (1S)-1-{[(2-pyridinylsulfonyl)amino]acetyl}pentylcarbamate

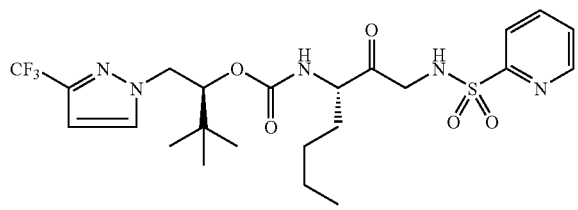

Example 7a

Preparation of (4S)-4-tert-butyl-1,3,2-dioxathiolane 2,2-dioxide

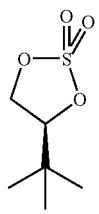

To 5.63 g (47.63 mmol) of (2S)-3,3-dimethyl-1,2-butanediol in 48 mL of carbon tetrachloride was added 3.47 mL (47.63 mmol) of thionyl chloride. The resulting mixture was heated at reflux for 1 h, and cooled to 0° C., before 48 mL of acetonitrile was added. Then, 1.0 mg (4.8 μmol) of ruthenium(III) chloride hydrate was added, followed by 15.28 g (71.45 mmol) of sodium periodate. The reaction mixture was diluted with 71 mL of water and stirred for 2 h. It was then extracted with diethyl ether. The extract was washed with saturated aqueous sodium bicarbonate, dried over anhydrous magnesium sulfate, filtered, and concentrated. The residue was purified by silica gel column chromatography eluting with an ethyl acetate:hexanes solution (3:7) to give 8.33 g (97%) of (4S)-4-tert-butyl-1,3,2-dioxathiolane 2,2-dioxide. $R_f$=0.30 (3:7 ethyl acetate:hexanes); $^1$H-NMR (300 MHz, DMSO-$d_6$): δ 4.99–4.88 (m, 2H), 4.78 (t, J=8 Hz, 1H), 0.94 (s, 9H).

Example 7b

Preparation of (2S)-3,3-dimethyl-1-[3-(trifluoromethyl)-1H-pyrazol-1-yl]-2-butanol

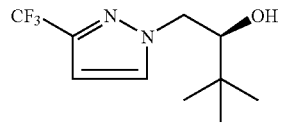

To 999.9 mg (5.55 mmol) of (4S)-4-tert-butyl-1,3,2-dioxathiolane 2,2-dioxide in 18 mL of N,N-dimethylformamide was added 755.0 mg (5.55 mmol) of 3-(trifluoromethyl)-1H-pyrazole. Then, 805.2 mg (5.83 mmol) of potassium carbonate was added, and the mixture was heated at 100° C. for 22 h. The resulting solution was cooled and 20 mL of acetyl chloride:methanol (1:9) were added. The reaction mixture was stirred for 2 h, and then saturated aqueous sodium bicarbonate was added. The mixture was extracted with ethyl acetate, and the extract was dried over anhydrous magnesium sulfate, filtered, and concentrated. The residue was purified by silica gel column chromatography eluting with an ethyl acetate:hexanes solution (1:4) to give 736.5 mg (56%) of (2S)-3,3-dimethyl-1-[3-(trifluoromethyl)-1H-pyrazol-1-yl]-2-butanol and a small amount of the other regioisomer. $R_f$=0.23 (1:4 ethyl acetate:hexanes); $^1$H-NMR (300 MHz, DMSO-$d_6$): δ 7.90 (s, 1H), 6.65 (d, J=2 Hz, 1H), 4.93 (br s, 1H), 4.30 (dd, J=14 Hz, J=2 Hz, 1H), 3.96 (dd, J=14 Hz, 10 Hz, 1H), 3.45 (d, J=10 Hz, 1H), 0.90 (s, 9H); ES-LCMS m/z 237 (M+H).

Example 7c

Preparation of 4-nitrophenyl (1S)-2,2-dimethyl-1-{[3-(trifluoromethyl)-1H-pyrazol-1-yl]methyl}propyl Carbonate

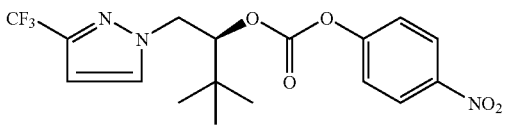

To 875.3 mg (3.71 mmol) of (2S)-3,3-dimethyl-1-[3-(trifluoromethyl)-1H-pyrazol-1-yl]-2-butanol in 12 mL of 1,2-dichloroethane at room temperature was added 746.8 g (3.71 mmol) of 4-nitrophenyl chloroformate. Then, 359.6 µL (4.45 mmol) of pyridine was added and the solution was heated at reflux for 22 h. Upon cooling to room temperature, saturated aqueous sodium bicarbonate was added to the solution, and the mixture was extracted with ethyl acetate. The extract was washed with saturated aqueous sodium chloride, dried over anhydrous magnesium sulfate, filtered, and concentrated. The residue was purified by silica gel column chromatography eluting with an ethyl acetate:hexanes solution (1:4) to give 1.39 g (93%) of 4-nitrophenyl (1S)-2,2-dimethyl-1-{[3-(trifluoromethyl)-1H-pyrazol-1-yl]methyl}propyl carbonate. $R_f$=0.29 (3:7 ethyl acetate:hexanes); $^1$H-NMR (300 MHz, DMSO-$d_6$): δ 8.28 (d, J=9 Hz, 2H), 8.07 (s, 1H), 7.31 (d, J=9 Hz, 2H), 6.74 (s, 1H), 4.87 (d, J=8 Hz, 1H), 4.69 (d, J=14 Hz, 1H), 4.42 (dd, J=15 Hz, J=10 Hz, 1H), 1.03 (s, 9H); ES-LCMS m/z 424 (M+H).

Example 7d

Preparation of (1S)-2,2-dimethyl-1-{[3-(trifluoromethyl)-1H-pyrazol-1-yl]methyl}propyl (1S)-1-{[(2-pyridinylsulfonyl)amino]acetyl}pentylcarbamate

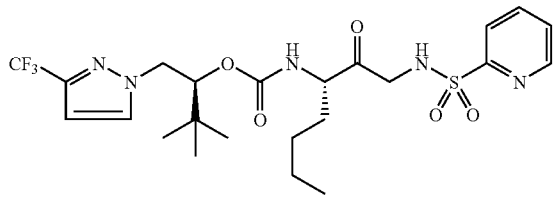

To 102.6 mg (314.3 µmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride at room temperature was added 105.7 mg (105.7 µmol) of 4-nitrophenyl (1S)-2,2-dimethyl-1-{[3-(trifluoromethyl)-1H-pyrazol-1-yl]methyl}propyl carbonate in 2.6 mL of dimethylformamide. This was followed by the addition of 183.5 µL (1.05 mmol) of N,N-diisopropylethylamine. The mixture was stirred for 16 h at room temperature. It was concentrated, and saturated sodium bicarbonate was added, and the mixture was extracted with ethyl acetate. The organic layer was washed with saturated sodium chloride, dried over anhydrous magnesium sulfate, filtered, and concentrated. The residue was purified by silica gel column chromatography eluting with an ethyl acetate:hexanes solution (7:3) to give 90.8 mg (63%) of a mixture of alcohols. The alcohol mixture was dissolved in 3.3 mL of dichloromethane at room temperature, and 87.6 mg (206.5 µmol) of Dess-Martin periodinane was added, and the reaction mixture was stirred for 60 min. It was then poured into saturated sodium metabisulfite, and the resulting mixture was subsequently neutralized with saturated sodium bicarbonate. It was then extracted with ethyl acetate. The organic layer was dried over anhydrous magnesium sulfate, filtered, and concentrated. The residue was purified by silica gel column chromatography eluting with an ethyl acetate:hexanes solution (3:2) to give 61.7 mg (68%) of (1S)-2,2-dimethyl-1-{[3-(trifluoromethyl)-1H-pyrazol-1-yl]methyl}propyl (1S)-1-{[(2-pyridinylsulfonyl)amino]acetyl}pentylcarbamate. $R_f$=0.28 (3:2 ethyl acetate:hexanes); $^1$H-NMR (300 MHz, DMSO-$d_6$, Temp=110° C.): δ 8.63 (d, J=4 Hz, 1H), 8.20 (s, 1H), 8.02 (t, J=8 Hz, 1H), 7.86 (d, J=8 Hz, 1H), 7.77 (s, 1H), 7.60 (dd, J=7 Hz, J=5 Hz, 1H), 7.07 (br s, 1H), 6.53 (s, 1H), 4.82 (d, J=10 Hz, 1H), 4.47 (d, J=14 Hz, 1H), 4.22 (dd, J=14 Hz, J=10 Hz, 1H), 4.14–3.88 (m, 3H), 1.68–1.52 (m, 1H), 1.50–1.34 (m, 1H), 1.36–1.10 (m, 4H), 0.96 (s, 9H), 0.84 (t, J=7 Hz, 3H); HRMS $C_{23}H_{33}F_3N_5O_5S$ m/z 548.2155 (M+H)$_{cal}$; 548.2146 (M+H)$_{obs}$.

Example 8

Preparation of (1S)-2,2-dimethyl-1-{[3-(trifluoromethyl)-1H-pyrazol-1-yl]methyl}propyl (1S)-1-methyl-2-oxo-3-[(2-pyridinylsulfonyl)amino]propylcarbamate

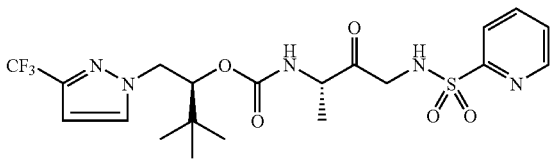

To 178.2 mg (560.0 µmol) of N-[(2S,3S)-3-amino-2-hydroxybutyl]-2-pyridinesulfonamide hydrochloride & N-[(2R,3S)-3-amino-2-hydroxybutyl]-2-pyridinesulfonamide hydrochloride at room temperature was added 244.8 mg (560.0 µmol) of 4-nitrophenyl (1S)-2,2-dimethyl-1-{[3-(trifluoromethyl)-1H-pyrazol-1-yl]methyl}propyl carbonate in 5.6 mL of dimethylformamide. This was followed by the addition of 390.2 µL (2.24 mmol) of N,N-diisopropylethylamine, and the reaction mixture was stirred for 44 h at room temperature. The solution was concentrated, saturated sodium bicarbonate was added, and the resulting mixture was extracted with ethyl acetate. The extract was washed with saturated sodium chloride, dried over anhydrous magnesium sulfate, filtered, and concentrated. The residue was purified by silica gel column chromatography eluting with an ethyl acetate:hexanes solution (4:1) to give 250.2 mg (88%) of a mixture of alcohols. The alcohols were dissolved in 4.9 mL of chloroform at room temperature, 261.4 mg (616.2 µmol) of Dess-Martin periodinane was added, and the reaction mixture was stirred for 45 min. The reaction mixture was poured into saturated sodium metabisulfite. This mixture was subsequently neutralized with saturated sodium bicarbonate, and extracted with ethyl acetate. The organic layer was dried over anhydrous magnesium sulfate, filtered, and concentrated. The residue was purified by silica gel column chromatography eluting with an ethyl acetate:hexanes solution (7:3) to give 164.0 mg (66%) of (1S)-2,2-dimethyl-1-{[3-(trifluoromethyl)-1H-pyrazol-1-yl]methyl}propyl (1S)-1-methyl-2-oxo-3-[(2-pyridinylsulfonyl)amino]propylcarbamate. $R_f$=0.32 (7:3 ethyl acetate:hexanes); $^1$H-NMR (300 MHz, DMSO-$d_6$, Temp=110° C.): δ 8.64 (d, J=5 Hz, 1H), 8.02 (t, J=8 Hz, 1H), 7.87 (d, J=8 Hz, 1H), 7.79 (s, 1H), 7.68–7.58 (m, 1H), 7.60 (dd, J=8 Hz, J=5 Hz, 1H), 7.18–7.04 (m, 1H), 6.57 (s, 1H), 4.79 (d, J=8 Hz, 1H), 4.48 (d, J=14 Hz, 1H), 4.21 (dd, J=14 Hz, J=9 Hz, 1H), 4.15–3.98 (m, 3H), 1.12 (d, J=7 Hz, 3H), 0.95 (s, 9H); HRMS $C_{20}H_{27}F_3N_5O_5S$ m/z 506.1685 (M+H)$_{Cal}$; 506.1680 (M+H)$_{Obs}$.

Example 9

Preparation of (1S)-2,2-dimethyl-1-[5-(trifluoromethyl)-1,3-benzothiazol-2-yl]propyl (1S)-1-{[(2-pyridinylsulfonyl)amino]acetyl}pentylcarbamate

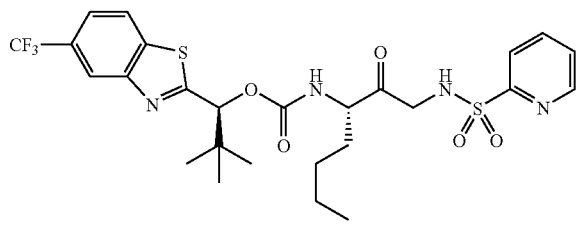

Example 9a

Preparation of 5-(trifluoromethyl)-1,3-benzothiazole

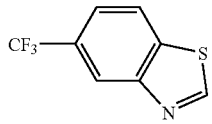

A mixture of 5.1 g (22.2 mmol) of 2-amino-4-(trifluoromethyl) benzenethiol hydrochloride, 5.5 mL (33.3 mmol) of triethylorthoformate, and 2 drops of sulfuric acid was slowly heated to 180° C. over 1 h. The ethanol formed was allowed to escape via a short path distillation still. The reaction mixture was cooled to room temperature and the residue was dissolved in ethyl acetate, washed with saturated sodium bicarbonate, dried over anhydrous magnesium sulfate, and concentrated in vacuo. The residue was purified by silica gel chromatography with ethyl acetate:hexane (1:9) to afford 3.8 g (86%) of 5-(trifluoromethyl)-1,3-benzothiazole as a solid. $^1$H-NMR (400 MHz, DMSO-d$_6$): δ 9.58 (s, 1H), 8.44–8.42 (m, 2H), 7.80 (d, 1H).

Example 9b

Preparation of 2,2-dimethyl-1-[5-(trifluoromethyl)-1,3-benzothiazol-2-yl]-1-propanol

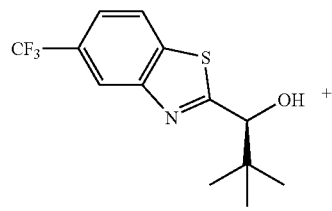

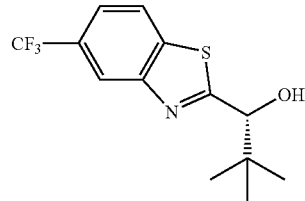

To a stirred solution of 3.8 g (19.0 mmol) of 5-(trifluoromethyl)-1,3-benzothiazole in 30 mL of tetrahydrofuran at −78° C. was added 13.1 mL (21.0 mmol) of a 1.6 M solution of n-butyllithium in hexane over 45 min. Then, 1.8 g (21.0 mmol) of trimethylacetaldehyde in 10 mL of tetrahydrofuran was added dropwise over 30 min. The reaction mixture was stirred for 1 h at −78° C., and then allowed to warm to 0° C. Then, 25 mL of water was added and the mixture was extracted with 80 mL of ether. The ether was washed with 40 mL of water (3×), dried over anhydrous magnesium sulfate, and concentrated in vacuo. The residue was purified by silica gel chromatography eluting with ethyl acetate:hexane (1:9) to afford 1.8 g (33%) of 2,2-dimethyl-1-[5-(trifluoromethyl)-1,3-benzothiazol-2-yl]-1-propanol as an off-white solid. The enantiomers were separated in 98.8% ee using a Chiralpak AD, 10 micron column with a mobile phase of 90% carbon dioxide: 10% methanol and a flow rate of 2.0 mL/minute. $^1$H-NMR (400MHz, DMSO-d$_6$): δ 8.33–8.29 (m, 2H), 7.71 (d, J=8 Hz, 1H), 6.61 (d, J=5 Hz, 1H), 4.60 (d, J=5 Hz, 1H), 0.97 (s, 9H).

Example 9c

Preparation of (1S)-2,2-dimethyl-1-[5-(trifluoromethyl)-1,3-benzothiazol-2-yl]propyl 4-nitrophenyl Carbonate

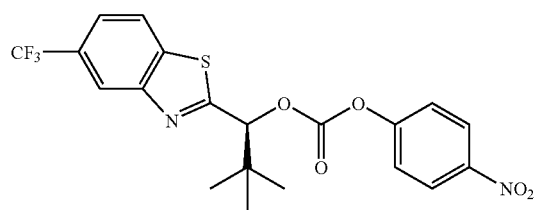

A solution of 715 mg (2.5 mmol) of (1S)-2,2-dimethyl-1-[5-(trifluoromethyl)-1,3-benzothiazol-2-yl]-1-propanol and 0.40 mL (4.9 mmol) of pyridine in 25 mL of dichloromethane was cooled to 5° C. Then, 755 mg (3.7 mmol) of 4-nitrophenylchloroformate was added and the reaction mixture was allowed to warm to ambient temperature. After being stirred for 48 h, the reaction mixture was concentrated in vacuo. The residue was taken up in 80 mL of ethyl acetate, and this solution was washed with 40 mL of water (2×), dried over anhydrous magnesium sulfate, and concentrated. The residue was purified by silica gel chromatography eluting ethyl acetate:hexane (1:9) to afford 835 mg (74%) of (1S)-2,2-dimethyl-1-[5-(trifluoromethyl)-1,3-benzothiazol-2-yl]propyl 4-nitrophenyl carbonate as a white foam. $^1$H-NMR (400 MHz, DMSO$_6$): δ 8.44–8.40 (m, 2H), 8.29 (d, J=7 Hz, 2H), 7.82 (d, J=8 Hz, 1H), 7.57 (d, J=7 Hz, 2H), 5.85 (s, 1H), 1.08 (s, 9H).

Example 9d

Preparation of (1S)-2,2-dimethyl-1-[5-(trifluoromethyl)-1,3-benzothiazol-2-yl]propyl (1S)-1-{[(2-pyridinylsulfonyl)amino]acetyl}pentylcarbamate

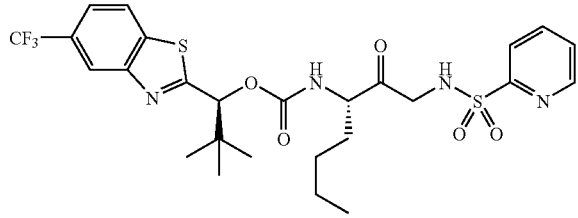

To 100.9 mg (280.0 μmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride at room temperature was added 127.3 mg (280.0 μmol) of 4-nitrophenyl (1S)-2,2-dimethyl-1-[5-(trifluoromethyl)-1,3-benzothiazol-2-yl]propyl carbonate in 2.8 mL of dimethylformamide. This was followed by the addition of 195.1 μL (1.12 mmol) of N,N-diisopropylethylamine, and the reaction mixture was stirred for 14 h at room temperature. The solution was concentrated, saturated sodium bicarbonate was added, and the mixture was extracted with ethyl acetate. The organic layer was washed with saturated sodium chloride, dried over anhydrous magnesium sulfate, filtered, and concentrated. The residue was purified by silica gel column chromatography eluting with an ethyl acetate:hexanes solution (7:3) to give 136.9 mg (81%) of a mixture of alcohols. The alcohols were dissolved in 4.5 mL of dichloromethane at room temperature, and 120.4 mg (283.9 μmol) of Dess-Martin periodinane was added. The reaction mixture was stirred for 60 min before being poured into saturated sodium metabisulfite. The resulting mixture was then neutralized with saturated sodium bicarbonate, before being extracted with ethyl acetate. The organic layer was dried over anhydrous magnesium sulfate, filtered, and concentrated. The residue was purified by silica gel column chromatography eluting with an ethyl acetate:hexanes solution (1:1) to give 71.7 mg (53%) of (1S)-2,2-dimethyl-1-[5-(trifluoromethyl)-1,3-benzothiazol-2-yl]propyl (1S)-1-{[(2-pyridinylsulfonyl)amino]acetyl}pentylcarbamate. $R_f$=0.29 (1:1 ethyl acetate:hexanes); $^1$H-NMR (300 MHz, DMSO-$d_6$, Temp=110° C.): δ 8.63 (d, J=4 Hz, 1H), 8.31 (s, 1H), 8.30 (d, J=7 Hz, 1H), 8.20 (s, 1H), 8.02 (t, J=8 Hz, 1H), 7.87 (d, J=8 Hz, 1H), 7.73 (d, J=9 Hz, 1H), 7.68 (br s, 1H), 7.59 (dd, J=7 Hz, J=5 Hz, 1H), 5.67 (s, 1H), 4.22–4.02 (m, 3H), 1.78–1.64 (m, 1H), 1.64–1.44 (m, 1H), 1.36–1.22 (m, 4H), 1.07 (s, 9H), 0.82 (t, J=6 Hz, 3H); HRMS $C_{26}H_{32}F_3N_4O_5S_2$ m/z 601.1766 (M+H)$_{Cal}$; 601.1759 (M+H)$_{Obs}$.

Example 10

Preparation of (1S)-2,2-dimethyl-1-[5-(trifluoromethyl)-1,3-benzothiazol-2-yl]propyl (1S)-1-methyl-2-oxo-3-[(2-pyridinylsulfonyl)amino]propylcarbamate

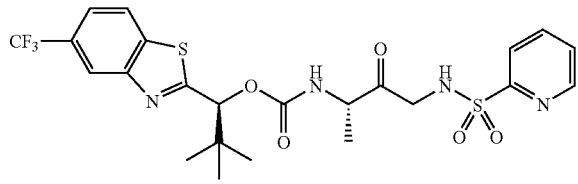

To 76.6 mg (240.6 μmol) of N-[(2S,3S)-3-amino-2-hydroxybutyl]-2-pyridinesulfonamide hydrochloride & N-[(2R,3S)-3-amino-2-hydroxybutyl]-2-pyridinesulfonamide hydrochloride in 2.0 mL of dimethylformamide at room temperature was added 99.4 mg (218.7 μmol) of 4-nitrophenyl (1S)-2,2-dimethyl-1-[5-(trifluoromethyl)-1,3-benzothiazol-2-yl]propyl carbonate in 2.4 mL of dimethylformamide. This was followed by the addition of 152.4 μL (874.9 mmol) of N,N-diisopropylethylamine and the mixture was stirred for 17 h at room temperature. The solution was concentrated, saturated sodium bicarbonate was added, and the mixture was extracted with ethyl acetate. The organic layer was washed with saturated sodium chloride, dried over anhydrous magnesium sulfate, filtered, and concentrated. The residue was purified by silica gel column chromatography eluting with an ethyl acetate:hexanes solution (7:3) to give 114.5 mg (93%) of a mixture of alcohols. The alcohols were dissolved in 5.1 mL of dichloromethane at room temperature and 108.3 mg (255.3 μmol) of Dess-Martin periodinane was added. The reaction mixture was stirred for 60 min, and then poured into saturated sodium metabisulfite. The resulting mixture was neutralized with saturated sodium bicarbonate, and then extracted with ethyl acetate. The organic layer was dried over anhydrous magnesium sulfate, filtered, and concentrated. The residue was purified by silica gel column chromatography eluting with an ethyl acetate:hexanes solution (3:2) to give 81.3 mg (71%) of (1S)-2,2-dimethyl-1-[5-(trifluoromethyl)-1,3-benzothiazol-2-yl]propyl (1S)-1-methyl-2-oxo-3-[(2-pyridinylsulfonyl)amino]propylcarbamate. $R_f$=0.21 (3:2 ethyl acetate:hexanes); $^1$H-NMR (300 MHz, DMSO-$d_6$, Temp=110° C.): δ 8.63 (d, J=5 Hz, 1H), 8.31 (s, 1H), 8.30 (d, J=8 Hz, 1H), 8.21 (s, 1H), 8.03 (t, J=8 Hz, 1H), 7.88 (d, J=8 Hz, 1H), 7.73 (d, J=9 Hz, 1H), 7.71 (br s, 1H), 7.59 (dd, J=7 Hz, J=5 Hz, 1H), 5.67 (s, 1H), 4.26–4.02 (m, 3H), 1.24 (t, J=7 Hz, 3H), 1.07 (s, 9H); HRMS $C_{23}H_{26}F_3N_4O_5S_2$ m/z 559.1297 (M+H)$_{cal}$; 559.1285 (M+H)$_{Obs}$.

Example 11

Preparation of (1S)-2,2-dimethyl-1-({4-[4-(trifluoromethyl)phenyl]-1H-pyrazol-1-yl}methyl)propyl (1S)-1-{[(2-pyridinylsulfonyl)amino]acetyl}pentylcarbamate

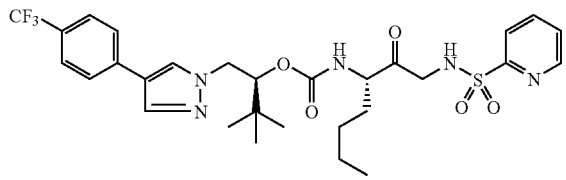

Example 11a

Preparation of 4-[4-(trifluoro)phenyl]-1H-pyrazole

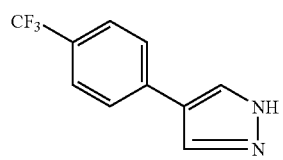

To 13.70 mL (146.95 mmol) of phosphorus oxychloride at 0° C. was added 13.92 mL (179.77 mmol) of anhydrous N,N-dimethylformamide dropwise. The resulting solution was stirred for 15 min at room temperature. Then, 10.00 g (48.98 mmol) of [4-(trifluoromethyl)phenyl]acetic acid in 24 mL of anhydrous N,N-dimethylformamide was added dropwise. The resulting mixture was stirred for 19 h at 70° C., and then poured onto ice. Following neutralization with potassium carbonate, 30 g of sodium hydroxide was added, and the resulting solution was heated at 50° C. for 15 min. It was then cooled to 0° C. and filtered. The filter cake was washed with water and dried under a vacuum to give 3-(dimethylamino)-2-[4-(trifluoromethyl)phenyl]-2-propenal. This dry solid was dissolved in 122 mL of methanol, 3.07 mL (97.97 mmol) of hydrazine was added, and the solution was stirred for 6 h at room temperature. It was poured into water, and the resulting mixture was filtered. The filter cake was washed with water, followed by hexanes, and dried under vacuum to give 8.35 g (80% yield) of 4-[4-(trifluoro)phenyl]-1H-pyrazole. $R_f$=0.26 (1:19 methanol:dichloromethane); $^1$H-NMR (300 MHz, DMSO-$d_6$): δ 13.09 (br s, 1H), 8.34 (s, 1H), 8.04 (s, 1H), 7.82 (d, J=8 Hz, 2H), 7.68 (d, J=8 Hz, 2H); ES-LCMS m/z 213 (M+H).

Example 11b

Preparation of (2S)-3,3-dimethyl-1-{4-[4-(trifluoromethyl)phenyl]-1H-pyrazol-1-yl}-2-butanol

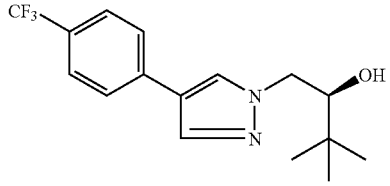

To 2.00 g (19.97 mmol) of (S)-3,3-dimethyl-1,2-epoxybutane in 5.0 mL of ethanol was added 5.08 g (23.96 mmol) of 4-[4-(trifluoro)phenyl]-1H-pyrazole. Then, 3.90 mL (27.96 mmol) of triethylamine was added, and the solution was stirred in a sealed tube at 85° C. for 16 h. It was cooled and concentrated, and the residue was purified by silica gel column chromatography eluting with an ethyl acetate:hexanes solution (3:7) to give 3.30 g (53%) of (2S)-3,3-dimethyl-1-{4-[4-(trifluoromethyl)phenyl]-1H-pyrazol-1-yl}-2-butanol. $R_f$=0.31 (3:7 ethyl acetate:hexanes); $^1$H-NMR (300 MHz, DMSO-$d_6$): δ 8.29 (s, 1H), 7.99 (s, 1H), 7.78 (d, J=8 Hz, 2H), 7.68 (d, J=8 Hz, 2H), 4.93 (d, J=6 Hz, 1H), 4.26 (dd, J=14 Hz, J=2 Hz, 1H), 3.89 (dd, J=14 Hz, J=10 Hz, 1H), 3.49 (dd, J=8 Hz, J=6=Hz, 1H), 0.91 (s, 9H); ES-LCMS m/z 313 (M+H).

Example 11c

Preparation of (1S)-2,2-dimethyl-1-({4-[4-(trifluoromethyl)phenyl]-1H-pyrazol-1-yl}methyl)propyl 4-nitrophenyl Carbonate

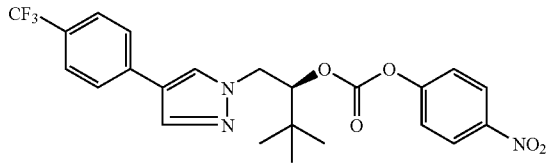

To 3.30 g (10.57 mmol) of (2S)-3,3-dimethyl-1-{4-[4-(trifluoromethyl)phenyl]-1H-pyrazol-1-yl}-2-butanol in 200 mL of tetrahydrofuran at 0° C. was added 7.26 mL (11.62 mmol) of 1.6 M n-butyllithium in hexanes, and the resulting solution was stirred for 10 min. Then, 3.19 g (15.84 mmol) of 4-nitrophenyl chloroformate in 11 mL of tetrahydrofuran was added, and the solution was stirred at room temperature for 75 min. Saturated aqueous sodium bicarbonate was added, and the resulting mixture was extracted with ethyl acetate. The extract was washed with saturated aqueous sodium chloride, dried over anhydrous magnesium sulfate, filtered, and concentrated. The residue was purified by silica gel column chromatography eluting with an ethyl acetate:hexanes solution (3:7) to give 3.92 g (78%) of (1S)-2,2-dimethyl-1-({4-[4-(trifluoromethyl)phenyl]-1H-pyrazol-1-yl}methyl)propyl 4-nitrophenyl carbonate. $R_f$=0.19 (3:7 ethyl acetate:hexanes); $^1$H-NMR (300 MHz, DMSO-$d_6$): δ 8.44 (s, 1H), 8.14 (d, J=9 Hz, 2H), 8.08 (s, 1H), 7.79 (d, J=8 Hz, 2H), 7.70 (d, J=8 Hz, 2H), 7.27 (d, J=9 Hz, 2H), 4.88 (dd, J=10 Hz, J=2 Hz, 1H), 4.61 (d, J=13 Hz, 1H), 4.32 (dd, J=15 Hz, J=10 Hz, 1H), 1.05 (s, 9H); ES-LCMS m/z 478 (M+H).

Example 11d

Preparation of (1S)-2,2-dimethyl-1-({4-[4-(trifluoromethyl)phenyl]-1H-pyrazol-1-yl}methyl)propyl (1S)-1-{[(2-pyridinylsulfonyl)amino]acetyl}pentylcarbamate

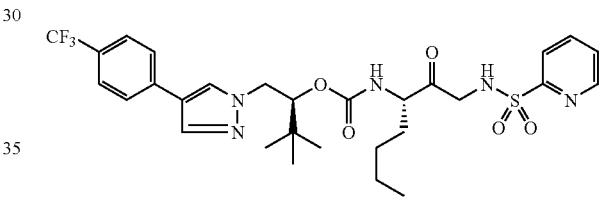

To 103.2 mg (286.7 μmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride at room temperature was added 124.4 mg (260.6 μmol) of (1S)-2,2-dimethyl-1-({4-[4-(trifluoromethyl)phenyl]-1H-pyrazol-1-yl}methyl)propyl 4-nitrophenyl carbonate in 2.6 mL of dimethylformamide. This was followed by the addition of 181.5 μL (1.04 mmol) of N,N-diisopropylethylamine, and the reaction mixture was stirred for 16 h at room temperature. It was then concentrated, saturated sodium bicarbonate was added, and the mixture was extracted with ethyl acetate. The organic layer was washed with saturated sodium chloride, dried over anhydrous magnesium sulfate, filtered, and concentrated. The residue was purified by silica gel column chromatography eluting with an ethyl acetate:hexanes solution (4:1) to give 111.9 mg (69%) of a mixture of alcohols. The alcohols were dissolved in 3.6 mL of dichloromethane at room temperature, 94.8 mg (223.6 mmol) of Dess-Martin periodinane was added, and the reaction mixture was stirred for 120 min. It was poured into saturated sodium metabisulfite, and the resulting mixture was neutralized with saturated sodium bicarbonate and extracted with ethyl acetate. The organic layer was dried over anhydrous magnesium sulfate, filtered, and concentrated. The residue was purified by silica gel column chromatography eluting with an ethyl acetate:hexanes solution (7:3) to give 75.3 mg (68%) of (1S)-2,2-dimethyl-1-({4-[4-(trifluoromethyl)phenyl]-1H-pyrazol-1-yl}methyl)propyl (1S)-1-{[(2-pyridinylsulfonyl)amino]

acetyl}pentylcarbamate. $R_f$=0.27 (7:3 ethyl acetate: hexanes); $^1$H-NMR (300 MHz, DMSO-$d_6$, Temp=110° C.): δ 8.62 (d, J=4 Hz, 1H), 8.10 (s, 1H), 8.02 (t, J=8 Hz, 1H), 7.86 (d, J=6 Hz, 1H), 7.86 (s, 1H), 7.72 (d, J=8 Hz, 2H), 7.63 (d, J=9 Hz, 2H), 7.59 (dd, J=8 Hz, J=5 Hz, 1H), 7.05 (br s, 1H), 4.85 (d, J 9 Hz, 1H), 4.42 (d, J=15 Hz, 1H), 4.16 (dd, J=14 Hz, J=10 Hz, 1H), 4.06 (d, J=4 Hz, 1H), 4.01 (br s, 1H), 4.00–3.86 (m, 1H), 1.64–1.44 (m, 1H), 1.42–1.36 (m, 1H), 1.16–1.04 (m, 4H), 0.97 (s, 9H), 0.68 (t, J=7 Hz, 3H); HRMS $C_{29}H_{37}F_3N_5O_5S$ m/z 624.2468 $(M+H)_{cal}$; 624.2477 $(M+H)_{Obs}$.

Example 12

Preparation of (1S)-2,2-dimethyl-1-({5-[4-(trifluoromethyl)phenyl]-1H-pyrazol-1-yl}methyl)propyl (1S)-1-{[(2-pyridinylsulfonyl)amino]acetyl}pentylcarbamate

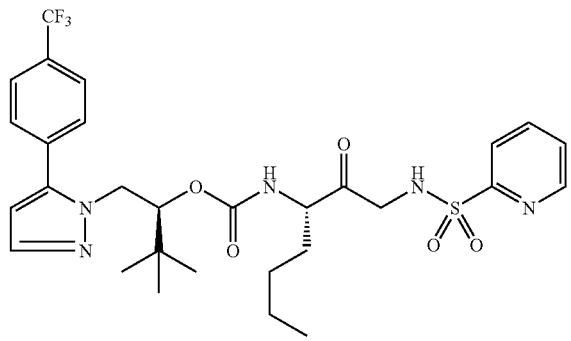

Example 12a

Preparation of 4-nitrophenyl (1S)-2,2-dimethyl-1-({5-[4-(trifluoromethyl)phenyl]-1H-pyrazol-1-yl}methyl)propyl Carbonate

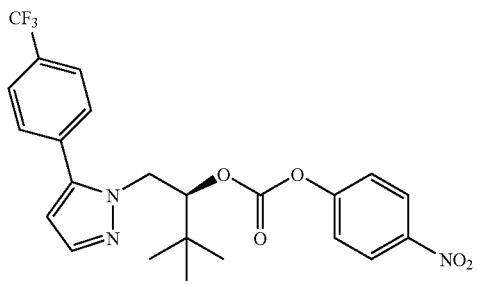

To 562.0 mg (1.80 mmol) of (2S)-3,3-dimethyl-1-{5-[4-(trifluoromethyl)phenyl]-1H-pyrazol-1-yl}-2-butanol in 18 mL of 1,2-dichloroethane at room temperature was added 544.1 mg (2.70 mmol) of 4-nitrophenyl chloroformate. Then, 291.1 μL (3.60 mmol) of pyridine was added, and the solution was heated at reflux for 16 h. Saturated aqueous sodium bicarbonate was added, and the resulting mixture was extracted with ethyl acetate. The extract was dried over anhydrous magnesium sulfate, filtered, and concentrated. The residue was purified by silica gel column chromatography eluting with an ethyl acetate:hexanes solution (3:7) to give 779.7 mg (91%) of 4-nitrophenyl (1S)-2,2-dimethyl-1-({5-[4-(trifluoromethyl)phenyl]-1H-pyrazol-1-yl}methyl) propyl carbonate. $R_f$=0.21 (3:7 ethyl acetate:hexanes); $^1$H-NMR (300 MHz, DMSO-$d_6$): δ 8.29 (d, J=8 Hz, 2H), 7.87 (d, J=8 Hz, 2H), 7.73 (d, J=8 Hz, 2H), 7.63 (s, 1H), 7.33 (d, J=9 Hz, 2H), 6.52 (s, 1H), 4.71 (d, J=9 Hz, 1H), 4.64 (d, J=15 Hz, 1H), 4.33 (dd, J=15 Hz, J=10 Hz, 1H), 0.89 (s, 9H); ES-LCMS m/z 478 (M+H).

Example 12b

Preparation of (1S)-2,2-dimethyl-1-({5-[4-(trifluoromethyl)phenyl]-1H-pyrazol-1-yl}methyl)propyl (1S)-1-{[(2-pyridinylsulfonyl)amino]acetyl}pentylcarbamate

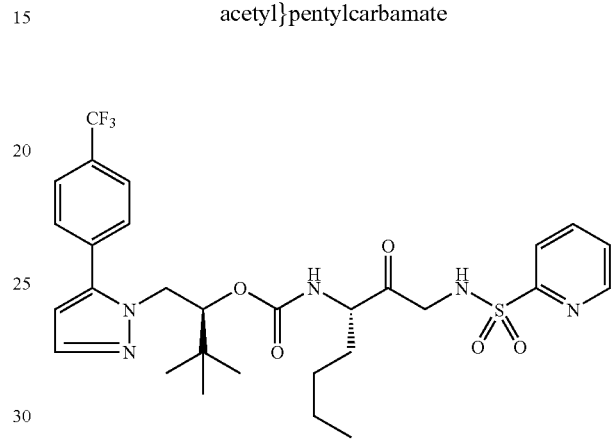

To 96.6 mg (268.2 μmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride at room temperature was added 116.4 mg (243.8 μmol) of 4-nitrophenyl (1S)-2,2-dimethyl-1-({5-[4-(trifluoromethyl)phenyl]-1H-pyrazol-1-yl}methyl)propyl carbonate in 4.9 mL of dimethylformamide. This was followed by the addition of 169.9 μL (975.2 μmol) of N,N-diisopropylethylamine, and the reaction mixture was stirred for 19 h at room temperature. The solution was concentrated, saturated sodium bicarbonate was added, and the resulting mixture was extracted with ethyl acetate. The organic layer was washed with saturated sodium chloride, dried over anhydrous magnesium sulfate, filtered, and concentrated. The residue was purified by silica gel column chromatography eluting with an ethyl acetate:hexanes solution (9:1) to give 93.2 mg (61%) of a mixture of alcohols. The alcohols were dissolved in 3.0 mL of dichloromethane at room temperature, 79.0 mg (186.2 μmol) of Dess-Martin periodinane was added, and the reaction mixture was stirred for 120 min. It was poured into saturated sodium metabisulfite, and the resulting mixture was neutralized with saturated sodium bicarbonate and extracted with ethyl acetate. The organic layer was dried over anhydrous magnesium sulfate, filtered, and concentrated. The residue was purified by silica gel column chromatography eluting with an ethyl acetate:hexanes solution (7:3) to give 42.2 mg (45%) of (1S)-2,2-dimethyl-1-({5-[4-(trifluoromethyl)phenyl]-1H-pyrazol-1-yl}methyl)propyl (1S)-1-{[(2-pyridinylsulfonyl)amino]acetyl}pentylcarbamate. $R_f$=0.24 (7:3 ethyl acetate:hexanes); $^1$H-NMR (300 MHz, DMSO-$d_6$, Temp=110° C.):δ 8.61 (d, J=4 Hz, 1H), 8.02 (t, J=8 Hz, 1H), 7.86 (d, J=8 Hz, 1H), 7.81 (d, J=8 Hz, 2H), 7.72 (d, J=9 Hz, 2H), 7.62 (br s, 1H), 7.61 (dd, J=8 Hz, J=5 Hz, 1H), 7.43 (s, 1H), 7.03 (br s, 1H), 6.34 (s, 1H), 4.79 (d, J=9 Hz, 1H), 4.39 (d, J=14 Hz, 1H), 4.15 (dd, J=13 Hz, J=11 Hz, 1H), 4.10–3.90 (ABX, 2H), 3.90–3.86 (m, 1H), 1.66-1.52 (m, 1H), 1.48–1.30 (m, 1H), 1.28–1.08 (m, 4H), 0.83 (s, 9H), 0.81 (t, J=7 Hz, 3H); HRMS $C_{29}H_{37}F_3N_5O_5S$ m/z 624.2468 (M+H)$_{cal}$; 624.2474 (M+H)$_{Obs}$.

Example 13

Preparation of (1S)-2,2-dimethyl-1-{[3-(3-pyridinyl)-1H-pyrazol-1-yl]methyl}propyl (1S)-1-{[(2-pyridinylsulfonyl)amino]acetyl}pentylcarbamate

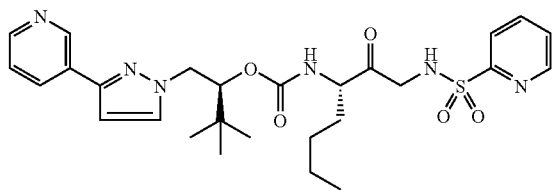

Example 13a

Preparation of 3-(1H-pyrazol-3-yl)pyridine

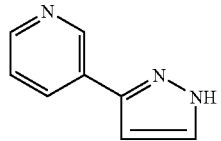

A solution of 5.0 g (41.3 mmol) of 3-acetylpyridine and 5.4 g (45.4 mmol) of dimethyl formamide dimethylacetal in 40 mL of anhydrous dimethylformamide was stirred at 130° C. for 4 h. Solvent was evaporated, and the residue was triturated with diethyl ether to obtain 5.7 g of a yellow solid. To a solution of the solid in 50 mL of methanol was added 1.59 g (32 mmol) of hydrazine monohydrate. After 48 h at room temperature, solvent was removed and portions of acetonitrile were distilled from the residue to provide 4.8 g (81%) of 3-(1H-Pyrazol-3-yl)pyridine as a tan oil. $^1$H-NMR (DMSO-d$_6$):δ 11.5 (br s, 1H), 9.05 (d, J=2 Hz, 1H), 8.56 (dd, J=5 Hz, J=2 Hz, 1H), 8.10 (dt, J=8 Hz, J=2 Hz, 1H), 7.65 (d, J=2 Hz, 1H), 7.33 (dd, J=8 Hz, J=5 Hz, 1H) 6.66 (d, J=2 Hz, 1H); ES-LCMS m/z 2146 (M+H).

Example 13b

Preparation of (2S)-3,3-dimethyl-1-[3-(3-pyridinyl)-1H-pyrazol-1-yl]-2-butanol

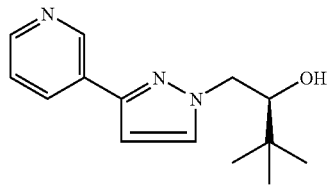

To a solution of 0.38 g (2.62 mmol) of 3-(1H-pyrazol-3-yl)pyridine and 0.47 g (2.62 mmol) of (4S)-4-tert-butyl-1,3,2-dioxathiolane 2,2-dioxide in 15 mL of acetonitrile was added 1.3 g of a potassium fluoride/alumina mixture [prepared by mixing 10 g of potassium fluoride, 200 mL of water, and 15 g of activated neutral alumina (Brockmann I, 150 mesh) and concentrating at 55° C.]. The mixture was stirred at ambient temperature for 4 h. Then, a solution of 2 mL of acetyl chloride in 10 mL of methanol was added to the reaction mixture. After 18 h, saturated aqueous sodium bicarbonate was added, the mixture was filtered, and the filter cake was rinsed with methanol. The filtrate was concentrated, and the residue was partitioned between saturated aqueous sodium bicarbonate and dichloromethane. The organic phase was dried over sodium sulfate and concentrated to provide 0.6 g (94%) of (2S)-3,3-dimethyl-1-[3-(3-pyridinyl)-1H-pyrazol-1-yl]-2-butanol as a yellow solid. $^1$H-NMR (DMSO-d$_6$): δ 8.97 (s, 1H), 8.45 (d, J=4 Hz, 1H), 8.1 (t, J=8 Hz, 1H), 7.76 (d, J=2 Hz, 1H), 7.38 (dd, J=8 Hz, J=5 Hz, 1H), 4.86 (d, J=6 Hz, 1H), 4.27 (dd, J=13 Hz, J=2 Hz, 1H), 3.90 (dd, J=14 Hz, J=10 Hz, 1H), 3.5–3.4 (m, 1H), 0.90(s, 9H).

Example 13c

Preparation of (1S)-2,2-Dimethyl-1-{[3-(3-pyridinyl)-1H-pyrazol-1-yl]methyl}propyl 4-nitrophenyl Carbonate

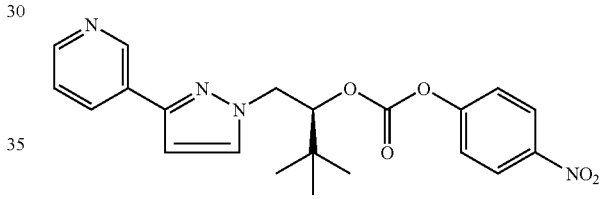

(2S)-3,3-Dimethyl-1-[3-(3-pyridinyl)-1H-pyrazol-1-yl]-2-butanol was treated with p-nitrophenyl chloroformate as previously described in example 1g to provide the title compound as a solid foam. $^1$H-NMR (DMSO-d$_6$): δ 8.97 (s, 1H), 8.46 (d, J=4 Hz, 1H), 8.13 (d, J=9 Hz, 2H), 8.10 (d, J=8 Hz, 1H), 7.9 (d, J=2 Hz, 1H), 7.38 (dd, J=7 Hz, J=4 Hz, 1H), 7.22 (d, J=9 Hz, 2H), 6.83 (d, J=2 Hz, 1H), 4.90 (d, J=9 Hz, 1H), 4.62 (d, J=14 Hz, 1H), 4.35 (dd, J=14 Hz, J=9 Hz, 1H), 1.03 (s, 9H).

Example 13d

Preparation of (1S)-2,2-dimethyl-1-{[3-(3-pyridinyl)-1H-pyrazol-1-yl]methyl}propyl (1S)-1-{[(2-pyridinylsulfonyl)amino]acetyl}pentylcarbamate

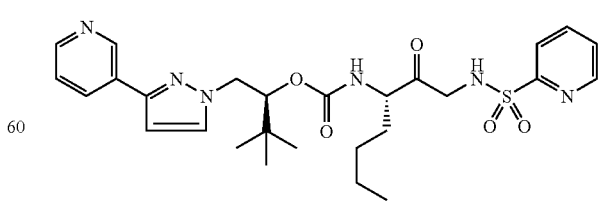

To 129.4 mg (359.1 μmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride at room temperature was added 134.0 mg (326.5 μmol) of (1S)-2,2-dimethyl-1-{[3-(3-pyridinyl)-1H-pyrazol-1-yl]methyl}propyl 4-nitrophenyl carbonate in 6.5 mL of dimethylformamide. This was followed by the addition of 227.5 μL (1.31 mmol) of N,N-diisopropylethylamine, and the reaction mixture was stirred for 23 h at room temperature. It was concentrated, saturated sodium bicarbonate was added, and the resulting mixture was extracted with ethyl acetate. The organic layer was washed with saturated sodium chloride, dried over anhydrous magnesium sulfate, filtered, and concentrated. The residue was purified by silica gel column chromatography eluting with methanol:ethyl acetate (1:19) to give 138.8 mg (76%) of a mixture of alcohols. The alcohols were dissolved in 4.9 mL of chloroform at room temperature, 131.7 mg (310.5 μmol) of Dess-Martin periodinane was added, and the reaction mixture was stirred for 60 min. It was poured into saturated sodium metabisulfite, and the resulting mixture was subsequently neutralized with saturated sodium bicarbonate before being extracted with ethyl acetate. The organic layer was dried over anhydrous magnesium sulfate, filtered, and concentrated. The residue was purified by silica gel column chromatography eluting with ethyl acetate with 1% methanol solution to give 91.6 mg (66%) of (1S)-2,2-dimethyl-1-{[3-(3-pyridinyl)-1H-pyrazol-1-yl]methyl}propyl (1S)-1-{[(2-pyridinylsulfonyl)amino]acetyl}pentylcarbamate. $R_f$=0.19 (ethyl acetate); $^1$H-NMR (300 MHz, DMSO-$d_6$, Temp=110° C.): δ 8.94 (s, 1H), 8.62 (d, J=4 Hz, 1H), 8.46 (d, J=3 Hz, 1H), 8.06 (d, J=10 Hz, 1H), 8.00 (d, J=8 Hz, 1H), 7.86 (d, J=8 Hz, 1H), 7.66 (d, J=2 Hz, 1H), 7.60 (d, J=6 Hz, 1H), 7.58 (d, J=5 Hz, 1H), 7.36 (dd, J=8 Hz, J=5 Hz, 1H), 7.05 (br s, 1H), 6.65 (d, J=2 Hz, 1H), 4.88 (d, J=9 Hz, 1H), 4.45 (dd, J=14 Hz, J=3 Hz, 1H), 4.19 (dd, J=14 Hz, J=10 Hz, 1H), 4.11 (d, J=6 Hz, 1H), 4.05 (d, J=6 Hz, 1H), 4.00–3.86 (m, 1H), 1.66–1.48 (m, 1H), 1.48–1.30 (m, 1H), 1.24–1.08 (m, 4H), 0.98 (s, 9H), 0.77 (t, J=6 Hz, 3H); HRMS $C_{27}H_{37}N_6O_5S$ m/z 557.2546 (M+H)$_{Cal}$; 557.2561 (M+H)$_{Obs}$.

Example 14

Preparation of (1S)-2,2-dimethyl-1-{[3-(4-pyridinyl)-1H-pyrazol-1-yl]methyl}propyl (1S)-1-{[(2-pyridinylsulfonyl)amino]acetyl}pentylcarbamate

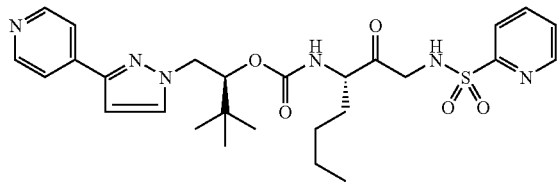

Example 14a

Preparation of (1S)-2,2-dimethyl-1-{[3-(4-pyridinyl)-1H-pyrazol-1-yl]methyl}propyl 4-nitrophenyl Carbonate

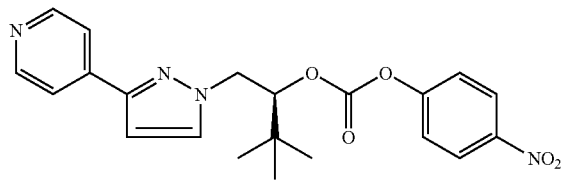

4-Acetylpyridine was subjected sequentially to the procedures described in examples 13a, 13b, & 13c to provide the title compound as a solid foam. $^1$H-NMR (DMSO-$d_6$): δ 8.53 (d, J=6 Hz, 2H), 8:14 (d, J=9 Hz, 2H), 7.93 (d, J=2 Hz, 1H), 7.71 (d, J=6 Hz, 2H), 7.23 (d, J=9 Hz, 2H), 6.9 (d, J=2 Hz, 1H), 4.89 (d, 10 Hz, 1H), 4.65 (br d, J=14 Hz, 1H), 4.37 (dd, J=14 Hz, J=10 Hz, 1H), 1.04 (s, 9H).

Example 14b

Preparation of (1S)-2,2-dimethyl-1-{[3-(4-pyridinyl)-1H-pyrazol-1-yl]methyl}propyl (1S)-1-{[(2-pyridinylsulfonyl)amino]acetyl}pentylcarbamate

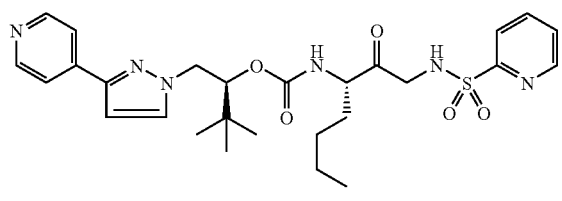

To 123.6 mg (343.1 μmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride at room temperature was added 128.0 mg (311.9 μmol) of (1S)-2,2-dimethyl-1-{[3-(4-pyridinyl)-1H-pyrazol-1-yl]methyl}propyl 4-nitrophenyl carbonate in 6.2 mL of dimethylformamide. This was followed by the addition of 217.3 μL (1.25 mmol) of N,N-diisopropylethylamine, and the reaction mixture was stirred for 64 h at room temperature. It was concentrated, saturated sodium bicarbonate was added, and the resulting mixture was extracted with ethyl acetate. The organic layer was washed with saturated sodium chloride, dried over anhydrous magnesium sulfate, filtered, and concentrated. The residue was purified by silica gel column chromatography eluting with methanol:ethyl acetate (1:9) to give 159.1 mg (91%) of a mixture of alcohols. The alcohols were dissolved in 5.7 mL of chloroform at room temperature, 151.0 mg (355.0 μmol) of Dess-Martin periodinane was added, and the reaction mixture was stirred for 60 min. It was poured into saturated sodium metabisulfite, and the resulting mixture subsequently neutralized with saturated sodium bicarbonate before being extracted with ethyl acetate. The organic layer was dried over anhydrous magnesium sulfate, filtered, and concentrated. The residue was purified by silica gel column chromatography eluting with methanol:ethyl acetate (1:19) to give 53.4 mg (34%) of (1S)-2,2-dimethyl-1-{[3-(4-pyridinyl)-1H-pyrazol-1-yl]methyl}propyl (1S)-1-{[(2-pyridinylsulfonyl)amino]acetyl}pentylcarbamate. $R_f$=0.32 (1:19 methanol:ethyl acetate); $^1$H-NMR (300 MHz, DMSO-$d_6$, Temp=110° C.): δ 8.62 (d, J=5 Hz, 1H), 8.53 (d, J=5 Hz, 2H), 8.01 (t, J=8 Hz, 1H), 7.85 (d, J=8 Hz, 1H), 7.69 (s, 1H), 7.68 (d, J=5 Hz, 2H), 7.60 (d, J=6 Hz, 1H), 7.58 (d, J=6 Hz, 1H), 7.07 (br s, 1H), 6.73 (d, J=2 Hz, 1H), 4.87 (d, J=9 Hz, 1H), 4.46 (dd, 3J=17 Hz, 1H), 4.20 (dd, J=15 Hz, J=10 Hz, 1H), 4.12–3.94 (ABX, 2H), 3.92 (m, 1H), 1.66–1.50 (m, 1H), 1.50–1.30 (m, 1H), 1.28–1.08 (m, 4H), 0.97 (s, 9H), 0.77 (t, J=7 Hz, 3H); HRMS $C_{27}H_{37}N_6O_5S$ m/z 557.2546 (M+H)$_{Cal}$; 557.2542 (M+H)$_{Obs}$.

Example 15

Preparation of (1S)-1-[(5,6-dichloro-1H-benzimidazol-1-yl)methyl]-2,2-dimethylpropyl (1S)-1-{[(2-pyridinylsulfonyl)amino]acetyl}pentylcarbamate

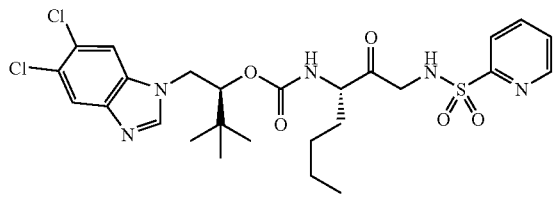

Example 15a

Preparation of (2S)-1-(5,6-dichloro-1H-benzimidazol-1-yl)-3,3-dimethyl-2-butanol

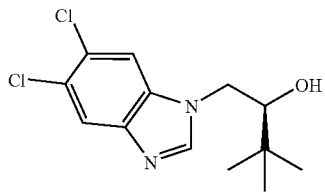

A solution of 2.08 g (11.1 mmol) of 5,6-dichloro-1H-benzimidazole and 2.00 g (11.1 mmol) of (4S)-4-tert-butyl-1,3,2-dioxathiolane 2,2-dioxide in 28 mL of N,N-dimethylformamide was stirred as 1.57 g (11.4 mmol) of potassium carbonate was added. The mixture was stirred at 60° C. for 18 h, and then cooled in an ice bath. A solution of 12 mL of acetyl chloride in 120 mL of methanol was then added. The reaction mixture was stirred for one day, and concentrated. The residue was partitioned between ethyl acetate and saturated aqueous sodium bicarbonate. The organic phase was concentrated, and the residue was slurried in ethyl acetate. The solid was isolated by filtration to yield 1.88 g of (2S)-1-(5,6-dichloro-1H-benzimidazol-1-yl)-3,3-dimethyl-2-butanol. The filtrate was concentrated, and the residue was purified by silica gel column chromatography eluting with ethyl acetate to yield an additional 0.50 g (total yield 2.38 g, 74%) of the title compound. $^1$H-NMR (300 MHz, DMSO-$d_6$): δ 8.29 (d, J=8 Hz, 2H), 7.90 (s, 1H), 7.86 (s, 1H), 4.96 (d, J=6 Hz, 1H), 4.39 (dd, J=14 Hz, J=2 Hz, 1H), 3.98 (dd, J=14 Hz, J=10 Hz, 1H), 3.32 (m, overlapping H$_2$O), 0.95 (s, 9H).

Example 15b

Preparation of (1S)-1-[(5,6-dichloro-1H-benzimidazol-1-yl)methyl]-2,2-dimethylpropyl 4-nitrophenyl Carbonate

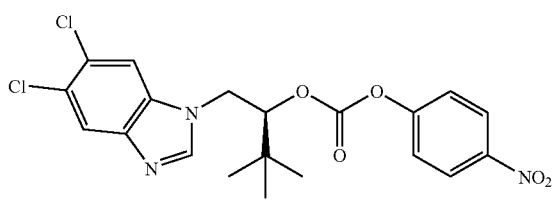

A solution of 2.38 g (8.29 mmol) of (2S)-1-(5,6-dichloro-1H-benzimidazol-1-yl)-3,3-dimethyl-2-butanol and 1.36 mL (16.6 mmol) of pyridine in 83 mL of 1,2-dichloroethane was stirred as 3.34 g (16.6 mmol) of 4-nitrophenylchloroformate was added. The solution was stirred at 95° C. for one day, and then partitioned between ethyl acetate and saturated aqueous sodium bicarbonate. The organic phase was washed with brine, and concentrated. The residue was purified by silica gel column chromatography eluting with ethyl acetate to yield 1.68 g (sample contains 0.33 EtOAc by $^1$H-NMR for an effective weight of 1.58 g, 42%) of (1S)-1-[(5,6-dichloro-1H-benzimidazol-1-yl)methyl]-2,2-dimethylpropyl 4-nitrophenyl carbonate. $^1$H-NMR (300 MHz, DMSO-$d_6$): δ 8.44 (s, 1H), 8.20 (d, J=9 Hz, 2H), 8.01(s, 1H), 7.96 (s, 1H), 6.94 (d, J=9 Hz, 2H), 4.85 (m, 1H), 4.74 (m, 1H), 4.57 (m, 1H), 1.09 (s, 9H); ES-LCMS m/z 452 (M+H)$^+$ retention time=4.33 min.

Example 15c

Preparation of (1S)-1-[(5,6-dichloro-1H-benzimidazol-1-yl)methyl]-2,2-dimethylpropyl (1S)-1-{(1R)-1-hydroxy-2-[(2-pyridinylsulfonyl)amino]ethyl}pentylcarbamate & (1S)-1-[(5,6-dichloro-1H-benzimidazol-1-yl)methyl]-2,2-dimethylpropyl (1S)-1-{(1S)-1-hydroxy-2-[(2-pyridinylsulfonyl)amino]ethyl}pentylcarbamate

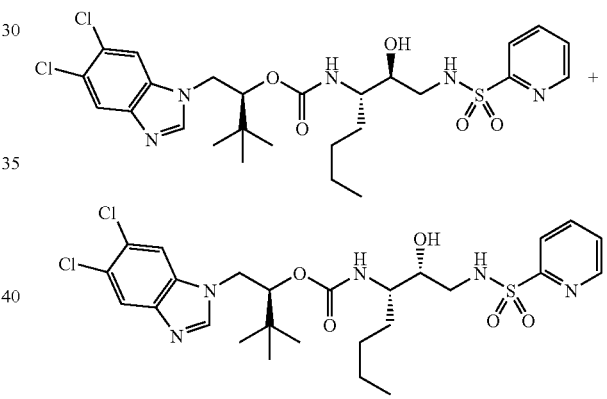

73 mg (0.18 mmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide hydrochloride was slurried in 3.5 mL of anhydrous dimethylformamide. Addition of 80 mg (0.18 mmol) of (1S)-1-[(5,6-dichloro-1H-benzimidazol-1-yl)methyl]-2,2-dimethylpropyl 4-nitrophenyl carbonate followed by 0.14 mL (0.72 mmol) of diisopropylethylamine resulted in a light yellow solution, which was stirred for 3 d. It was then concentrated under reduced pressure. The resulting residue was dissolved in ethyl acetate, and the solution was washed with a saturated aqueous sodium bicarbonate solution., dried over anhydrous magnesium sulfate, filtered, and concentrated. The residue was purified by silica gel chromatography eluting with a methanol:chloroform solution (1:9) to afford 54 mg (50%) of (1 S)-1-[(5,6-dichloro-1H-benzimidazol-1-yl)methyl]-2,2-dimethylpropyl (1S)-1-{(1R)-1-hydroxy-2-[(2-pyridinylsulfonyl)amino]ethyl}pentylcarbamate & (1S)-1-[(5,6-dichloro-1H-benzimidazol-1-yl)methyl]-2,2-dimethylpropyl (1S)-1-{(1S)-1-hydroxy-2-[(2-pyridinylsulfonyl)amino]ethyl}pentylcarbamate. ES-LCMS n/z 622 (M+Na) retention time=3.96 min.

Example 15d

Preparation of (1S)-1-[(5,6-dichloro-1H-benzimidazol-1-yl)methyl]-2,2-dimethylpropyl (1S)-1-{[(2-pyridinylsulfonyl)amino]acetyl}pentylcarbamate

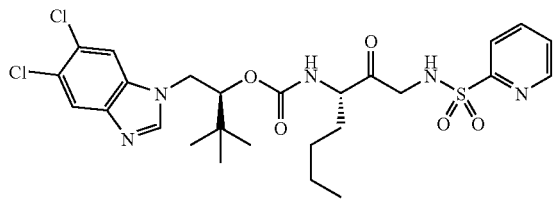

To a solution of 50.5 mg (0.084 mmol) of (1S)-1-[(5,6-dichloro-1H-benzimidazol-1-yl)methyl]-2,2-dimethylpropyl (1S)-1-{(1R)-1-hydroxy-2-[(2-pyridinylsulfonyl)amino]ethyl}pentylcarbamate & (1S)-1-[(5,6-dichloro-1H-benzimidazol-1-yl)methyl]-2,2-dimethylpropyl (1S)-1-{(1S)-1-hydroxy-2-[(2-pyridinylsulfonyl)amino]ethyl}pentylcarbamate in 2.2 mL of chloroform was added 44.6 mg (0.105 mmol) of Dess-Martin periodinane. The mixture was stirred at room temperature for 1.25 h, and then diluted with ethyl acetate. A saturated aqueous sodium thiosulfate solution was added, and the two layers were mixed vigorously before a saturated aqueous solution of sodium bicarbonate was added. The organic phase was dried over anhydrous magnesium sulfate and concentrated. The residue was purified by silica gel column chromatography eluting with a hexane:acetone solution (1:1) to yield 19 mg (38%) of (1S)-1-[(5,6-dichloro-1H-benzimidazol-1-yl)methyl]-2,2-dimethylpropyl (1S)-1-{[(2-pyridinylsulfonyl)amino]acetyl}pentylcarbamate. ES-LCMS m/z 598 (M+H)$^+$ retention time=4.00 min. HRMS $C_{26}H_{33}Cl_2N_5O_5S$ m/z 598.1658 (M+H)$_{Cal}$; 598.1674 (M+H)$_{Obs}$.

Example 16

Preparation of (1S)-1-[(5,6-dichloro-1H-benzimidazol-1-yl)methyl]-2,2-dimethylpropyl (1S)-1-methyl-2-oxo-3-[(2-pyridinylsulfonyl)amino]propylcarbamate

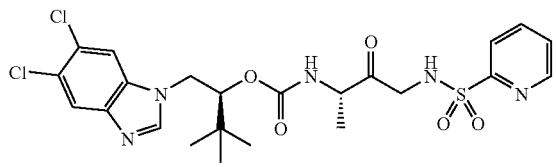

Example 16a

Preparation of (1S)-1-[(5,6-dichloro-1H-benzimidazol-1-yl)methyl]-2,2-dimethylpropyl (1S,2S)-2-hydroxy-1-methyl-3-[(2-pyridinylsulfonyl)amino]propylcarbamate & (1S)-1-[(5,6-dichloro-1H-benzimidazol-1-yl)methyl]-2,2-dimethylpropyl (1S,2R)-2-hydroxy-1-methyl-3-[(2-pyridinylsulfonyl)amino]propylcarbamate

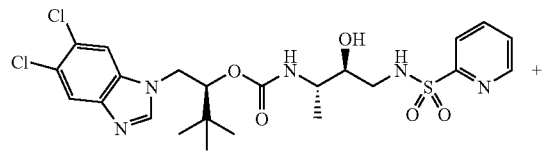 +

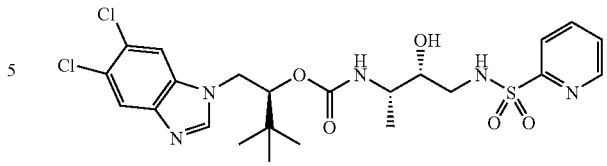

To a solution of 386 mg (1.12 mmol) of tert-butyl (1S,2R)-2-hydroxy-1-methyl-3-[(2-pyridinylsulfonyl)amino]propylcarbamate & tert-butyl (1S,2S)-2-hydroxy-1-methyl-3-[(2-pyridinylsulfonyl)amino]propylcarbamate in 3.3 mL of anhydrous dioxane was added 20 mL of a 4 N solution of hydrogen chloride in dioxane, and the resulting solution was stirred for 60 min, during which a white precipitate formed. The mixture was concentrated, leaving a white solid which was dried under vacuum, and then slurried in 3 mL of anhydrous dimethylformamide. Addition of 0.44 mL (2.24 mmol) of diisopropylethylamine resulted in a light yellow solution, to which 200 mg (0.44 mmol) of (1S)-1-[(5,6-dichloro-1H-benzimidazol-1-yl)methyl]-2,2-dimethylpropyl 4-nitrophenyl carbonate was added. The resulting solution was stirred for 1 d, and then concentrated. The residue was diluted with ethyl acetate, and the resulting solution was washed with a saturated aqueous sodium bicarbonate solution. After drying over magnesium sulfate, volatiles were removed under vacuum, and the residue was purified by silica gel chromatography eluting with a methanol:chloroform solution (1:9) to afford 0.14 g (57%) of (1S)-1-[(5,6-dichloro-1H-benzimidazol-1-yl)methyl]-2,2-dimethylpropyl (1S,2S)-2-hydroxy-1-methyl-3-[(2-pyridinylsulfonyl)amino]propylcarbamate & (1S)-1-[(5,6-dichloro-1H-benzimidazol-1-yl)methyl]-2,2-dimethylpropyl (1S,2R)-2-hydroxy-1-methyl-3-[(2-pyridinylsulfonyl)amino]propylcarbamate. ES-LCMS m/z 558 (M+H) retention time=3.52 min.

Example 16b

Preparation of (1S)-1-[(5,6-dichloro-1H-benzimidazol-1-yl)methyl]-2,2-dimethylpropyl (1S)-1-methyl-2-oxo-3-[(2-pyridinylsulfonyl)amino]propylcarbamate

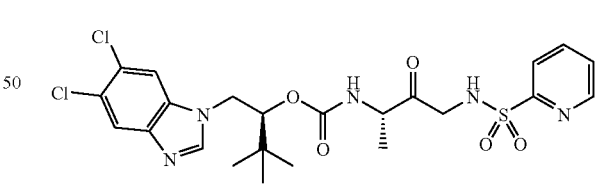

To a solution of 0.13 g (0.23 mmol) of (1S)-1-[(5,6-dichloro-1H-benzimidazol-1-yl)methyl]-2,2-dimethylpropyl (1S,2S)-2-hydroxy-1-methyl-3-[(2-pyridinylsulfonyl)amino]propylcarbamate & (1S)-1-[(5,6-dichloro-1H-benzimidazol-1-yl)methyl]-2,2-dimethylpropyl (1S,2R)-2-hydroxy-1-methyl-3-[(2-pyridinylsulfonyl)amino]propylcarbamate in 6 mL of chloroform was added 42 mg (0.1 mmol) of Dess-Martin periodinane, and the reaction mixture was stirred at room temperature for 1.25 h. The mixture was diluted with ethyl acetate and saturated aqueous sodium thiosulfate solution. The layers were mixed vigorously, and then a saturated aqueous sodium bicarbonate solution was added. The layers were separated, and the organic extract was dried over anhydrous magnesium sulfate and concentrated. The residue was purified by silica gel column chromatography eluting with a methanol:chloroform solution (1:9) to yield 64 mg (50%) of (1S)-1-[(5,6-dichloro-1H-benzimidazol-1-yl)methyl]-2,2-dimethylpropyl (1S)-1-methyl-2-oxo-3-[(2-pyridinylsulfonyl)amino]propylcarbamate ES-LCMS m/z 556 (M+H)$^+$ retention time=3.66 min. HRMS $C_{23}H_{27}Cl_2N_5O_5S$ m/z 556.1188 (M+H)$_{Cal}$; 556.1193 (M+H)$_{Obs}$.

Example 17

Preparation of (1S)-1-[(5,6-dichloro-1H-benzimidazol-1-yl)methyl]-2,2-dimethylpropyl 2-oxo-3-[(2-pyridinylsulfonyl)amino]propylcarbamate

Example 17a

Preparation of (1S)-1-[(5,6-dichloro-1H-benzimidazol-1-yl)methyl]-2,2-dimethylpropyl (2S)-2-hydroxy-3-[(2-pyridinylsulfonyl)amino]propylcarbamate & (1S)-1-[(5,6-dichloro-1H-benzimidazol-1-yl)methyl]-2,2-dimethylpropyl (2R)-2-hydroxy-3-[(2-pyridinylsulfonyl)amino]propylcarbamate

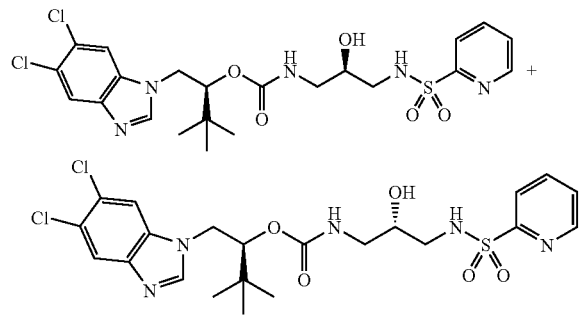

To a solution of 370 mg (1.12 mmol) of tert-butyl (2S)-2-hydroxy-3-[(2-pyridinylsulfonyl)amino]propylcarbamate & tert-butyl (2R)-2-hydroxy-3-[(2-pyridinylsulfonyl)amino]propylcarbamate in 3.3 mL of anhydrous dioxane, 20 mL of a 4 N solution of hydrogen chloride in dioxane was added. The resulting solution was stirred for 60 min, during which time a white precipitate formed. The mixture was concentrated under reduced pressure and the resulting solid was dried under vacuum. A 54 mg (0.18mmol) sample of the residue was then added to a solution of 90 mg (0.2 mmol) of (1S)-1-[(5,6-dichloro-1H-benzimidazol-1-yl)methyl]-2,2-dimethylpropyl 4-nitrophenyl carbonate in 2 mL of dimethylformamide. Addition of 0.22 mL (1.12 mmol) of diisopropylethylamine resulted in a light yellow solution, which was stirred for 1 d under nitrogen, and then concentrated. The residue was then partition between ethyl acetate and a saturated aqueous sodium bicarbonate solution. The layers were separated and the organic phase was dried over anhydrous magnesium sulfate and concentrated. The residue was purified by silica gel chromatography eluting with a methanol:chloroform solution (1:9) to afford 44 mg (45%) of (1S)-1-[(5,6-dichloro-1H-benzimidazol-1-yl)methyl]-2,2-dimethylpropyl (2S)-2-hydroxy-3-[(2-pyridinylsulfonyl)amino]propylcarbamate & (1s)-1-[(5,6-dichloro-1H-benzimidazol-1-yl)methyl]-2,2-dimethylpropyl (2R)-2-hydroxy-3-[(2-pyridinylsulfonyl)amino]propylcarbamate. ES-LCMS m/z 544 (M+H) retention time=3.60 min.

Example 17b

Preparation of (1S)-1-[(5,6-dichloro-1H-benzimidazol-1-yl)methyl]-2,2-dimethylpropyl 2-oxo-3-[(2-pyridinylsulfonyl)amino]propylcarbamate To a solution of 43 mg (0.079 mmol) of (1S)-1-[(5,6-dichloro-1H-benzimidazol-1-yl)methyl]-2,2-dimethylpropyl (2S)-2-hydroxy-3-[(2-pyridinylsulfonyl)amino]propylcarbamate & (1S)-1-[(5,6-dichloro-1H-benzimidazol-1-yl)methyl]-2,2-dimethylpropyl (2R)-2-hydroxy-3-[(2-pyridinylsulfonyl)amino]propylcarbamate in 2 mL of chloroform was added 42 mg (0.1 mmol) of Dess-Martin periodinane, and the mixture was stirred at room temperature for 1.25 h. An additional portion of 21 mg (0.05 mmol) of Dess-Martin periodinane was added, and the reaction mixture was stirred for another 0.5 h. The mixture was diluted with ethyl acetate and a saturated aqueous sodium thiosulfate solution. The combined layers were mixed vigorously and then a saturated aqueous sodium bicarbonate solution was added. The layers were separated and the organic phase was dried over anhydrous magnesium sulfate and concentrated. The residue was purified by silica gel column chromatography eluting with a methanol:chloroform solution (1:9). The sample was further purified by HPLC using a Waters Symmetry C18 19 mm×150 mm column with 7 μm packing eluted with a five minute gradient of 30%–70% acetonitrile in water. The mobile phase contained a 0.1% trifluoroacetic acid modifier. This purification yielded 4 mg (9%) of (1S)-1-[(5,6-dichloro-1H-benzimidazol-1-yl)methyl]-2,2-dimethylpropyl 2oxo-3-[(2-pyridinylsulfonyl)amino]propylcarbamate. ES-LCMS m/z 542 (M+H) retention time=3.59 min. HRMS $C_{22}H_{25}Cl_2N_5O_5S$ m/z 542.1032 (M+H)$_{Cal}$; 542.1026 (M+H)$_{Obs}$.

Example 18

Preparation of (1S)-2,2-dimethyl-1-({4-[4-(trifluoromethyl)phenyl]-1H-imidazol-1-yl}methyl)propyl (1S)-1-{[(2-pyridinylsulfonyl)amino]acetyl}pentylcarbamate

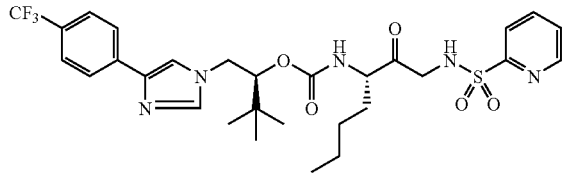

Example 18a

Preparation of 4-[4-(trifluoromethyl)phenyl]-1H-imidazole

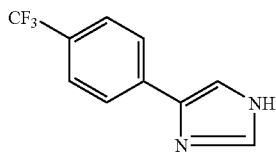

A mixture of 2.21 g (8.28 mmol) of 4-(trifluoromethyl)phenacylbromide and 9.3 mL (234 mmol) of formamide was stirred at 175° C. for 3 h. Then, 30 mL of 1N hydrochloric acid was added to the resulting solution, which was then heated to reflux. The resulting mixture was filtered and the filtrate was allowed to cool to room temperature before neutralization with concentrated ammonium hydroxide. The resulting mixture was partitioned between ethyl acetate and brine. The organic phase was dried over anhydrous magnesium sulfate, filtered, and concentrated. The residue was partially purified by silica gel column chromatography eluting with an ethyl acetate:methanol solution (9:1). Further purification by silica gel chromatography eluting with a hexane:acetone solution (1:1) yielded 1.18 g (67%) of 4-[4-(trifluoromethyl)phenyl]-1H-imidazole. $^1$H-NMR (DMSO-$d_6$): δ 12.34 (br s, 1H), 7.96 (d, J=8 Hz, 2H), 7.77 (s, 1H), 7.76 (s, 1H), 7.68 (d, J=8 Hz, 2H).

Example 18b

Preparation of (2S)-3,3-dimethyl-1-{4-[4-(trifluoromethyl)phenyl]-1H-imidazol-1-yl}-2-butanol

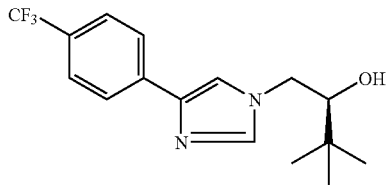

A solution 594 mg (5.94 mmol) of (S)-3,3-dimethyl-1,2-epoxybutane and 1.26 g (5.94 mmol) of 4'-trifluoromethyl-4-phenyl imidazole in 2.5 mL of ethanol was placed in a sealed tube and heated at 85° C. for 4 d. The mixture was cooled and concentrated, and the residue was purified by silica gel column chromatography eluting with ethyl acetate to yield 1.56 g (84%) of (2S)-3,3-dimethyl-1-{4-[4-(trifluoromethyl)phenyl]-1H-imidazol-1-yl}-2-butanol. $^1$H-NMR (DMSO-$d_6$): δ 7.93 (d, J=8 Hz, 2H), 7.84 (s, 1H), 7.68 (m, 3H), 5.01 (d, J=6 Hz, 1H), 4.15 (d, J=14 Hz, 1H), 3.73 (m, 1H), 3.31 (m, overlapping H$_2$O), 0.91 (s, 9H).

Example 18c

Preparation of (1S)-2,2-dimethyl-1-({4-[4-(trifluoromethyl)phenyl]-1H-imidazol-1-yl}methyl)propyl 4-nitrophenyl Carbonate

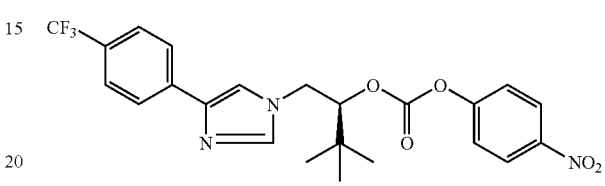

To solution of 1.91 g (6.12 mmol) of (2S)-3,3-dimethyl-1-{4-[4-(trifluoromethyl)phenyl]-1H-imidazol-1-yl}-2-butanol in 82 mL of tetrahydrofuran at 0° C. was added 4.2 mL (6.7 mmol) of 1.6 M n-butyllithium in hexanes, and the resulting solution was stirred for 10 min. A solution of 1.85 g (9.19 mmol) of 4-nitrophenyl chloroformate in 38 mL of tetrahydrofuran was added, and the solution was stirred at room temperature for 19 h. Saturated aqueous sodium bicarbonate was then added, and the mixture was extracted with ethyl acetate. The extract was washed with saturated aqueous sodium chloride, dried over anhydrous magnesium sulfate, filtered, and concentrated. The residue was purified by silica gel chromatography eluting with an ethyl acetate: hexanes solution (6:4) to give 1.83 g (sample contains 0.5 ethyl acetate by $^1$H-NMR for an effective weight of 1.68 g, 57%) of (1S)-2,2-dimethyl-1-({4-[4-(trifluoromethyl)phenyl]-1H-imidazol-1-yl}methyl)propyl 4-nitrophenyl carbonate. $^1$H-NMR (DMSO-$d_6$): δ 8.12 (d, J=7 Hz, 2H), 7.94 (d, J=8 Hz, 2H), 7.93 (s, 1H), 7.86 (s, 1H), 7.70 (d, J=8 Hz, 2H). 7.23 (d, J=9 Hz, 2H), 4.86 (d, J=8 Hz, 1H), 4.51 (d, J=13 Hz, 1H), 4.24(dd, J=14 Hz, J=10 Hz, 1H), 1.05(s, 9H).

Example 18d

Preparation of (1S)-2,2-dimethyl-1-({4-[4-(trifluoromethyl)phenyl]-1H-imidazol-1-yl}methyl)propyl (1S)-1-{(1R)-1-hydroxy-2-[(2-pyridinylsulfonyl)amino]ethyl}pentylcarbamate & (1S)-2,2-dimethyl-1-({4-[4-(trifluoromethyl)phenyl]-1H-imidazol-1-yl}methyl)propyl (1S)-1-{(1S)-1-hydroxy-2-[(2-pyridinylsulfonyl)amino]ethyl}pentylcarbamate

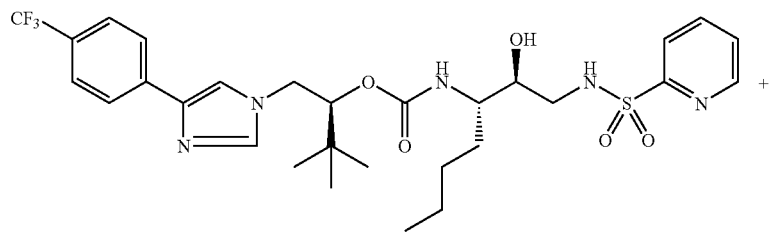

-continued

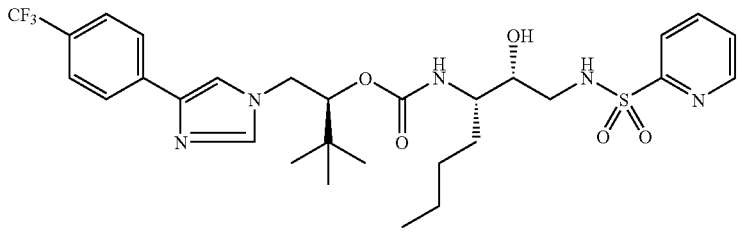

First, 0.24 mL (1.2 mmol) of diisopropylethylamine was added to a mixture of 179 mg (0.36 mmol) of (3S)-3-amino-2-hydroxy-N-(3-pyridinylmethyl)heptanamide dihydrochloride in 3 mL of anhydrous dimethylformamide. Then, 0.15 g (0.3 mmol) of (1S)-2,2-dimethyl-1-({4-[4-(trifluoromethyl)phenyl]-1H-imidazol-1-yl}methyl)propyl 4-nitrophenyl carbonate was added. The resulting solution was stirred for 3 d. It was then concentrated under reduced pressure, and the resulting residue was diluted with ethyl acetate. The resulting solution was washed with a saturated aqueous sodium bicarbonate solution, dried over anhydrous magnesium sulfate, filtered, and concentrated. The residue was purified by silica gel chromatography eluting with a methanol:chloroform solution (1:9) to afford 0.20 g (sample contains 0.67 chloroform and 0.25 dimethylformamide by $^1$H-NMR for an effective weight of 0.173 g, 92%) of (1S)-2,2-dimethyl-1-({4-[4-(trifluoromethyl)phenyl]-1H-imidazol-1-yl}methyl)propyl (1S)-1-{(1R)-1-hydroxy-2-[(2-pyridinylsulfonyl)amino]ethyl}pentylcarbamate & (1S)-2,2-dimethyl-1-({4-[4-(trifluoromethyl)phenyl]-1H-imidazol-1-yl}methyl)propyl (1S)-1-{(1S)-1-hydroxy-2-[(2-pyridinylsulfonyl)amino]ethyl}pentylcarbamate. ES-LCMS m/z 626 (M+H) retention time=3.45 min.

Example 18e

Preparation of (1S)-2,2-dimethyl-1-({4-[4-(trifluoromethyl)phenyl]-1H-imidazol-1-yl}methyl)propyl (1S)-1-{[(2-pyridinylsulfonyl)amino]acetyl}pentylcarbamate To a solution of 0.20 g (0.28 mmol) of (1S)-2,2-dimethyl-1-({4-[4-(trifluoromethyl)phenyl]-1H-imidazol-1-yl}methyl)propyl (1S)-1-{(1R)-1-hydroxy-2-[(2-pyridinylsulfonyl)amino]ethyl}pentylcarbamate and (1S)-2,2-dimethyl-1-({4-[4-(trifluoromethyl)phenyl]-1H-imidazol-1-yl}methyl)propyl (1S)-1-{(1S)-1-hydroxy-2-[(2-pyridinylsulfonyl)amino]ethyl}pentylcarbamate in 3 mL chloroform was added 0.15 g (0.35 mmol) Dess-Martin periodinane. The reaction mixture was stirred at room temperature for 1.5 h, then diluted with ethyl acetate and a saturated aqueous sodium thiosulfate solution. The layers were mixed vigorously, and then a saturated aqueous sodium bicarbonate solution was added. The layers were separated, and the organic phase was dried over anhydrous magnesium sulfate and concentrated. The residue was purified by silica gel column chromatography eluting with a methanol:chloroform solution (1:9) to yield 83.2 mg (48%) of (1S)-2,2-dimethyl-1-({4-[4-(trifluoromethyl)phenyl]-1H-imidazol-1-yl}methyl)propyl (1S)-1-{[(2-pyridinylsulfonyl)amino]acetyl}pentylcarbamate. ES-LCMS m/z 624 (M+H) retention time=3.51 min. HRMS $C_{29}H_{36}F_3N_5O_5S$ m/z 624.2468 (M+H)$_{Cal}$; 624.2463 (M+H)$_{Obs}$.

Example 19

Preparation of (1S)-1-{[4-(1H-imidazol-1-yl)phenoxy]methyl}-2,2-dimethylpropyl (1S)-1-{[(2-pyridinylsulfonyl)amino]acetyl}pentylcarbamate Example 19a Preparation of (1S)-1-{[4-(1H-Imidazol-1-yl)phenoxy]methyl}-2,2-dimethylpropyl 4-nitrophenyl Carbonate

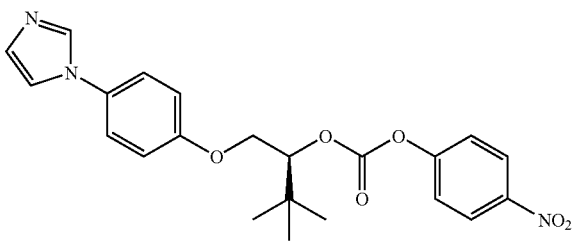

4-(Imidazol-1-yl)phenol was subjected to the procedure described in example 15a, and then treated with p-nitrophenyl chloroformate as described in example 15b to afford the title compound as a solid foam. 1H-NMR (DMSO-d$_6$: δ 8.31 (d, J=9 Hz, 2H), 8.14 (s, 1H), 7.65 (s, 1H), 7.55 (d, J=9 Hz, 2H), 7.51 (d, J=9 Hz, 2H), 7.11 (d, J=9 Hz, 2H), 7.06 (s, 1H), 4.93 (dd, J=9 Hz, J=2 Hz, 1H), 4.43 (dd, J=11 Hz, J=2 Hz, 1H), 4.16 (dd, J=11 Hz, J=9 Hz, 1H), 1.04 (s, 9H).

Example 19b

Preparation of (1S)-1-{[4-(1H-imidazol-1-yl)phenoxy]methyl}-2,2-dimethylpropyl (1S)-1-{(1S)-1-hydroxy-2-[(2-pyridinylsulfonyl)amino]ethyl}pentylcarbamate & (1S)-1-{[4-(1H-imidazol-1-yl)phenoxy]methyl}-2,2-dimethylpropyl (1S)-1-{(1R)-1-hydroxy-2-[(2-pyridinylsulfonyl)amino]ethyl}pentylcarbamate

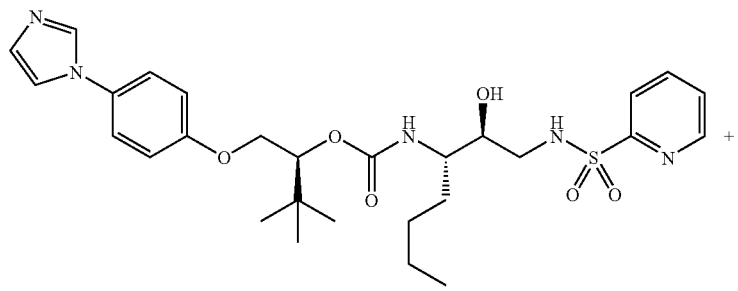

-continued

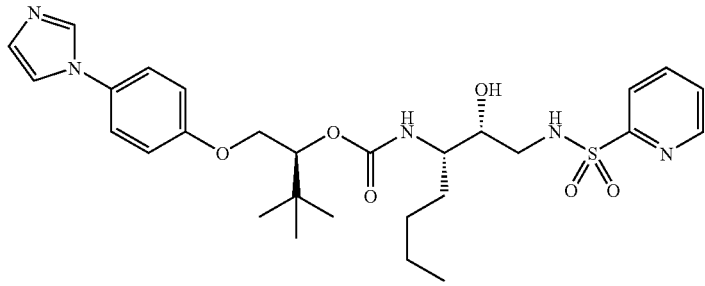

To 154 mg (0.31 mmol) of N-[(2S,3S)-3-amino-2-hydroxyheptyl]-2-pyridinesulfonamide hydrochloride & N-[(2R,3S)-3-amino-2-hydroxyheptyl]-2-pyridinesulfonamide in 3 mL of dimethylformamide, 132 mg (0.31 mmol) of (1S)-1-{[4-(1H-imidazol-1-yl)phenoxy]methyl}-2,2-dimethylpropyl 4-nitrophenyl carbonate was added, followed by 0.25 mL (1.43 mmol) of N,N-diisopropylethylamine. The reaction mixture was stirred for 18 h at room temperature. It was concentrated, a saturated sodium bicarbonate solution was added, and the mixture was extracted with ethyl acetate. The organic layer was washed with a saturated aqueous sodium chloride solution, dried over anhydrous magnesium sulfate, filtered, and concentrated. The residue was purified by silica gel column chromatography eluting with an methanol:chloroform solution (1:9) to yield 101.3 mg (57%) of (1S)-1-{[4-(1H-imidazol-1-yl)phenoxy]methyl}-2,2-dimethylpropyl (1S)-1-{(1S)-1-hydroxy-2-[(2-pyridinylsulfonyl)amino]ethyl}pentylcarbamate and (1S)-1-{[4-(1H-imidazol-1-yl)phenoxy]methyl}-2,2-dimethylpropyl (1S)-1-{(1R)-1-hydroxy-2-[(2-pyridinylsulfonyl)amino]ethyl}pentylcarbamate. ES-LCMS m/z 574 (M+H) Rt=2.7 min.

Example 19c

Preparation of (1S)-1-{[4-(1H-imidazol-1-yl)phenoxy]methyl}-2,2-dimethylpropyl (1S)-1-{[(2-pyridinylsulfonyl)amino]acetyl}pentylcarbamate

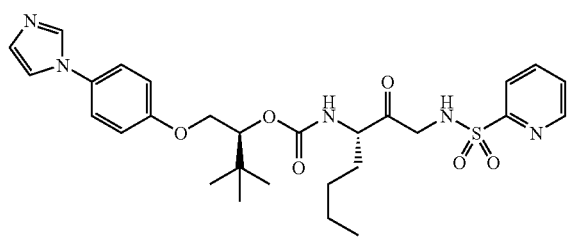

To a solution of 96.6 mg (0.17 mmol) of (1S)-1-{[4-(1H-imidazol-1-yl)phenoxy]methyl}-2,2-dimethylpropyl (1S)-1-{(1S)-1-hydroxy-2-[(2-pyridinylsulfonyl)amino]ethyl}pentylcarbamate & (1S)-1-{[4-(1H-imidazol-1-yl)phenoxy]methyl}-2,2-dimethylpropyl (1S)-1-{(1R)-1-hydroxy-2-[(2-pyridinylsulfonyl)amino]ethyl}pentylcarbamate in 1.7 mL of chloroform was added 85 mg (0.2 mmol) of Dess-Martin periodinane, and the mixture was stirred at room temperature for 1 h. A second portion of 15 mg (0.035 mmol) of Dess-Martin periodinane was added, and the reaction mixture was stirred for 0.5 h. It was then diluted with ethyl acetate and a saturated aqueous sodium thiosulfate solution. The layers were mixed vigorously, before a saturated aqueous sodium bicarbonate solution was added. The layers were separated, and the organic phase was dried over anhydrous magnesium sulfate and concentrated. The residue was purified by silica gel column chromatography eluting with a methanol:chloroform solution (1:9) to yield 21.6 mg (23%) of (1S)-1-{[4-(1H-imidazol-1-yl)phenoxy]methyl}-2,2-dimethylpropyl (1S)-1-{[(2-pyridinylsulfonyl)amino]acetyl}pentylcarbamate.
ES-LCMS m/z 572 (M+H) retention time=2.83 min. HRMS $C_{28}H_{37}N_5O_6S$ m/z 572.2543 $(M+H)_{Cal}$; 572.2526 $(M+H)_{Obs}$.

Biological Data

The compounds of the present invention elicit important and measurable pharmacological responses. Each of the compounds exemplified in the Examples section bind with high affinity ($IC_{50}$<10 μM) to the cathepsin K enzyme, as described by the cathepsin K assay recited below.

All assays for cathepsin K were carried out with human and rat recombinant enzyme. Assays for cathepsins S & V were also carried out with human recombinant enzyme. Assays for human cathepsins B, H, and L were carried out with enzyme prepared from human liver tissue. Standard assay conditions for the determination of kinetic constants used a fluorogenic peptide substrate, typically (5S,8S)-13-amino-5-benzyl-13-imino-3-methylene-N-(4-methyl-2-oxo-2H-chromen-7-yl)-6-oxo-1-phenyl-2-oxa-4,7,12-triaza-tridecane-8-carboxamide (Cbz-Phe-Arg-AMC), and were determined in 100 mM sodium acetate at pH 5.5 containing 10 mM dithiothreitol and 120 mM sodium chloride. A stock substrate solution of Cbz-Phe-Arg-AMC was prepared at a concentration of 50 mM in dimethyl sulfoxide. This substrate was diluted into the assay for a final substrate concentration of 10 μM in the rat cathepsin K, human cathepsin K, and human cathepsin B assays; a final substrate concentration of 5 μM in the human cathepsin L assay; and a final substrate concentration of 2 μM in the human cathepsin V assay.

A stock substrate solution of benzyl (1S)-1-{[((1S)-1-{[((1S)-4-{[amino(imino)methyl]amino}-1-{[(4-methyl-2-oxo-2H-chromen-7-yl)amino]carbonyl}butyl)amino]carbonyl}-2-methylpropyl)amino]carbonyl}-2-methylpropylcarbamate (Cbz-Val-Val-Arg-AMC) was prepared at a concentration of 10 mM in dimethyl sulfoxide. This substrate was diluted into the assay for a final substrate concentration of 10 μM in the human cathepsin S assay.

A stock substrate solution of (2S)-2-amino-5-{[amino(imino)methyl]amino}-N-(2-naphthyl)pentanamide hydrochloride (L-Arg-β-naphthalamide.HCl) was prepared at a concentration of 10 mM in dimethyl sulfoxide. This substrate was diluted into the assay for a final substrate concentration of 50 μM in the cathepsin H assay.

All assays contained 10% dimethyl sulfoxide. Independent experiments found that this level of dimethyl sulfoxide had no effect on enzyme kinetic constants. All assays were conducted at 30° C. Product fluorescence (excitation at 360 nm; emission at 440 nm, (except cathepsin H which used excitation at 340 nm; emission at 420 nm)) was monitored with a PerSeptive Biosystems Cytofluor II fluorescence plate reader. Product progress curves were generated over 2.3 h monitoring the formation of 7-amino-4-methylcoumarin product (or β-naphthalamide for cathepsin H).

Human and Rat Cathepsin K:

Scale-Up and Fermentation: The method of O'Reilly et al. (1994) was used for baculovirus expression with the following details: Two liters of *Spodoptera frugiperda* (Sf-9) cells (ATCC) were grown in Grace's Supplemented medium (Life Technologies) supplemented with 2 g/L glucose, 10% fetal bovine serum (HyClone) and 0.1% pluronic F-68 (Life Technologies). Cells were grown in a 6 L shake flask at 150 RPM at 28° C. for 24 h to a density of 106 cells/mL, and then infected at a multiplicity of infection (MOI) of 0.1. The cells continued to grow for 72 h post-infection, before the virus was harvested by centrifugation at 1400×g for 30 min. Virus was titered as described (Summers and Smith, 1987).

One and one-half liters of *Trichoplusia ni* (T. ni) High Five (TM) cells [JRH Biosciences, Woodland, Calif. (adapted to suspension and serum-free medium)] grown in Excell 405 (TM) medium (JRH Biosciences) with 50 ug/mL gentamicin (Life Technologies) were added to a 15 L stirred tank reactor (Quark Enterprises, Inc) at a density of ~0.5× 106 cells/mL. The cells were grown for 24 h at 28° C., 50 RPM, and 50% dissolved oxygen. Cells were then infected at a density of ~106 cells/mL with an MOI of 1 and grown for 48 h post-infection. Media were separated from cells at a rate of 1 L/min using the Centritech 100 (TM) continuous-flow centrifuge (DuPont) operating at 200×g.

Protein Purification: Media (human and rat) were filtered through a Whatman 3 filter, and then loaded onto a 25 mL Poros HS II (26 mm×47 mm) cation exchange column equilibrated in 25 mM sodium acetate at pH 5.5 (equilibration buffer). The column was washed until the absorbance reached the baseline value, and then the protein was eluted with a linear gradient from 0–2 M sodium chloride in the equilibration buffer. Column fractions were analyzed by SDS-PAGE, N-terminal sequencing, and mass spectrometry. Fractions containing the proform of cathepsin K were pooled and frozen at −80° C. The proform was concentrated in an Amicon Centriprep 10 and fractionated with a Superdex 75 column (26 mm×600 mm, Pharmacia) equilibrated in 400 mM sodium chloride, 25 mM sodium acetate at pH 5.5.

Cathepsin K Activation: The proform of cathepsin K was converted to mature cathepsin K by brief exposure to pH 4 in the presence of 5 mM L-cysteine. Typically, 5 mM L-cysteine was added to 10 mL of approximately 1 mg/mL procathepsin K. One mL of this solution was diluted ten-fold into 450 mM sodium acetate at pH 4.0 containing 5 mM L-cysteine. This solution was reacted at 23° C. for 2 min before neutralization with 2 mL 1.8 M sodium acetate at pH 6.0. The neutralized sample was added to the remaining 9 mL of procathepsin K. The mixture was incubated at 4° C. for 2–3 days. The activated cathepsin K was chromatographed on a Poros HS II column as described above.

Inhibition Studies

Potential inhibitors were evaluated using the progress curve method. Assays were carried out in the presence of variable concentrations of test compound. Reactions were initiated by addition of buffered solutions of inhibitor and substrate to enzyme. Data analysis was conducted according to one of two procedures depending on the appearance of the progress curves in the presence of inhibitors. For those compounds whose progress curves were linear, the enzymatic activity (RATE) was plotted against the concentration of test compound, including inhibitor concentration of zero ([I]=0), and the $IC_{50}$ determined from a fit of equation 1 to the data, $$\text{RATE} = V_{max}/(1 + ([I]/IC50)) \qquad (1)$$

where $V_{max}$ is the best fit estimate of the maximal enzymatic activity. $K_i$ values were calculated from $IC_{50}$ values using equation 2 assuming a competitive model.

$$K_i = IC_{50} * \left[1 - \frac{S}{(S + K_m)}\right] \qquad (2)$$

For those compounds whose progress curves showed downward curvature characteristic of time-dependent inhibition, the data from individual sets was analyzed using the computer program DynaFit (Kuzmic, P. *Anal. Biochem.* 1996, 237, 260–273) to give $K_i$ values according to the following kinetic mechanism:

$E+S \leftrightarrows ES$ $ES \rightarrow E+P$ $E \rightarrow EX$ $E+I \leftrightarrows EI$

TABLE 1

Inhibition of Cathepsin K ($K_i$ in nM)

| Example | hCat K $IC_{50}$ |
|---|---|
| 1 | +++ |
| 2 | +++ |
| 3 | +++ |
| 4 | + |
| 5 | ++++ |
| 6 | ++ |
| 7 | +++ |
| 8 | ++ |
| 9 | +++ |
| 10 | ++ |
| 11 | +++ |
| 12 | +++ |
| 13 | ++++ |
| 14 | ++++ |
| 15 | ++++ |
| 16 | ++++ |
| 17 | ++++ |
| 18 | ++++ |
| 19 | ++++ |

+ Inhibitors (about 10,000–1,000 nM)
++ Potent inhibitors (about 1000 to 100 nM)
+++ More potent inhibitors (about 100 to 10 nM)
++++ Most potent inhibitors (about 10–1 nM, or less)

TABLE 2

| Example | Inhibition of Cathepsins (Ki in nM) | | | | |
| --- | --- | --- | --- | --- | --- |
| | hCat B IC$_{50}$ | hCat K IC$_{50}$ | hCat L IC$_{50}$ | hCat S IC$_{50}$ | hCat V IC$_{50}$ |
| 6 | + | ++ | + | +++ | ++ |
| 16 | +++ | ++++ | +++ | ++++ | ++++ |

+ Inhibitors (about 10,000–1,000 nM)
++ Potent inhibitors (about 1000 to 100 nM)
+++ More potent inhibitors (about 100 to 10 nM)
++++ Most potent inhibitors (about 10–1 nM, or less)

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A compound of Formula (I):

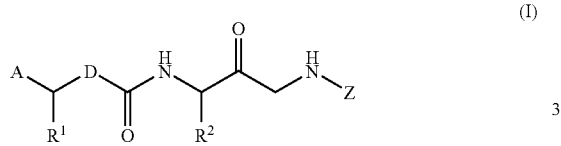

(I)

or a salt or solvate thereof, wherein

A is the group defined by $(Q^3)_p$-$(Q^2)_n$-$(Q^1)$-$(Q)_m$ wherein
  Q is CH$_2$ and m is 0, 1, or 2, or
  Q is OCH$_2$ and m is 1, or
  Q is N(R$^3$)CH$_2$ and m is 1, where R$^3$ is hydrogen or C$_1$–C$_6$ alkyl;
  Q$^1$ is aryl, heteroaryl, or heterocyclyl;
  Q$^2$ is CH$_2$ and n is 0 or 1, or
  Q$^2$ is O and n is 1, or
  Q$^2$ is N(R$^3$) and n is 1, where R$^3$ is hydrogen or C$_1$–C$_6$ alkyl;
  Q$^3$ is aryl or heteroaryl and p is 0 or 1;
R$^1$ is alkyl or cycloalkyl, said cycloalkyl may be optionally substituted with alkyl;
D is O or S;
R$^2$ is hydrogen or alkyl; and
Z is —(X$^1$)$_q$—(X$^2$);
  wherein X$^1$ is S(O)$_2$, C(O), or —CH$_2$—, and q is 0,1, or 2; and
  X$^2$ is aryl, heteroaryl, or heterocyclyl.

2. The compound of claim 1 wherein
Q is CH$_2$ and m is 1.

3. The compound of claim 1 wherein
Q$^1$ is heteroaryl.

4. The compound of claim 1 wherein n is 0.

5. The compound of claim 1 wherein Q$^3$ is aryl, said aryl being substituted with haloalkyl and p is 1.

6. The compound of claim 1 wherein Q$^1$ is

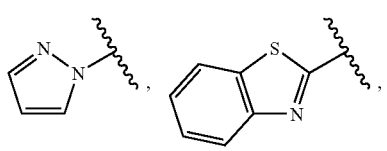

-continued

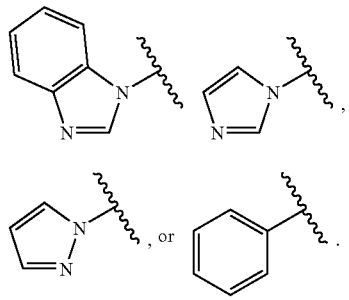

7. The compound of claim 1 wherein Q$^3$ is

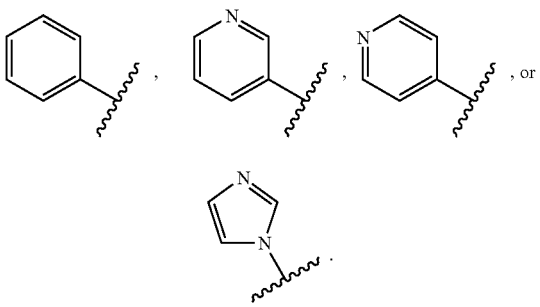

8. The compound of claim 1 wherein A is

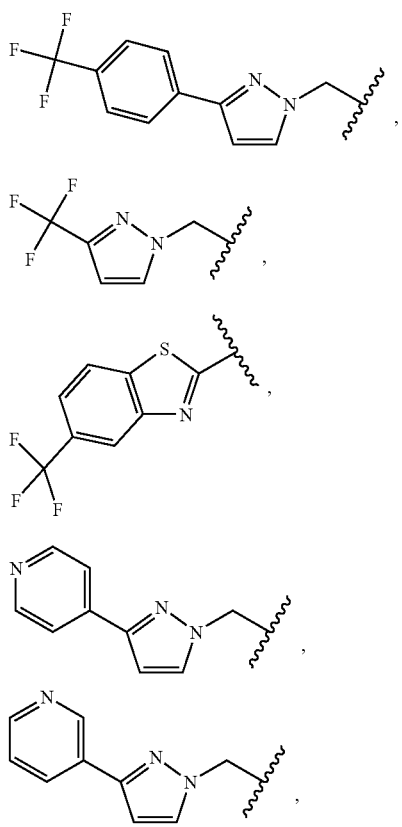

-continued

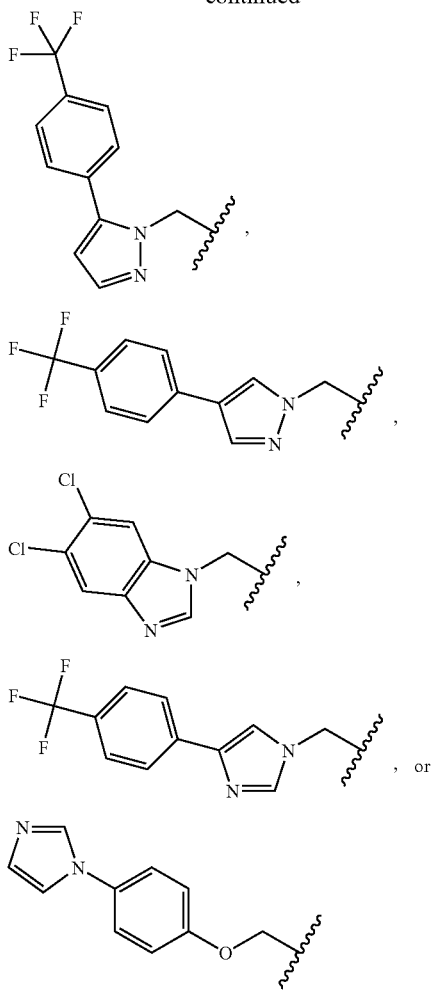

9. The compound of claim 1 wherein $R^1$ is lower alkyl.
10. The compound of claim 1 wherein $R^1$ is t-butyl.
11. The compound of claim 1 wherein $R^1$ is

12. The compound of claim 1 wherein $R^2$ is hydrogen, methyl, or n-butyl.
13. The compound of claim 1 wherein $R^2$ is methyl or n-butyl.
14. The compound of claim 1 wherein $R^2$ is n-butyl.
15. The compound of claim 1 wherein $R^2$ is

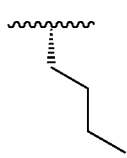

16. The compound of claim 1 wherein
Z is $—(X^1)_q—(X^2)$
wherein $X^1$ is $S(O)_2$;
q is 1; and
$X^2$ is heteroaryl.
17. The compound of claim 1 wherein Z is

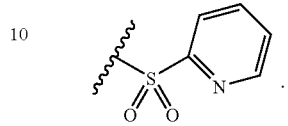

18. The compound of claim 1 wherein Z is

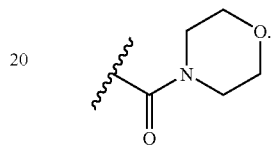

19. The compound of claim 1 wherein Z is

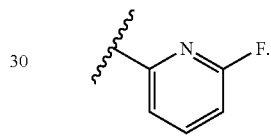

20. The compound as claimed in claim 1, selected from the group consisting of:
(1S)-2,2-dimethyl-1-({3-[4-(trifluoromethyl)phenyl]-1H-pyrazol-1-yl}methyl)propyl 2-oxo-3-[(2-pyridinylsulfonyl)amino]propylcarbamate;
(1S)-2,2-dimethyl-1-({3-[4-(trifluoromethyl)phenyl]-1H-pyrazol-1-yl}methyl)propyl (1S)-1-methyl-2-oxo-3-[(2-pyridinylsulfonyl)amino]propylcarbamate;
(1S)-2,2-dimethyl-1-({3-[4-(trifluoromethyl)phenyl]-1H-pyrazol-1-yl}methyl)propyl (1S)-1-{[(2-pyridinylsulfonyl)amino]acetyl}pentylcarbamate;
(1S)-2,2-dimethyl-1-({3-[4-(trifluoromethyl)phenyl]-1H-pyrazol-1-yl}methyl)propyl (1S)-1-{[(4-morpholinylcarbonyl)amino]acetyl}pentylcarbamate;
(1S)-2,2-dimethyl-1-({3-[4-(trifluoromethyl)phenyl]-1H-pyrazol-1-yl}methyl)propyl (1S)-1-{[(6-fluoro-2-pyridinyl)amino]acetyl}pentylcarbamate;
(3S)-1-(1,3-benzothiazol-2-yl)-4,4-dimethylpyrrolidinyl (1S)-1-{[(2-pyridinylsulfonyl)amino]acetyl}pentylcarbamate;
(1S)-2,2-dimethyl-1-{[3-(trifluoromethyl)-1H-pyrazol-1-yl]methyl}propyl (1S)-1-{[(2-pyridinylsulfonyl)amino]acetyl}pentylcarbamate;
(1S)-2,2-dimethyl-1-{[3-(trifluoromethyl)-1H-pyrazol-1-yl]methyl}propyl (1S)-1-methyl-2-oxo-3-[(2-pyridinylsulfonyl)amino]propylcarbamate;
(1S)-2,2-dimethyl-1-[5-(trifluoromethyl)-1,3-benzothiazol-2-yl]propyl (1S)-1-{[(2-pyridinylsulfonyl)amino]acetyl}pentylcarbamate;
(1S)-2,2-dimethyl-1-[5-(trifluoromethyl)-1,3-benzothiazol-2-yl]propyl (1S)-1-methyl-2-oxo-3-[(2-pyridinylsulfonyl)amino]propylcarbamate;

(1S)-2,2-dimethyl-1-({4-[4-(trifluoromethyl)phenyl]-1H-pyrazol-1-yl}methyl)propyl (1S)-1-{[(2-pyridinylsulfonyl)amino]acetyl}pentylcarbamate;

(1S)-2,2-dimethyl-1-({5-[4-(trifluoromethyl)phenyl]-1H-pyrazol-1-yl}methyl)propyl (1S)-1-{[(2-pyridinylsulfonyl)amino]acetyl}pentylcarbamate;

(1S)-2,2-dimethyl-1-{[3-(3-pyridinyl)-1H-pyrazol-1-yl]methyl}propyl (1S)-1-{[(2-pyridinylsulfonyl)amino]acetyl}pentylcarbamate;

(1S)-2,2-dimethyl-1-{[3-(4-pyridinyl)-1H-pyrazol-1-yl]methyl}propyl (1S)-1-{[(2-pyridinylsulfonyl)amino]acetyl}pentylcarbamate;

(1S)-1-[(5,6-dichloro-1H-benzimidazol-1-yl)methyl]-2,2-dimethylpropyl (1S)-1-{[(2-pyridinylsulfonyl)amino]acetyl}pentylcarbamate;

(1S)-1-[(5,6-dichloro-1H-benzimidazol-1-yl)methyl]-2,2-dimethylpropyl (1S)-1-methyl-2-oxo-3-[(2-pyridinylsulfonyl)amino]propylcarbamate;

(1S)-1-[(5,6-dichloro-1H-benzimidazol-1-yl)methyl]-2,2-dimethylpropyl 2-oxo-3-[(2-pyridinylsulfonyl)amino]propylcarbamate;

(1S)-2,2-dimethyl-1-({4-[4-(trifluoromethyl)phenyl]-1H-imidazol-1-yl}methyl)propyl (1S)-1-{[(2-pyridinylsulfonyl)amino]acetyl}pentylcarbamate;

(1S)-1-{[4-(1H-imidazol-1-yl)phenoxy]methyl}-2,2-dimethylpropyl (1S)-1-{[(2-pyridinylsulfonyl)amino]acetyl}pentylcarbamate.

21. A compound of Formula (II):

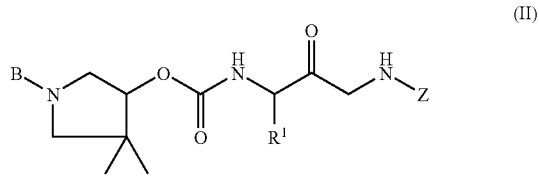

(II)

or a salt or solvate thereof, wherein

B is -(Q$^1$)$_a$-(Q$^2$)$_b$-(Q$^3$)

wherein

Q$^1$ is C(O), S(O)$_2$, or CR$^2$R$^3$, where R$^2$ and R$^3$ each are independently selected from hydrogen or C$_{1-C6}$ alkyl, and a is 0, 1, 2, or 3;

Q$^2$ is O, S, NR$^2$, or CR$^2$R$^3$, where R$^2$ and R$^3$ each are independently selected from hydrogen or C$_{1-C6}$ alkyl, and b is 0, 1, 2, or 3; and Q$^3$ is aryl, heteroaryl, heterocyclyl, aralkyl, or alkylene-heterocyclyl;

R$^1$ is hydrogen or alkyl;

Z is —(X$^1$)$_q$—(X$^2$);

wherein X$^1$ is S(O)$_2$, C(O), or alkyl, and q is 0 or 1; and

X$^2$ is aryl, heteroaryl, or heterocyclyl.

22. The compound of claim 21 wherein a is 0; b is 0; and Q$^3$ is heterocyclyl.

23. The compound of claim 21 wherein Q$^3$ is:

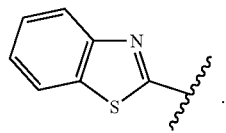

24. The compound of claim 21 wherein
Z is —(X$^1$)$_p$—(X$^2$)
where X$^1$ is S(O)$_2$;
p is 1; and
X$^2$ is heteroaryl.

25. The compound of claim 21 wherein Z is

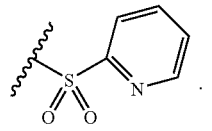

26. A pharmaceutical composition comprising:
a therapeutically effective amount of a compound as claimed in claim 1.

27. A pharmaceutical composition comprising:
a therapeutically effective amount of a compound as claimed in claim 1, or a salt, solvate, or a physiologically functional derivative thereof and one or more of pharmaceutically acceptable carriers, diluents and excipients.

28. A method of treating osteoporosis, comprising:
administering to said mammal a therapeutically effective amount of a compound as claimed in claim 1, or a salt or thereof.

29. A method of treating osteoporosis, comprising:
administering to said mammal therapeutically effective amounts of
(i) a compound as claimed in claim 1, or a salt or solvate thereof; and
(ii) at least one bone building agent.

30. A pharmaceutical composition comprising:
a therapeutically effective amount of a compound as claimed in claim 21.

31. A pharmaceutical composition comprising:
a therapeutically effective amount of a compound as claimed in claim 21, or a salt or solvate thereof and one or more of pharmaceutically acceptable carriers, diluents and excipients.

32. A method of treating osteoporosis, comprising:
administering to said mammal a therapeutically effective amount of a compound as claimed in claim 21, or a salt or solvate thereof.

33. A method of treating osteoporosis, comprising:
administering to said mammal therapeutically effective amounts of
(i) a compound as claimed in claim 21, or a salt or solvate thereof; and
(ii) at least one bone building agent.

* * * * *